(12) United States Patent
Matsuo et al.

(10) Patent No.: US 6,395,159 B2
(45) Date of Patent: *May 28, 2002

(54) OXYGEN SENSOR

(75) Inventors: Kouji Matsuo, Kasugai; Satoshi Ishikawa, Komaki; Shoji Akatsuka, Bisai; Shoichi Ohtsuki, Komaki; Takashi Mizukusa, Kasugai; Hiromichi Hayashi, Nagoya, all of (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

This patent is subject to a terminal disclaimer.

(21) Appl. No.: 09/143,384

(22) Filed: Aug. 28, 1998

(30) Foreign Application Priority Data

| Aug. 29, 1997 | (JP) | 9-249651 |
|---|---|---|
| Aug. 29, 1997 | (JP) | 9-249652 |
| Aug. 29, 1997 | (JP) | 9-249824 |
| Aug. 29, 1997 | (JP) | 9-249825 |
| Aug. 29, 1997 | (JP) | 9-249826 |
| Aug. 29, 1997 | (JP) | 9-249838 |
| Aug. 29, 1997 | (JP) | 9-249858 |
| Aug. 29, 1997 | (JP) | 9-249859 |
| Aug. 29, 1997 | (JP) | 9-249860 |

(51) Int. Cl.[7] .......................................... G01N 27/407
(52) U.S. Cl. ..................................... 204/427; 204/428
(58) Field of Search ............................... 204/421–429; 29/863

(56) References Cited

U.S. PATENT DOCUMENTS

| 2,226,849 A | * 12/1940 | Douglas | |
| 3,146,519 A | * 9/1964 | Redwine | 29/863 |
| 3,871,071 A | * 3/1975 | Luongo | 29/863 |
| 3,953,566 A | 4/1976 | Gore | 264/288 |
| 3,962,153 A | 6/1976 | Gore | 260/2.5 R |
| 4,096,227 A | 6/1978 | Gore | 264/210 R |
| 4,187,390 A | 2/1980 | Gore | 174/102 R |
| 4,323,440 A | 4/1982 | Akatsuka | 204/195 |
| 4,362,609 A | * 12/1982 | Sano et al. | 204/428 |
| 4,556,475 A | * 12/1985 | Bayha et al. | 204/428 |
| 4,569,748 A | * 2/1986 | Yamakawa et al. | 204/428 |
| 4,596,837 A | 6/1986 | Yamamoto et al. | 521/145 |
| 4,786,399 A | 11/1988 | Wertheimer et al. | 204/427 |
| 4,824,550 A | * 4/1989 | Ker et al. | 204/427 |

(List continued on next page.)

FOREIGN PATENT DOCUMENTS

| DE | 196 22 397 A | 12/1996 |
| DE | 197 03 458 A | 7/1997 |
| EP | 0 145 175 | 6/1985 |
| EP | 0 661 336 A1 | 5/1995 |
| EP | 0 702 229 A | 3/1996 |
| EP | 0 811 840 | 12/1997 |
| GB | 1 459 670 | 12/1976 |
| GB | 2 309 312 A | 7/1997 |
| JP | 42-13560 | 8/1942 |
| JP | 59-152825 | 8/1984 |
| JP | 3-221541 | 9/1991 |
| JP | 4-157358 | 5/1992 |
| JP | 8-201338 | 8/1996 |

*Primary Examiner*—T. Tung
(74) *Attorney, Agent, or Firm*—Morgan, Lewis & Bockius LLP

(57) ABSTRACT

An oxygen sensor is constituted by a ceramic separator being placed so that the rear thereof enters the inside of a filter holding part and the front enters the inside of a casing and formed with a plurality of lead insertion holes axially penetrating the ceramic separator and an elastic seal member being fitted elastically into a rear opening of the filter holding part and having seal lead insertion holes for inserting leads for sealing the gap between the outer faces of the leads and the inner face of the filter holding part. The rear end face of the ceramic separator is positioned on the rear side behind a gas introduction hole in the axial direction and a predetermined gap is formed between the elastic seal member and the ceramic separator at least at the lead insertion position.

35 Claims, 43 Drawing Sheets

U.S. PATENT DOCUMENTS

| | | | | |
|---|---|---|---|---|
| 4,828,516 A | * | 5/1989 | Shaffer | 29/863 |
| 4,883,643 A | | 11/1989 | Nishio et al. | 422/94 |
| 4,966,560 A | * | 10/1990 | Marzouk | 29/863 |
| 5,031,445 A | | 7/1991 | Kato et al. | 73/23.31 |
| 5,139,639 A | | 8/1992 | Holleboom | 204/427 |
| 5,423,972 A | * | 6/1995 | Mann et al. | 204/427 |
| 5,462,586 A | | 10/1995 | Sugiyama et al. | 96/13 |
| 5,573,650 A | * | 11/1996 | Fukaya et al. | 204/428 |
| 5,695,625 A | * | 12/1997 | Yamada et al. | 204/428 |
| 5,759,365 A | * | 6/1998 | Yamada et al. | 204/427 |
| 5,785,829 A | * | 7/1998 | Watanabe | 204/428 |
| 5,804,050 A | * | 9/1998 | Hayakawa et al. | 204/424 |
| 5,830,339 A | * | 11/1998 | Watanabe et al. | 204/428 |
| 5,900,129 A | * | 5/1999 | Tsuji et al. | |

* cited by examiner

FIG. 6A
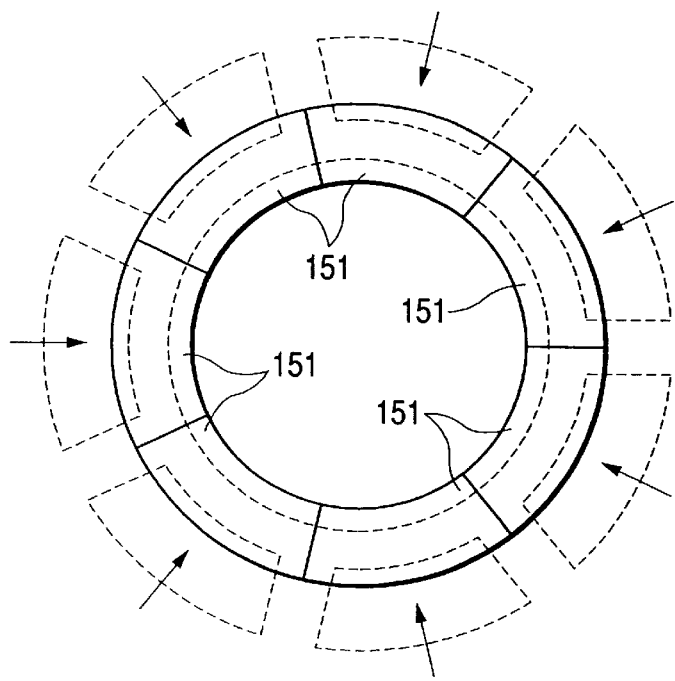
FIG. 6B
FIG. 6C
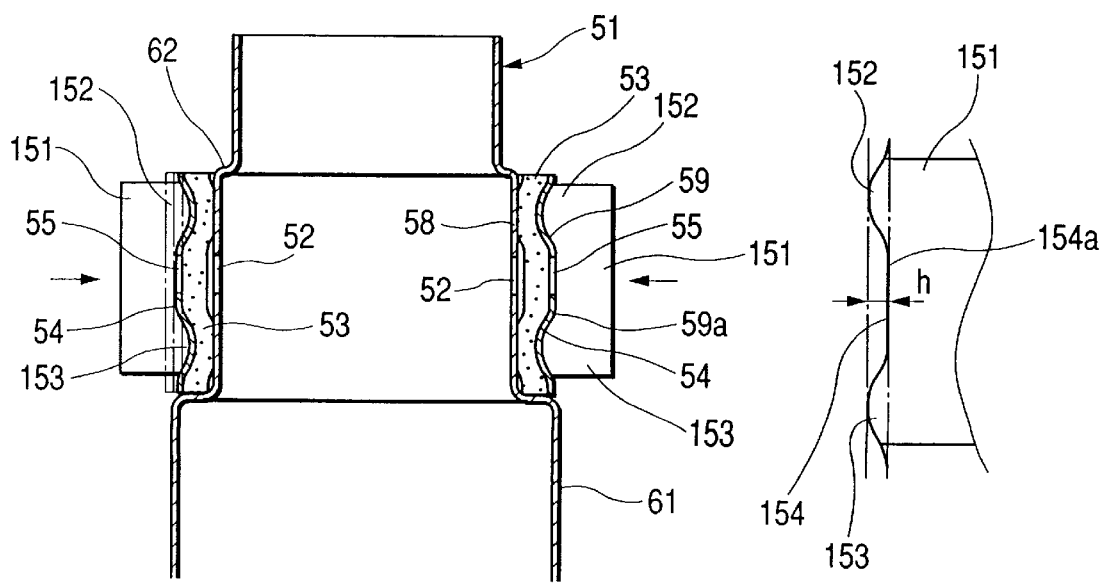

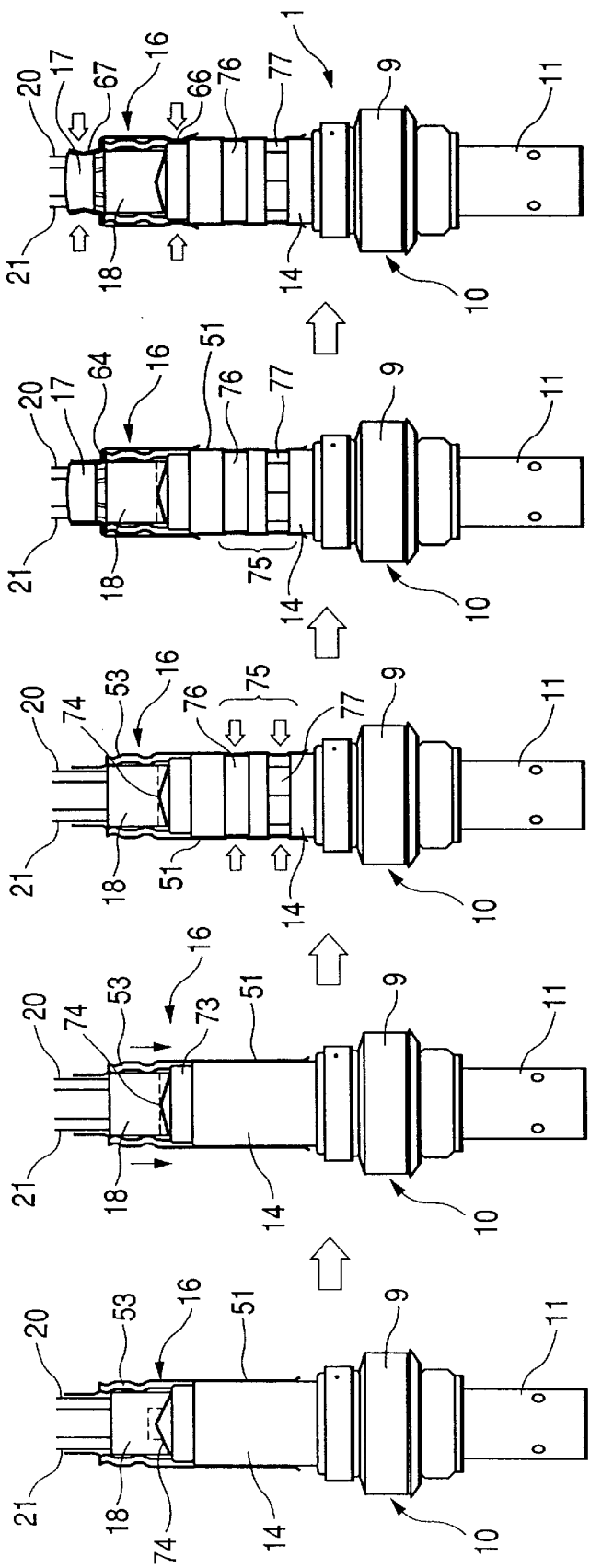

VIEWED FROM ARROW A

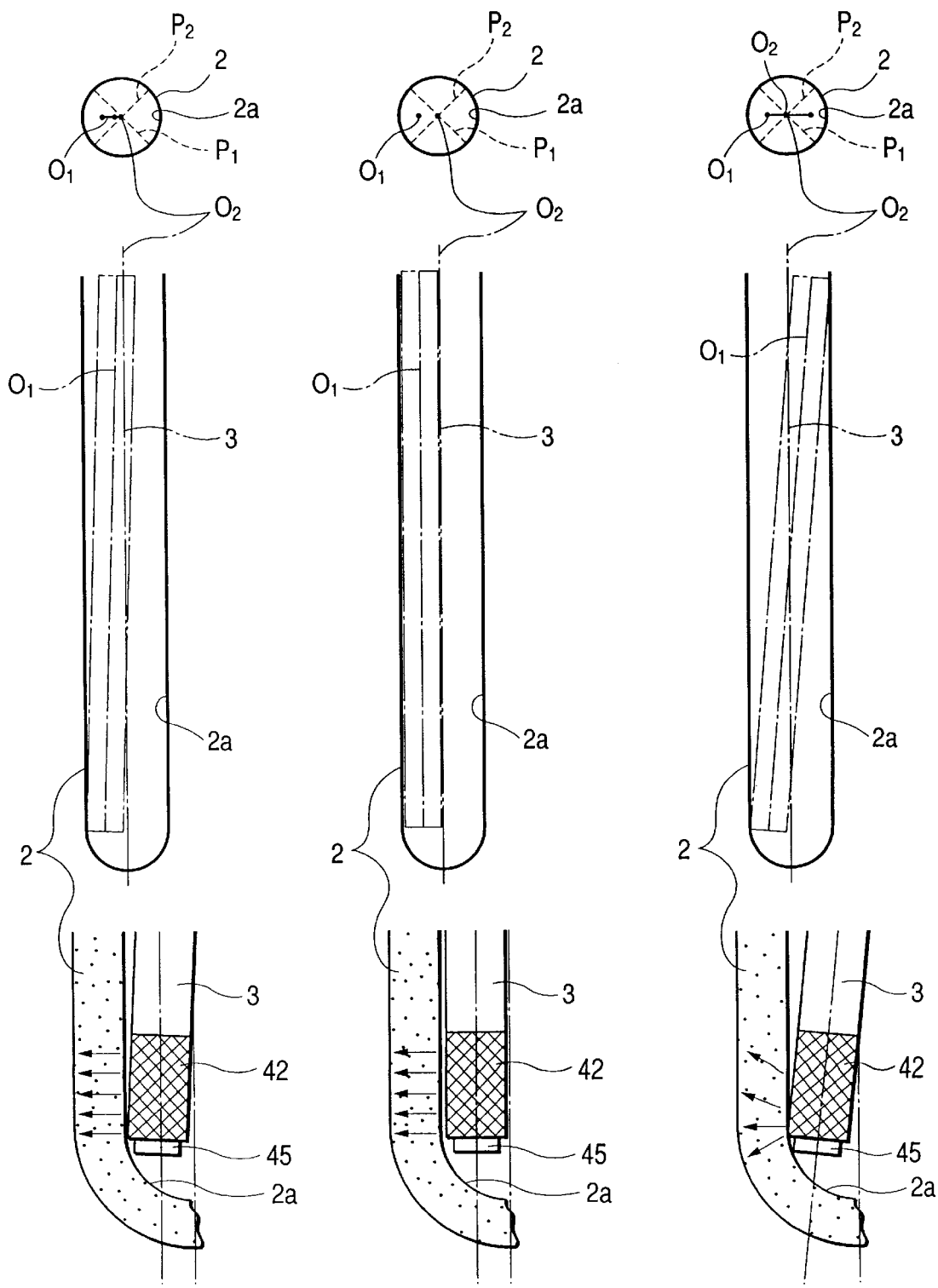

FIG. 35A
FIG. 35B
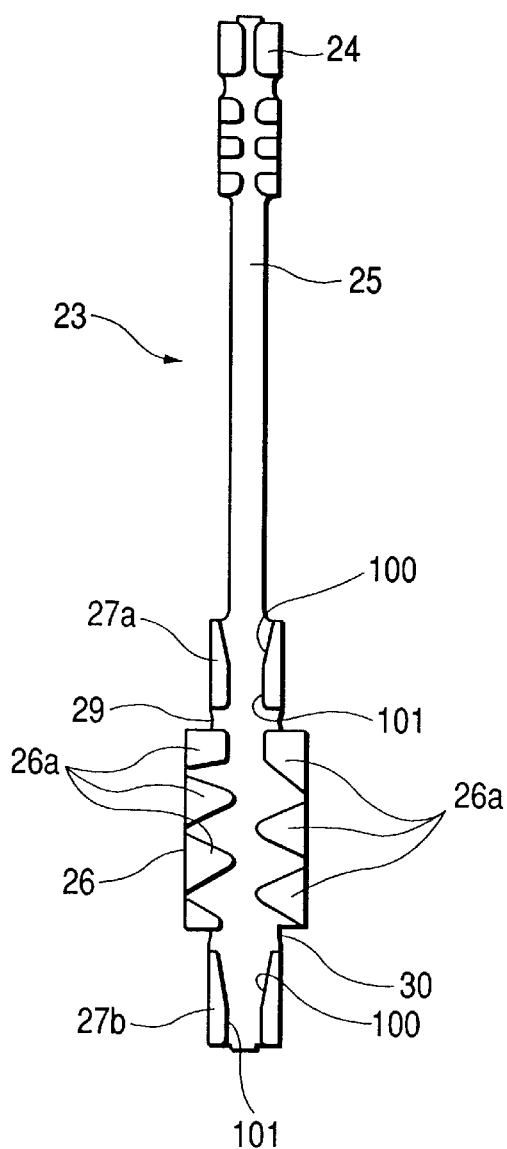
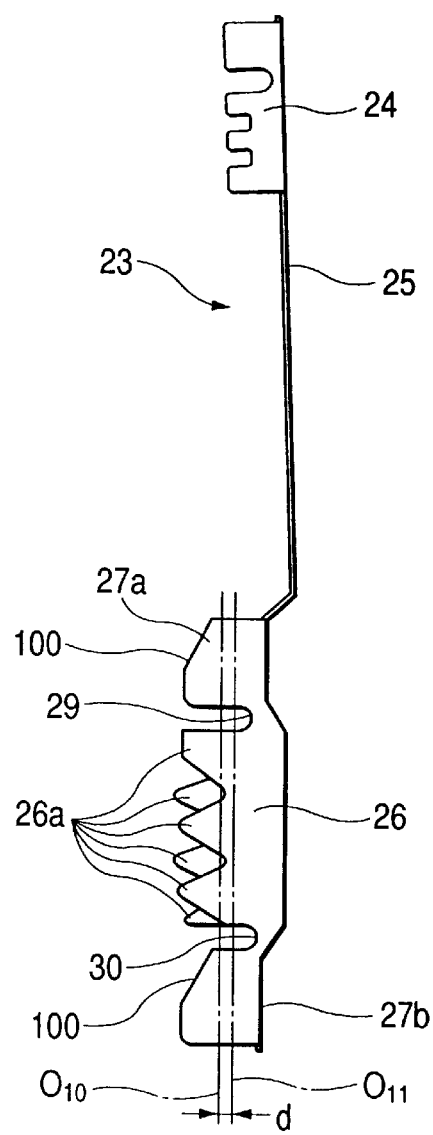

$\tan\theta = \dfrac{d}{L}$ $d = L\tan\theta$ $0.1° \leq \theta \leq 0.5°$ $0.0017L \leq d \leq 0.0087L$

OXYGEN SENSOR

BACKGROUND OF THE INVENTION

1. Field of the Invention

The present invention relates to an oxygen sensor for detecting the oxygen concentration in exhaust gas in an internal combustion engine, for example, or an oxygen sensor for detecting oxygen in a predetermined gas.

2. Description of the Related Art

In recent years, various oxygen sensors used for air fuel ratio control, etc., in internal combustion engines of automobile engines, etc., have been developed. Especially high-performance, long-life oxygen sensors for detecting the oxygen concentration in exhaust gas have also been finding increasing demand to cope with environmental protection problems of air pollution, etc., caused by exhaust gases.

For example, representative one of such oxygen sensors widely used has a structure wherein an oxygen sensing element formed like a hollow shaft closed at the tip made of an oxygen ion conductive solid electrolyte of $ZrO_2$, etc., is housed in a cylindrical casing, the outer face of the tip of the oxygen sensing element is brought into contact with a detected atmosphere, and air as a reference gas is introduced into the space inside the oxygen sensing element for measuring the oxygen concentration in the detected atmosphere based on an oxygen concentration cell electromotive force occurring in the sensing element.

By the way, to install an oxygen sensor as described above in an automobile, the oxygen sensor often is attached to an exhaust pipe, etc., near a tire of the vehicle, for example, in addition to an engine room. In such a situation, the oxygen sensor is exposed to a considerable hostile environment in which it receives a jet of water drops at the rainy driving time, at the washing time, etc., dirt of oil, etc., is deposited on the oxygen sensor, or the oxygen sensor receives shock of jumped-up pebbles, etc. In this case, to protect the oxygen sensing element from water drop and dirt deposition, a highly strong and highly sealed structure as much as possible must be adopted as the structure of the casing housing the oxygen sensing element. However, air as the sensing element reference gas needs to be introduced into the casing and thus a communication section with the outside must always be provided. That is, to operate the oxygen sensor stably over a long term under a hostile environment, contradictory problems of enhancing fluid sealability of water, etc., at a given level or more and providing permeability need to be solved at the same time. To meet such a demand, for example, Japanese Patent Laid-Open No. Hei 8-201338 discloses an oxygen sensor of a structure wherein an air hole is made in a casing and is covered with a water repellent filter, whereby ventilation is allowed while the entry of water drops, etc., is blocked.

In the oxygen sensor, generally a ceramic separator is placed in the casing and leads from the oxygen sensing element or a heating element for heating the oxygen sensing element are passed through lead insertion holes as a structure for drawing out the leads from the casing. Such a ceramic separator prevents or suppresses a short circuit between the leads or terminals following the leads, for example. Each lead extends from a rear opening of the casing to the outside and the space between the lead and the opening is sealed by an elastic seal member of a rubber tap, etc., fitted into the opening. Normally, lead insertion holes made in the ceramic separator and the elastic seal member are formed so that their centers are arranged on a phantom circumferential path (pitch circle).

In the disclosed oxygen sensor, the leads are inserted into the elastic seal member and the ceramic separator at different pitch circle diameters and to absorb the pitch circle diameter differences, a comparatively large gap is formed between the elastic seal member and the ceramic separator. A ventilation structure consisting of an air hole and a water repellent filter for covering the air hole is provided corresponding to the gap position.

However, in the disclosed oxygen sensor, the ventilation structure containing the water repellent filter is formed corresponding to the gap between the elastic seal member and the ceramic separator, thus if a strong impulse force acts on the part, there is a possibility that the casing will be largely deformed at the position corresponding to the gap. In this case, it is feared that a cylindrical member fixing and sealing the filter from the outside, for example, by crimping may loosen because of the deformation of the casing, that the filter seal may be broken, and that water drops, etc., may bypass the filter and enter the casing through the air hole. Since nothing blocks the way of leaked water drops in the proximity of the air hole, the probability is also high that water drops will leak into the oxygen sensing element through a through hole, etc., made in the axial direction of the ceramic separator, for example.

SUMMARY OF THE INVENTION

It is an object of the invention to provide an oxygen sensor having a structure in which a seal of a filter forming a ventilation structure is hard to break although a predetermined gap is formed between an elastic seal member and a ceramic separator.

An oxygen sensor according to the present invention comprises: an oxygen sensing element shaped like a shaft; a cylindrical casing for housing the oxygen sensing element; and a cover member being placed coaxially with the casing so that an inside of the cover member communicates with the casing and coupled to the casing from an axial rear; wherein the cover member is placed so as to overlap the casing on an axial front of the cover member from an outside;

further wherein the overlap is formed with: a main crimp part being formed annularly in a circumferential direction of the cover member and the casing by crimping the cover member toward the casing; and a rotation prevention part for preventing the cover member and the casing from relatively rotating around the axis of the cover member and the casing in the annular main crimp part.

An oxygen sensor according to the present invention comprises: an oxygen sensing element shaped like a shaft; a cylindrical casing for housing the oxygen sensing element; a ceramic separator being placed coaxially with the casing, supported directly or indirectly via a member in a casing support part formed at a rear end of the casing, and formed with a plurality of lead insertion holes axially penetrating the ceramic separator for inserting leads from the oxygen sensing element; a cover member being placed coaxially with the casing and coupled to the casing from a rear with the ceramic separator covered from an outside while allowing the leads to extend to the rear outside of the cover member; and a metal elastic member being placed at least between the cover member and the ceramic separator or between the casing support part and the ceramic separator in a compression state for producing a sandwich retaining force for the ceramic separator between the cover member and the casing support part.

An oxygen sensor according to the present invention comprises: an oxygen sensing element shaped like a shaft; a cylindrical casing for housing the oxygen sensing element; a gas introduction structure having a filter holding part making a cylindrical form coaxial with the casing on a rear of the casing, having an inside communicating with the casing, and being formed in a wall with one or more gas introduction holes and a filter being placed so as to block the gas introduction hole or holes of the filter holding part for rejecting permeation of liquid and allowing gas to pass through, the gas introduction structure for introducing outside air into the casing through the filter and the gas introduction hole or holes; and a protective cover being formed like a cylinder for covering the gas introduction structure from an outside thereof for blocking or suppressing a direct jet of liquid drops to the filter or deposition of deposits of oil, dirt, etc., on the filter.

An oxygen sensor according to the present invention comprises: an oxygen sensing element shaped like a shaft; a cylindrical casing for housing the oxygen sensing element; a gas introduction structure comprising a filter holding part making a cylindrical form almost coaxial with the casing on a rear of the casing, having an inside communicating with an inside of the casing, and being formed in a wall with one or more gas introduction holes, a filter being placed so as to block the gas introduction hole or holes on an outside of the filter holding part for rejecting permeation of liquid and allowing gas to pass through, and an auxiliary filter holding part being formed like a cylinder placed on an outside of the filter and formed in a wall with one or more auxiliary gas introduction holes for sandwiching the filter between the auxiliary filter holding part and the filter holding part, for introducing outside air into the casing through the auxiliary gas introduction hole, the filter, and the gas introduction hole; wherein the filter comes in intimate contact with an inner face of the auxiliary filter holding part at least in surroundings of the auxiliary gas introduction hole and a predetermined gap is formed between the outer face of the filter holding part and the filter at least in surroundings of the gas introduction hole.

An oxygen sensor according to the present invention comprises: an oxygen sensing element shaped like a shaft; a cylindrical casing for housing the oxygen sensing element; a filter assembly being placed almost coaxially with the casing as a cylindrical body separate from the casing and coupled to the casing from a rear while allowing leads from the oxygen sensing element to extend to the rear outside of the filter assembly; and a coupling part for coupling the filter assembly and the casing, wherein the filter assembly comprises: a filter holding part making a cylindrical form almost coaxially coupled to the casing from a rear of the casing, having an inside communicating with an inside of the casing, and being formed in a wall with one or more gas introduction holes; a filter being placed so as to block the gas introduction hole or holes in the filter holding part from an inner or outer face side for rejecting permeation of liquid and allowing gas to pass through; and an auxiliary filter holding part for fixing the filter to the filter holding part, outside air introducing into the casing through the filter and the gas introduction hole.

An oxygen sensor according to the present invention comprises: an oxygen sensing element shaped like a hollow shaft with a tip closed; a shaft-like heating element being placed in the hollow part of the oxygen sensing element for heating the oxygen sensing element; a cylindrical casing for housing the oxygen sensing element; and a ceramic separator being placed almost coaxially with a rear end of the oxygen sensing element and formed with a plurality of lead insertion holes axially penetrating the ceramic separator for inserting leads from the oxygen sensing element and the heating element; wherein the lead insertion holes are arranged so as to surround a center axis of the ceramic separator; the ceramic separator is formed with a heating element end housing hole opened at one end in the front end face of the ceramic separator with a bottom positioned in an axial intermediate part of the ceramic separator and an inner diameter set larger than an outer diameter of the heating element, the heating element end housing hole being formed by cutting away a center of the ceramic separator so as to overlap the separator lead insertion holes from the inside and the rear end part of the heating element being housed in the heating element end housing hole; and the heating element is offset so that a center axis thereof is one-sided with respect to a center axis of the hollow part of the oxygen sensing element in the proximity of a heating part of the heating element.

An oxygen sensor according to the present invention comprises: an oxygen sensing element shaped like a shaft; a cylindrical casing for housing the oxygen sensing element; a ceramic separator being placed in the casing and formed with a plurality of lead insertion holes axially penetrating the ceramic separator for inserting leads from the oxygen sensing element; and an elastic seal member being coaxially integrated with a rear opening or a rear of the casing and having an inside fitted elastically into an inside of a different cylindrical body communicating with the casing and seal lead insertion holes for inserting the leads for sealing a gap between outer faces of the leads and an inner face of the casing or the different cylindrical body; wherein an axial rear end face of the ceramic separator adheres closely to an axial front end face of the elastic seal member, that the ceramic separator is formed with a ventilation communication part axially penetrating the ceramic separator, and that an opening of the ventilation communication part on a side near to the elastic seal member in the axial direction is made at a position where the opening is not shielded by the elastic seal member.

An oxygen sensor according to the present invention comprises: an oxygen sensing element shaped like a shaft; a cylindrical casing for housing the oxygen sensing element; a gas introduction structure comprising a filter holding part making a cylindrical form almost coaxial with the casing on a rear of the casing, having an inside communicating with an inside of the casing, and being formed in a wall with one or more gas introduction holes, a filter being placed so as to block the gas introduction hole or holes on an outside of the filter holding part for rejecting permeation of liquid and allowing gas to pass through, and an auxiliary filter holding part being formed like a cylinder placed on an outside of the filter and formed in a wall with one or more auxiliary gas introduction holes for sandwiching the filter between the auxiliary filter holding part and the filter holding part, for introducing outside air into the casing through the auxiliary gas introduction hole, the filter, and the gas introduction hole; wherein the filter holding part has an axial front relative to a stepped part formed in an axial intermediate part of the filter holding part as a first portion and a rear as a second portion so that the second portion is made smaller in diameter than the first portion, the gas introduction hole being made in a wall of the second portion; the auxiliary filter holding part is placed so as to spread across the first and second portions of the filter holding part; a main coupling part for coupling the filter holding part and the auxiliary filter holding part to each other with the filter between is formed at a position corresponding to the second portion; and an auxiliary coupling part for coupling the filter holding part and the auxiliary filter holding part to each other is formed at a position corresponding to the first portion.

An oxygen sensor according to the present invention comprises: an oxygen sensing element shaped like a shaft; a cylindrical casing for housing the oxygen sensing element; a gas introduction structure having a filter holding part making a cylindrical form almost coaxial with the casing on a rear of the casing, having an inside communicating with an inside of the casing, and being formed in a wall with one or more gas introduction holes and a filter being placed so as to block the gas introduction hole or holes of the filter holding part for rejecting permeation of liquid and allowing gas to pass through, the gas introduction structure for introducing outside air into the casing through the filter and the gas introduction hole or holes; a ceramic separator being placed so that a rear thereof enters the inside of the filter holding part in an axial direction of the oxygen sensing element and a front enters the inside of the casing and formed with a plurality of lead insertion holes axially penetrating the ceramic separator for inserting leads from the oxygen sensing element; and an elastic seal member being fitted elastically into a rear opening of the filter holding part and having seal lead insertion holes for inserting the leads for sealing a gap between outer faces of the leads and an inner face of the filter holding part; wherein an rear end face of the ceramic separator is positioned on the rear side behind the gas introduction hole in the axial direction and a predetermined gap is formed between the elastic seal member and the ceramic separator at least at the lead insertion position.

BRIEF DESCRIPTION OF THE DRAWINGS

In the accompanying drawings:

FIGS. 6A to 6C are schematic representations of a crimping method;

FIGS. 14A to 14E are schematic representations of an assembling process of the oxygen sensor in FIG. 1;

FIGS. 30A to 30C are conceptual drawings to describe a part of the effect of the oxygen sensor in FIG. 1 in comparison with a reference example;

FIGS. 35A and 35B are drawings to show a discrete state of a terminal metal shell in FIG. 34;

DETAILED DESCRIPTION OF THE INVENTION

Figure 1:
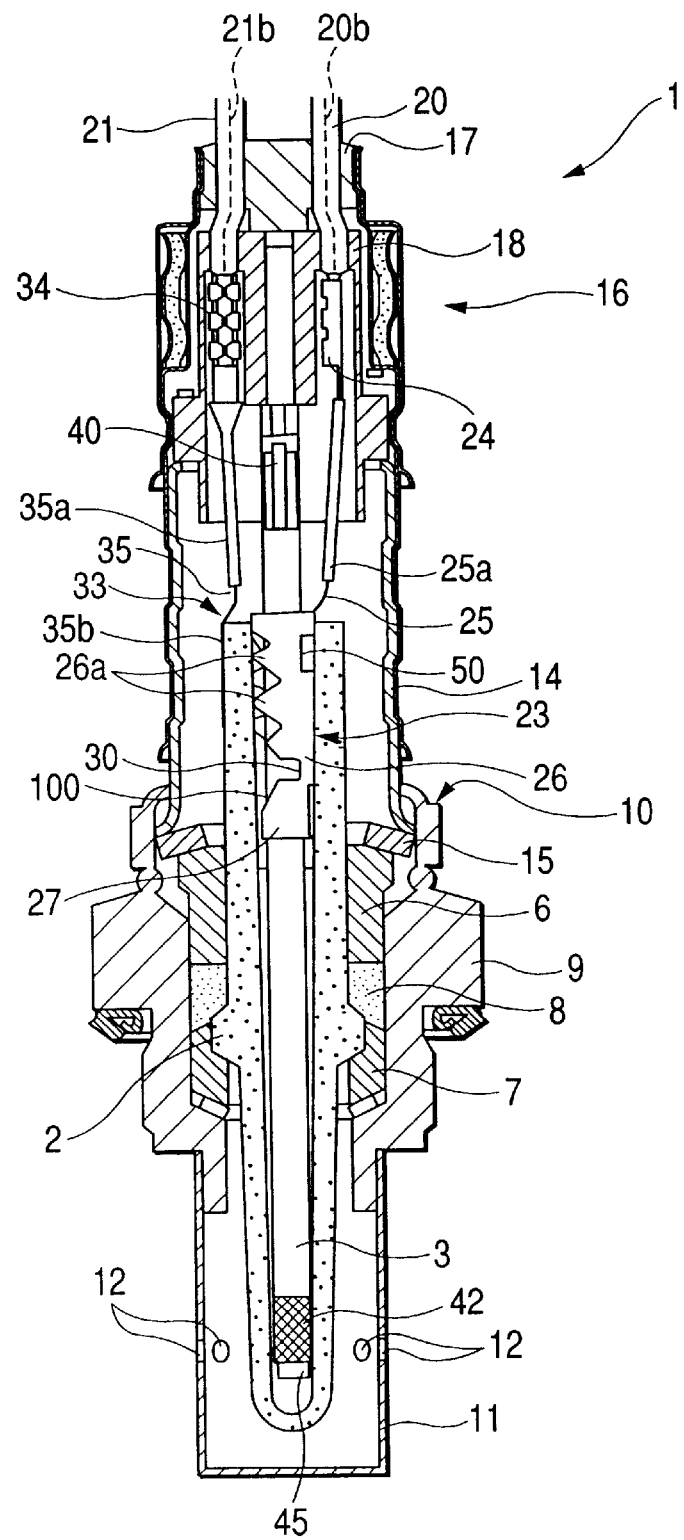
FIG. 1 is a longitudinal sectional view of an oxygen sensor as one embodiment of the invention.

Detailed description of the present invention will be described as follows.

An oxygen sensor of the invention is constituted by an oxygen sensing element shaped like a shaft, a cylindrical casing for housing the oxygen sensing element, and a gas introduction structure for introducing outside air into the casing. The gas introduction structure has a filter holding part making a cylindrical form almost coaxial with the casing on the rear of the casing, having an inside communicating with the inside of the casing, and being formed in a wall with one or more gas introduction holes and a filter being placed so as to block the gas introduction hole or holes of the filter holding part for rejecting permeation of liquid and allowing gas to pass through, for introducing outside air into the casing through the filter and the gas introduction hole or holes. The oxygen sensor further constituted by a ceramic separator being placed so that the rear thereof enters the inside of the filter holding part in the axial direction of the oxygen sensing element and the front enters the inside of the casing and formed with a plurality of lead insertion holes axially penetrating the ceramic separator for inserting leads from the oxygen sensing element and an elastic seal member being fitted elastically into a rear opening of the filter holding part and having seal lead insertion holes for inserting the leads for sealing the gap between the outer faces of the leads and the inner face of the filter holding part. The rear end face of the ceramic separator is positioned on the rear side behind the gas introduction hole in the axial direction and a predetermined gap is formed between the elastic seal member and the ceramic separator at least at the lead insertion position. Throughout the specification, the side toward the tip in the axial direction of the oxygen sensing element is assumed to be "front" and the side toward the opposite direction is assumed to be "rear."

According to the structure of the oxygen sensor, a predetermined gap is formed between the elastic seal member and the ceramic separator. Thus, for example, if they differ in pitch circle diameter of the lead insertion holes, the diameter difference is absorbed in the gap and the leads are hard to strongly bend and in turn damage to the leads, breaking of the leads, etc., is hard to occur at the sensor assembling time, etc. The filter for rejecting permeation of liquid and allowing gas to pass through is used to form a part of the gas introduction structure, so that water drops, etc., are prevented from entering the casing and outside air as a reference gas can be sufficiently introduced into the casing. The ceramic separator is placed so as to enter the filter holding part so that the rear end face is positioned behind the gas introduction holes. Thus, if an external strong shock is added to the gas introduction structure, the inside ceramic separator receives the shock, so that the filter holding part is prevented from becoming largely deformed and in turn a problem of impairing the filter sealability also becomes hard to occur. Further, the rear end face position of the ceramic separator is set behind the gas introduction hole. If water drops, etc., enter the gas introduction structure through the gas introduction hole, the ceramic sensor blocks the way of the water drops. Thus, the water drops, etc., become harder to flow into the casing. The reference gas flowing in through the gas introduction hole can be introduced into the casing through the ventilation groove and the through hole for ventilation without a hitch.

A water-proof and breathable filter made of a porous resin molded article of fluorine-family resin, such as polytetrafluoroethylene, can be used as the filter in the invention. Specifically, for example, a filter using a porous fiber structure provided by extending a polytetrafluoroethylene (PTFE) uncalcined molded article in a one-axis direction or directions of two or more axes at a heating temperature lower than the PTFE melting point (for example, Japanese Patent Publication Nos. Sho 42-13560, Sho 51-18991, Sho 56-45773, Sho 56-17216, Japanese Patent Laid-Open Nos. Sho 58-145735, Sho 59-152825, Hei 3-221541, Hei 7-126428, Hei 7-196831, etc., for example, Goretex (Japan Goretex (Kabu) as trade name) can be used.

In the structure of the oxygen sensor, the ceramic separator can be formed with a ventilation communication part axially penetrating the ceramic separator for introducing gas into the inside of the casing from the gap side in addition to the separator lead insertion holes, so that outside air as the reference gas introduced through the filter can be smoothly introduced into the casing from the rear end face side of the ceramic separator through the ventilation communication part. Thus, more stable oxygen sensor output can be provided.

Next, the oxygen sensing element can be formed like a hollow shaft with the tip closed and a shaft-like heating element for heating the oxygen sensing element can be placed in the hollow part. In this case, the ceramic separator can have the three or more separator lead insertion holes for inserting the leads from the oxygen sensing element and the heating element so that the centers of the lead insertion holes are positioned on a phantom circumferential path (separator pitch circle) and the elastic seal member can have the three or more seal lead insertion holes for inserting the leads from the oxygen sensing element and the heating element so that the centers of the lead insertion holes are positioned on a phantom circumferential path (seal pitch circle). The separator pitch circle and the seal pitch circle can be set so that the diameter of one is larger than that of the other.

Next, the elastic seal member can be formed on the front end face with a gap definition projection whose tip abuts the rear end face of the ceramic separator for defining the size of the gap. According to the structure, the elastic seal member abuts the ceramic separator in the gap definition projection, so that the ceramic separator can be fixed more stably. Since the gap to be formed can be determined automatically in response to the height of the gap definition projection, burdensome gap adjustment is not required and there is no fear of change in the gap size after the elastic seal member is fitted.

The gap definition projection can be formed in an area of the front end face of the elastic seal member, positioned inside the seal lead insertion holes arranged on the seal pitch circle. In this structure, the gap definition projection is formed almost at the center of the front end face of the elastic seal member, thus a stable abutment state against the ceramic separator can be provided and in turn a position shift, inclination, etc., in the axial direction of the elastic seal member is hard to occur. In this case, if the diameter of the separator pitch circle is larger than that of the seal pitch circle, the abutment area of the gap definition projection against the rear end face of the ceramic separator can be easily provided at a position surrounded by the separator lead insertion holes.

On the other hand, the elastic seal member may be formed in the rear end margin with a flange part projecting outward from the outer peripheral surface and may abut the rear end face of the filter holding part in the flange part, whereby the front end face position of the elastic seal member in the filter holding part, namely, the gap may be defined. In the structure, the elastic seal member is not formed with the gap definition projection. Thus, the structure is effective, for example, if the separator pitch circle diameter is small and a sufficient space for gap definition projection contact cannot be provided in an area surrounded by the separator lead insertion holes.

Referring now to the accompanying drawings, there are shown preferred embodiments of the invention.

An oxygen sensor 1 shown in FIG. 1 is formed of an oxygen sensing element 2 of a solid electrolyte member formed like a hollow shaft closed at the tip and a heating element 3 of a ceramic heater like a shaft; it is formed as an assembly of various members making up a crust of the oxygen sensing element 2 and the heating element 3. The oxygen sensing element 2 is made of a solid electrolyte having oxygen ion conductivity. $ZrO_2$ provided by solidly solving CaO or $Y_2O_3$ is representative as such a solid electrolyte. A solid solution of $ZrO_2$ and an oxide of any other alkali earth metal or rare earth metal may be used. $ZrO_2$ used as a base may contain $HfO_2$.

Figure 2:
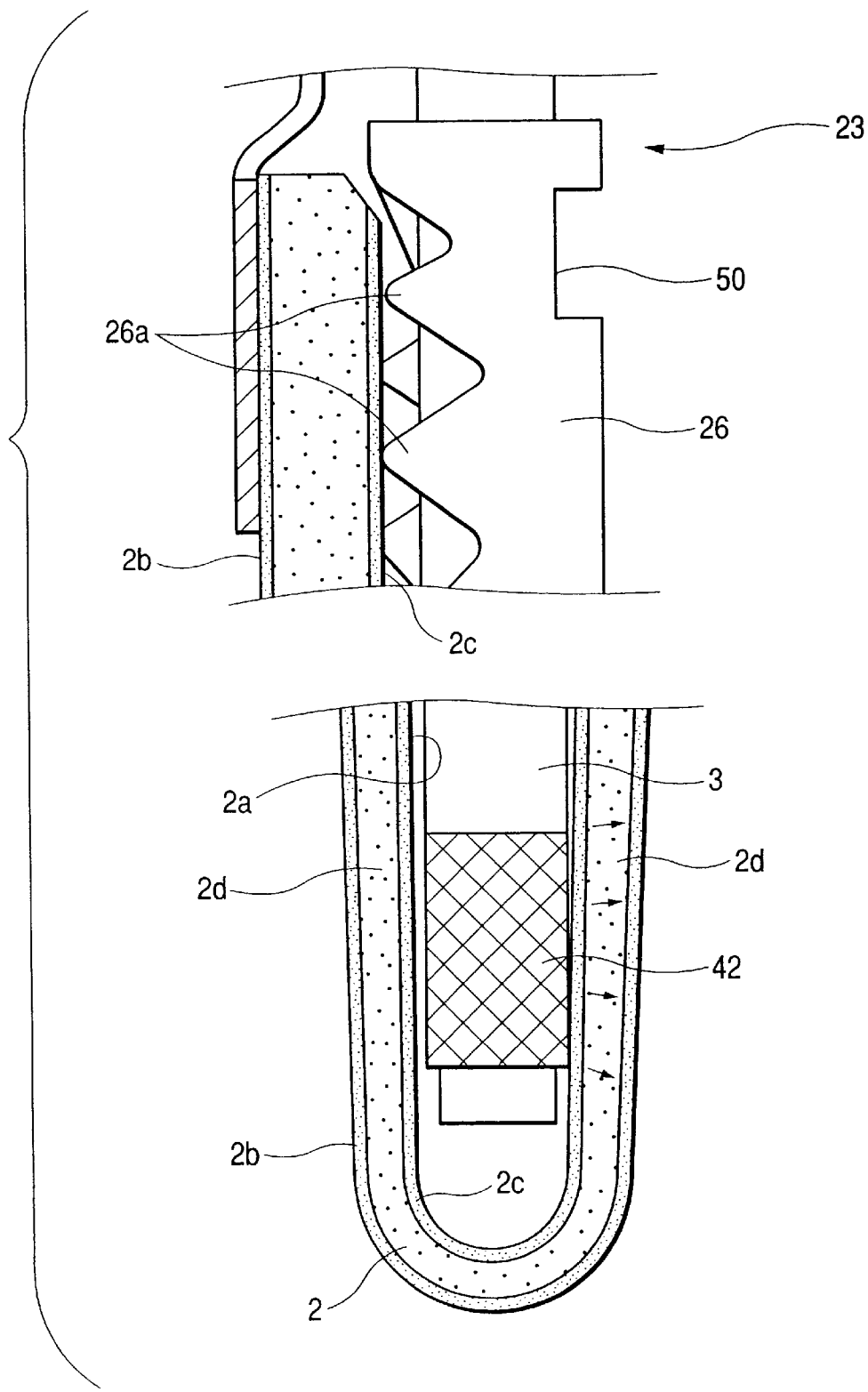
FIG. 2 is a sectional view of neighborhood of a contact part between a heating part and an oxygen sensing element in FIG. 1 on an enlarged scale.

The oxygen sensing element 2 is formed on the intermediate part outside with insulators 6 and 7 formed of insulating ceramics and a metal casing 10 via ceramic powder 8 formed of talc and pierces in a state in which it is electrically insulated from the casing 10. The casing 10 is constituted by a main body metal shell 9 having a screw part to attach the oxygen sensor 1 to an attachment part of an exhaust pipe, etc., and a main cylinder 14 connected so that the inside thereof communicates with one opening of the main body metal shell 9. As shown in FIG. 2, the oxygen sensing element 2 is formed on the inside and outside with a pair of electrode layers 2b and 2c so as to almost fully cover the inside and outside. The electrode layers 2b and 2c are formed as porous electrodes, such as Pt porous electrodes, each having a reversible catalyst function (oxygen dissociation function) for an oxygen molecule dissociation reaction to pour oxygen into the solid electrolyte forming the oxygen sensing element 2 and an oxygen rebonding reaction to cause oxygen to be released from the solid electrolyte.

Next, the main body metal shell 9 is formed in one opening with a protector 11 so as to cover the tip of the oxygen sensing element 2 in a predetermined space therebetween and the protector 11 is formed with gas permeation ports 12 for allowing exhaust gas to pass through, whereby oxygen in the exhaust gas can come in contact with the tip surface of the oxygen sensing element 2. In an opposite opening of the main body metal shell 9, the main cylinder 14 is crimped via a ring 15 between the main cylinder 14 and the insulator 6 and furthermore, a filter assembly 16 (gas introduction structure) shaped like a hollow cylinder as a whole is fitted into the main cylinder 14 from the outside. An opening of the filter assembly 16 at the upper end in the figure is sealed with an elastic seal member 17 made of rubber, etc. A ceramic separator 18 is placed furthermore inward. Leads 20 and 21 for the oxygen sensing element 2 and leads 28 and 29 (in FIG. 21 (hidden by the leads 20 and 21 in FIG. 1)) for the heating element 3 are placed so as to penetrate the ceramic separator 18 and the elastic seal member 17.

The lead 20 for the oxygen sensing element 2 is electrically connected to the inner electrode layer 2c (FIG. 2) of the oxygen sensing element 2 through a connector part 24 of a terminal metal shell 23, a leader line part 25 (covered with an insulating tube 25a, which may be omitted) following the connector part 24, and an internal electrode connection part 26 of the terminal metal shell 23. On the other hand, the lead 21 is electrically connected to an outer electrode layer (not shown) of the oxygen sensing element 2 through a connector part 34 of a terminal metal shell 33, a leader line part 35 following the connector part 34, and an external electrode connection part 35b. A pair of positive and negative heater terminal parts 40 for energizing the heating element 3 is fixed to a base end part (upper end part in FIG. 1) of the heating element 3 and a heating resistance circuit (described later) buried in the heating element 3 is energized through the heater terminal parts 40. The leads 28 and 29 for the heating element 3 are connected to the heater terminal parts 40.

Next, the structure of the filter assembly 16 will be discussed in detail. Throughout the specification, the side toward the tip in the axial direction of the oxygen sensing element 2 (closed side) is assumed to be "front" and the side toward the opposite direction is assumed to be "rear."

Figure 3:
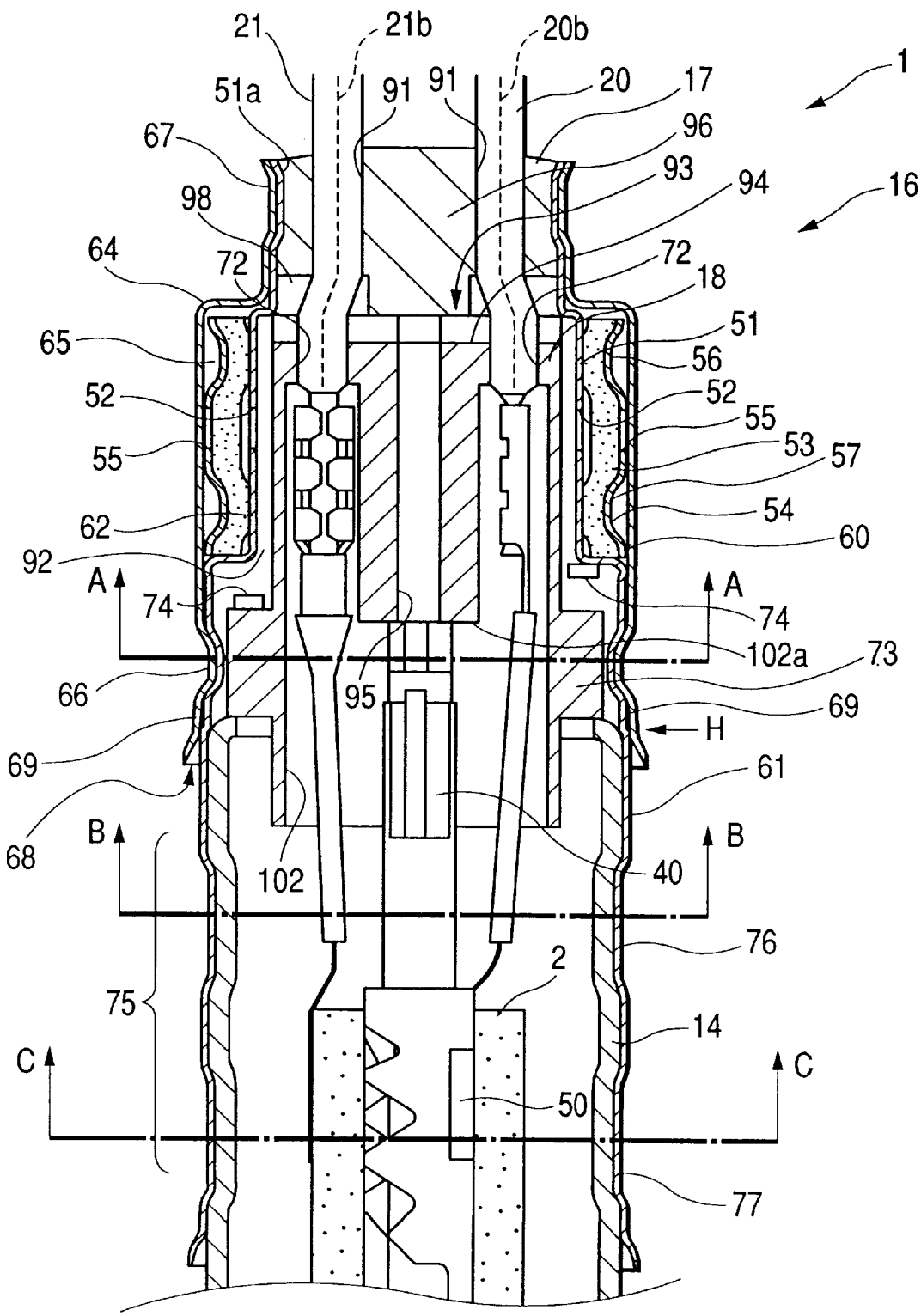
FIG. 3 is a sectional view of the main part in FIG. 1 on an enlarged scale.

As shown in FIG. 3, the filter assembly 16 is made of a filter holding part 51 making a cylindrical form almost coaxially coupled to the main cylinder 14 (casing 10) from the rear outside, having an inside communicating with the inside of the main cylinder 14, and being formed in a wall with gas introduction holes 52. A cylindrical filter 53 for blocking the gas introduction holes 52 is placed on the outside of the filter holding part 51. Further, placed on the outside of the filter 53 is a cylindrical auxiliary filter holding part 54 formed in a wall with one or more auxiliary gas introduction holes 55, the filter 53 being sandwiched between the auxiliary filter holding part 54 and the filter holding part 51. Specifically, the gas introduction holes 52 and the auxiliary gas introduction holes 55 are made with a predetermined spacing along the circumferential direction in positional relation corresponding to each other in the axial intermediate part with respect to the filter holding part 51 and the auxiliary filter holding part 54 and the filter 53 is placed so as to surround the filter holding part 51 in the circumferential direction.

The filter holding part 51 is made of a first portion 61 in the axial front and a second portion 62 in the axial rear relative to a stepped part 60 formed in the axial intermediate part of the filter holding part 51 with the second portion 62 being smaller in diameter than the first portion 61. The gas introduction holes 52 are made in the walls of the second portion 62. Further, the auxiliary filter holding part 54 has an inner diameter smaller than the outer diameter of the first portion 61 of the filter holding part 51.

Here, the filter 53 is made of a porous fiber structure provided by extending a polytetrafluoroethylene (PTFE) uncalcined molded article in a one-axis direction or directions of two or more axes at a heating temperature lower than the PTFE melting point (for example, Goretex (Japan Goretex (Kabu) as trade name), for example, as a water repellent filter for rejecting permeation of liquid with water of water drops, etc., as the main component and allowing gases of air, water vapor, etc., to pass through, whereby air (outside air) as a reference gas is introduced into the main cylinder 14 (casing 10) through the auxiliary gas introduction holes 55, the filter 53, and the gas introduction holes 52 and the entry of water in a liquid state such as water drops is blocked.

Figure 4A:
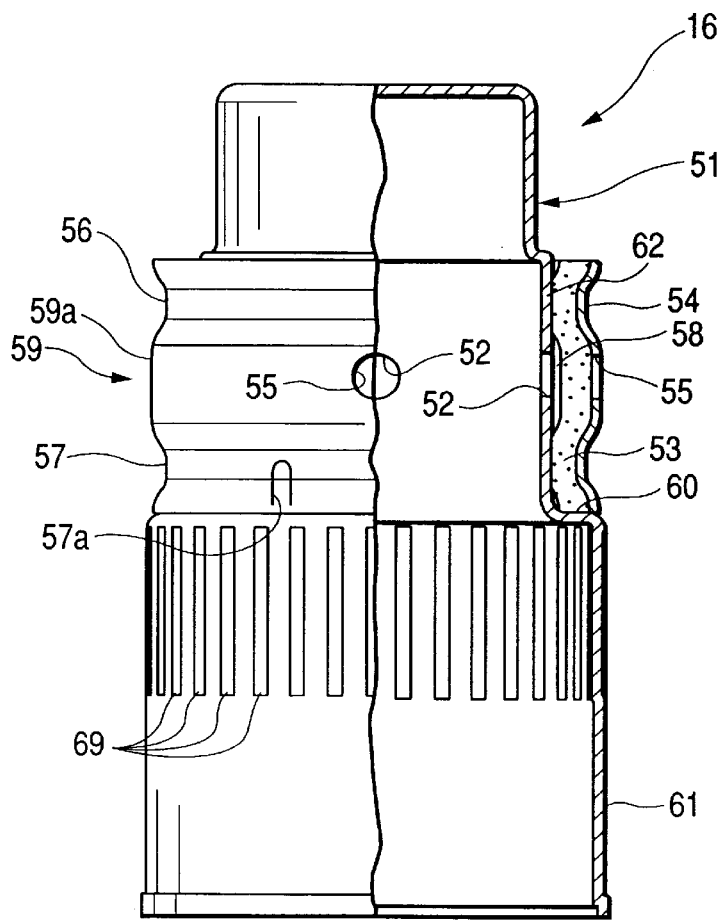
FIGS. 4A to 4E are fragmentary frontal sectional views of a filter assembly.
Figure 4B:
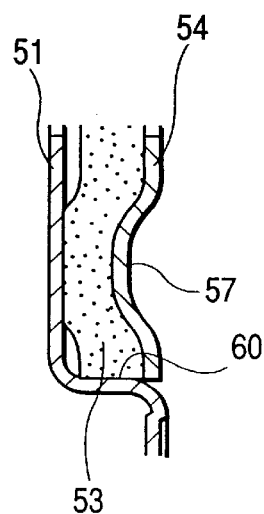
Figure 4C:
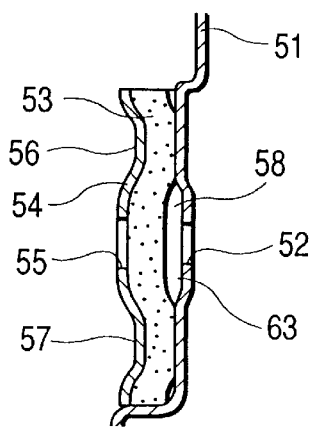

As shown in FIGS. 4A to 4C, the filter 53 adheres closely to the inner face of the auxiliary filter holding part 54 and a predetermined gap 58 is made so as to form an annular form along the row of the auxiliary gas introduction holes 55, for example, between the outer face of the filter holding part 51 and the filter 53. Further, the auxiliary filter holding part 54 is formed with annular filter crimp parts 56 and 57 for coupling the auxiliary filter holding part 54 to the filter holding part 51 via the filter 53 on both sides of the axial direction with the row of the auxiliary gas introduction holes 55 arranged in the circumferential direction between.

Here, the auxiliary filter holding part 54 is placed so that the axial rear margin thereof is positioned corresponding to the rear margin of the filter 53, and the filter crimp part 56 is formed in the circumferential direction along the rear margin, whereby the filter 53 can be visually checked through an opening of an annular gap made between the auxiliary filter holding part 54 and the filter holding part 51 (as a filter check part) at the rear end face position of the auxiliary filter holding part 54. For example, as shown in FIGS. 5A to 5D, when the cylindrical filter 53 is fitted around the outside of the filter holding part 51 and further the auxiliary filter holding part 54 is fitted around the outside of the filter 53, the filter 53 can move in association with the auxiliary filter holding part 54, causing a position shift. In this case, if the filter crimp part 56 is formed, the filter 53 is detached from the filter crimp part 56 and sealing becomes incomplete. However, such a crimp failure of the filter 53 can be easily found because the filter 53 can be visually checked as described above.

As shown in FIG. 4A, the filter crimp part 57 in the front margin of the auxiliary filter holding part 54 can also be formed with a filter check exposure part 57a for exposing the filter 53 partially. In doing so, whether or not the filter is normally crimped can also be determined easily in the front end margin of the auxiliary filter holding part 54.

Next, the portion positioned between the filter crimp parts 56 and 57 of the auxiliary filter holding part 54 is a form outward bending and convexly swelling together with the filter 53, thereby forming an annular convex part 59. The tip of the annular convex part 59 is flattened annularly. The auxiliary gas introduction hole 55 is made in the flattened part 59a and as the flattened part 59a is formed, the filter holding part 51 is pressed against the filter 53 and adheres closely thereto.

With such a structure, distribution resistance of outside air passing through the filter 53 is lessened because the annular gap 58 is made inside, and the outside air can be smoothly introduced into the main cylinder 14 through the gas introduction holes 52. On the other hand, the outer face of the filter 53 adheres closely to the inner face of the auxiliary filter holding part 54, thus dust, oil, water drops, etc., do not enter the space between the filter 53 and the auxiliary filter holding part 54 easily through the auxiliary gas introduction hole 55 and in turn degradation of oil or water repellency on the outer face of the filter 53 is stopped or suppressed, always providing good ventilation. Thus, for example, if the reference gas temperature becomes high, sensor output degradation does not occur as easily as in conventional devices.

Figure 5A:
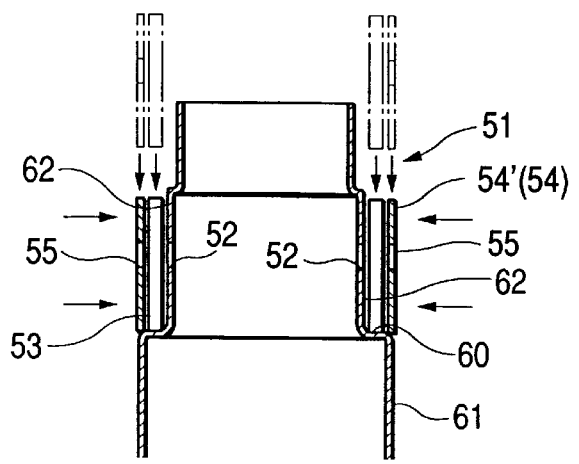
FIGS. 5A to 5D are schematic representations of an assembling process of the filter assembly.
Figure 5B:
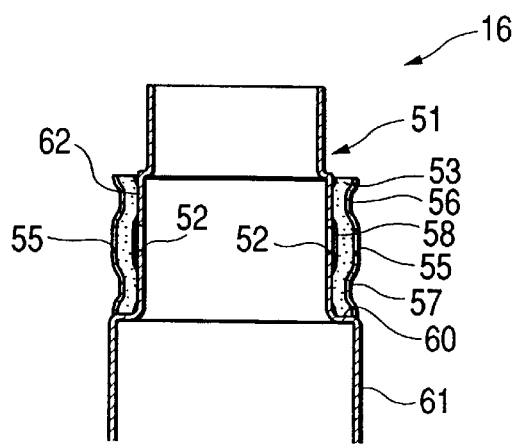
Figure 5C:
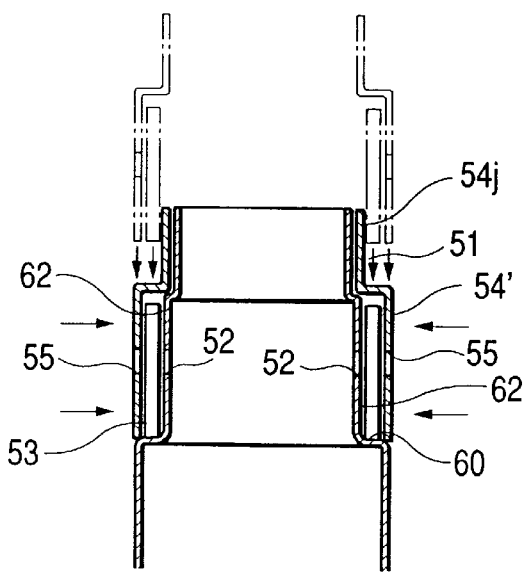
Figure 5D:
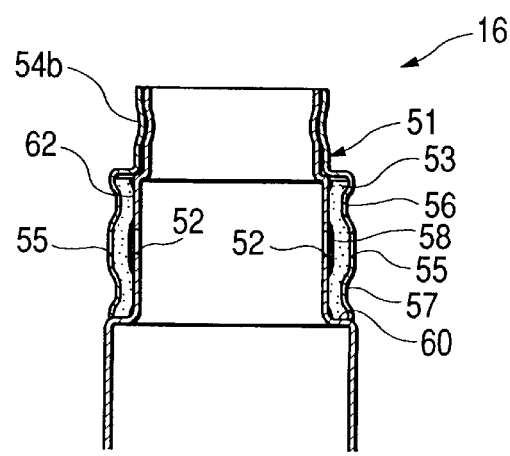

The filter assembly 16 having the structure can be manufactured, for example, by the following method: First, as shown in FIG. 5A, the cylindrical filter 53 is fitted into the outside of the filter holding part 51 and further a cylindrical member 54' to become the auxiliary filter holding part 54 is put on the outside of the filter 53. The stepped part 60 formed in the filter holding part 51 supports the lower margins of the filter 53 and the cylindrical member 54' and prevents them from coming out. Subsequently, as shown in FIG. 5B, the cylindrical member 54' is crimped in the circumferential direction toward the filter part on both sides of the row of the auxiliary gas introduction holes 55, thereby forming the filter crimp parts 56 and 57. As shown in FIGS. 5C and 5D, the auxiliary filter holding part 54 may be projected to the front from the filter 53 and the projection may be formed as a small-diameter part 54j, then a crimp part 54b may be formed in the small-diameter part 54j, whereby when a twist force is applied to the auxiliary filter holding part 54, the turn stop effect can be improved furthermore.

As shown in FIGS. 6A to 6C, the filter crimp parts 56 and 57 can be formed by compressing the auxiliary filter holding part 54 axially using crimp punches placed along the circumferential direction of the auxiliary filter holding part 54. The inner peripheral surfaces of the crimp punches 151 are combined to form a cylinder face corresponding to the outer peripheral surface of the auxiliary filter holding part 54 and can be moved toward and away from the outer peripheral surface of the auxiliary filter holding part 54 separately; they are moved to the auxiliary filter holding part 54 all in unison by a punch drive (not shown) and compress the auxiliary filter holding part 54. Convex stripe parts 152 and 153 are formed in both axial margins of each crimp punch 151 and are pressed against the outer peripheral surface of the auxiliary filter holding part 54, forming arc-shaped concave parts, which are combined in the circumferential direction to form the filter crimp parts 56 and 57.

The portion sandwiched between the convex stripe parts 152 and 153 of the crimp punch 151 is a concave part 154 having a flat bottom 154a (flat member) and a depth h of the concave part 154 is set smaller than the total thickness of the filter 53 and the auxiliary filter holding part 54. When the auxiliary filter holding part 54 is compressed by the crimp punches 151, the convex stripe parts 152 and 153 dig, forming the filter crimp parts 56 and 57; on the other hand, the portion sandwiched between the crimp parts 56 and 57 bends outward, forming a convex part 59. However, when compression develops to some extent, the convex part 59 strikes against the bottom 154a of the concave part 154 and is stopped. When compression is furthermore continued, the convex part 59 is shaped by the concave part 154 and the flattened part 59a is formed corresponding to the flat bottom of the concave part 154.

At this time, the auxiliary filter holding part 54 is compressed and deformed comparatively largely with crimping and the bend amount in the convex part 59 becomes large, but the inner filter holding part 51 is not much compressed and the bend amount is also small. On the other hand, the filter 53, which is flexible, follows the auxiliary filter holding part 54 and bends outward. Resultantly, the annular gap 58 is made between the filter holding part 51 and the filter 53 based on the bend amount difference between the filter holding part 51 and the auxiliary filter holding part 54.

Figure 4D:
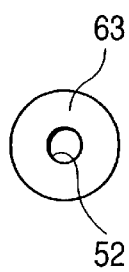
Figure 4E:
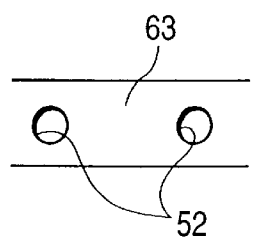

As shown in FIG. 4C, the filter holding part 51 may be formed with a concave part 63 dented inward at least in the surroundings of the gas introduction hole 52 and the gap 58 may be made between the filter holding part 51 and the filter 53 in the concave part 63. In this case, the concave part 63 may be formed like a dimple provided by denting the periphery of the gas introduction hole 52 as shown in FIG. 4D or like a ring along the arrangement direction of the gas introduction holes 52 as shown in FIG. 4E.

Referring again to FIG. 3, the ceramic separator 18 is formed with separator lead insertion holes (lead insertion holes) 72 penetrating axially the ceramic separator 18 for inserting the leads 20 and 21 and is formed at an axial intermediate position with a flange-like separator support part 73 projected from the outer peripheral surface. The ceramic separator 18 is placed so as to abut the rear end face of the main cylinder 14 in the separator support part 13 in a state in which a portion positioned ahead the separator support part 73 is entered in the rear end inside, and is placed in a state in which a portion positioned behind the separator support part 73 is projected to the outside of the main cylinder 14. The ceramic separator 18 will be discussed later in detail.

A cylindrical protective cover 64 is placed on the outside of the auxiliary filter holding part 54 so as to cover the holding part 54. It blocks or suppresses a direct jet of liquid drops to the filter 53 or deposition of deposits of oil, dirt, etc. The protective cover 64 is placed so as to produce a gas retention space 65 between the protective cover 64 and the filter 53 at a position corresponding to the gas introduction hole 52 (or the auxiliary gas introduction hole 55), for example, and both sides between which the gas introduction hole 52 is sandwiched axially are joined by crimp parts 66 and 67 as cover joint parts to the outer face of the filter holding part 51. An external communication part 68 for allowing the gas retention space 65 to communicate with the outside and introducing outside air into the gas retention space 65 is formed between the protective cover 64 and the filter holding part 51 at a position corresponding to the axially front crimp part 66.

Figure 7:
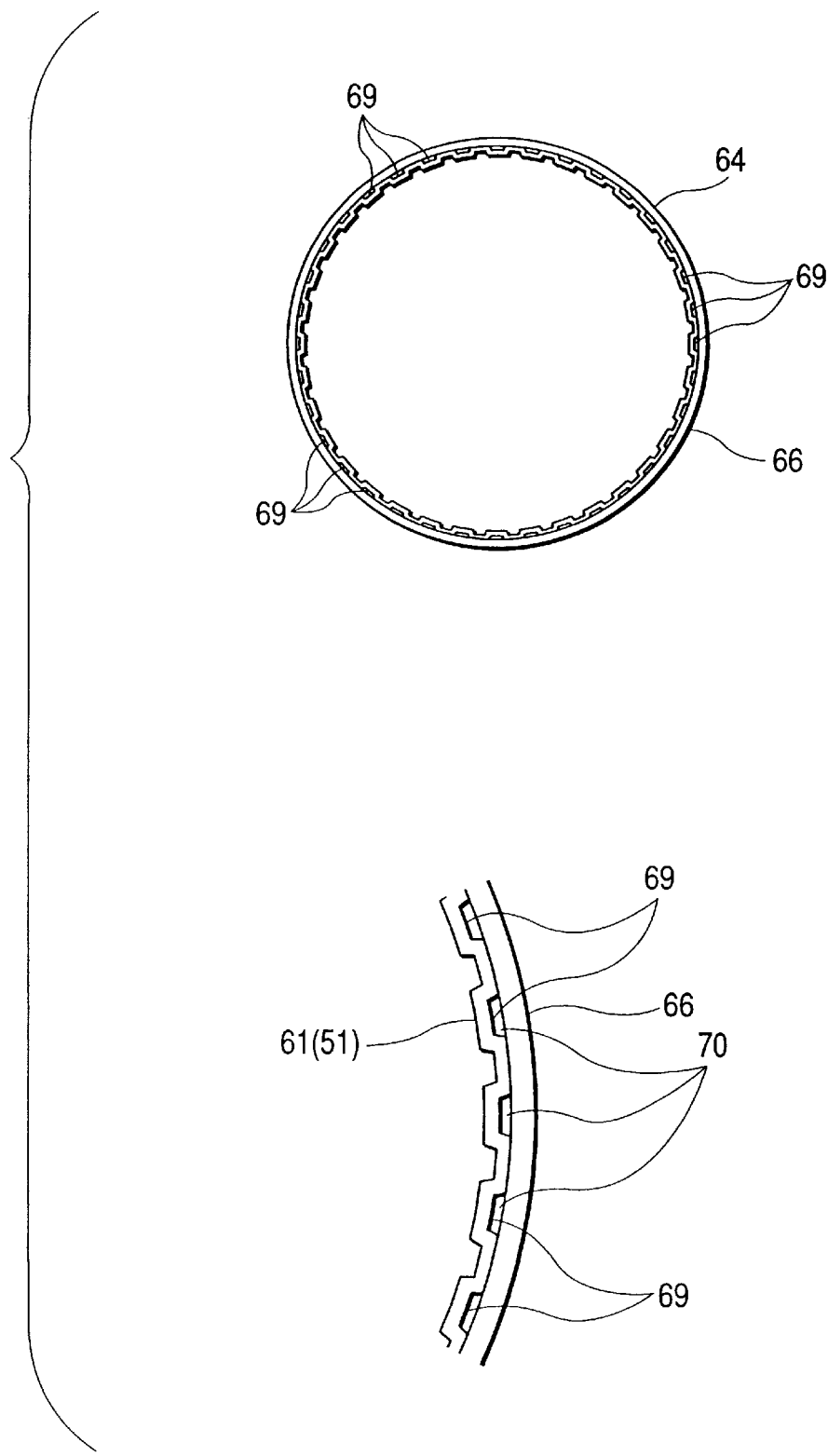
FIG. 7 is a sectional plan view of a crimp part between the filter assembly and a protective cover and its partially enlarged view.

Specifically, as shown in FIGS. 4A to 4C, grooves 69 extending in the axial direction of the filter holding part 51 are formed on the outer peripheral surface of the first portion 61 of the filter holding part 51 with a predetermined spacing along the circumferential direction and make up the external communication part 68. As shown in FIG. 7, the protective cover 64 is crimped toward the first portion 61 of the filter holding part 51 (FIG. 3, etc.,), whereby the crimp part 66 is formed in an annular shape so as to cross the grooves 69 in the arrangement direction thereof and leave a gap 70 between the protective cover 64 and the first portion 61 at the bottom of each groove 69. The crimp part 66 is formed at a position corresponding to the outer peripheral surface of the separator support part 73 of the ceramic separator 18, whereby the separator support part 73 can receive a compression force at the crimp part formation time, thus the crimp part 66 can be formed reliably.

Figure 8:
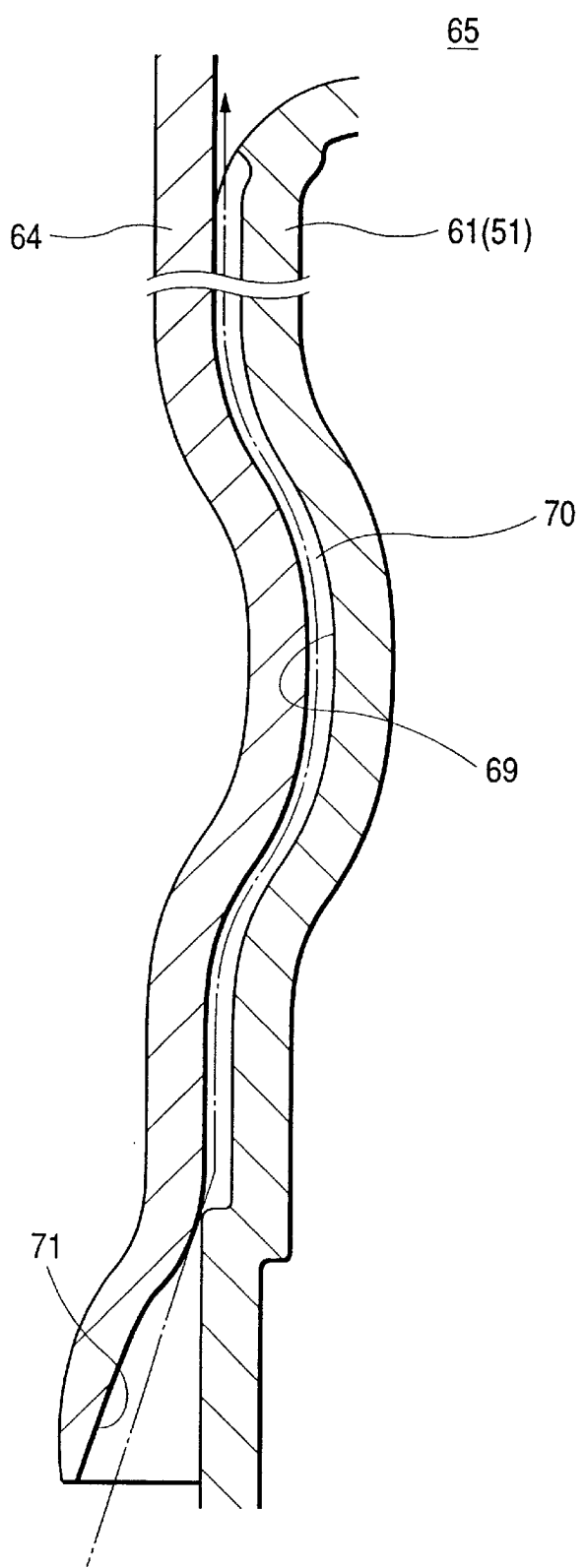
FIG. 8 is a partially enlarged longitudinal sectional view.
Figure 9:
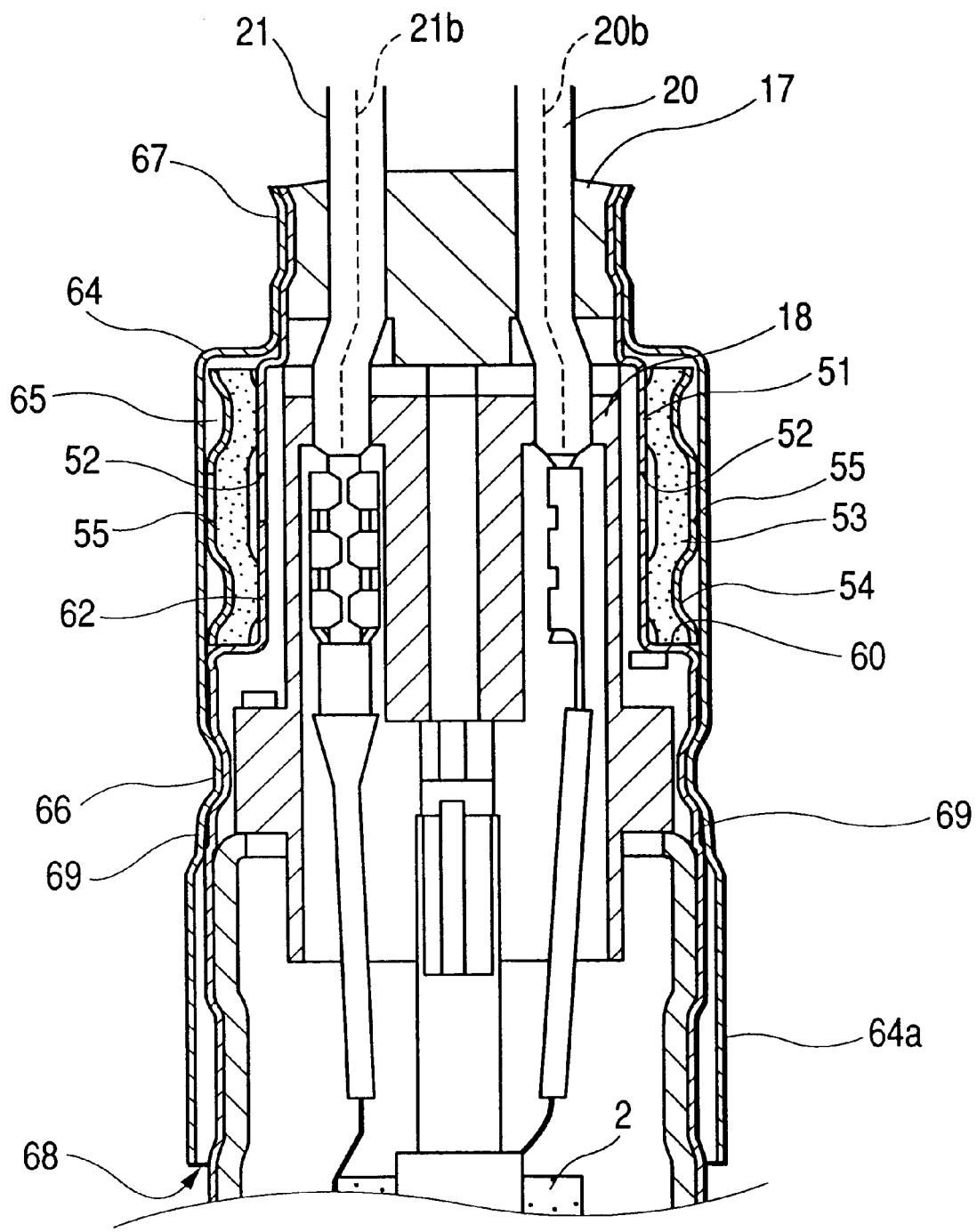
FIG. 9 is a longitudinal sectional view of a structure in which the front end of the protective cover is extended.

In the described structure, as shown in FIG. 8, outside air is introduced into the gas retention space 65 through the gaps 70 formed in the grooves 69 from front openings 71 of the gaps 70 between the protective cover 64 and the first portion 61 of the filter holding part 51. On the other hand, the crimp part 67 is formed on the outer peripheral surface of the end part of the second portion 62 of the filter holding part 51 (FIG. 3, etc.,). As shown in FIG. 9, an axial front margin 64a of the protective cover 64 may be extended like a skirt by a predetermined length from the end of the groove 69, whereby the probability that if the oxygen sensor 1 is caught in a splash, etc., water drops, etc., enter the gas retention space 65 from the inside of the protective cover 64 can be lowered furthermore.

Figure 45:
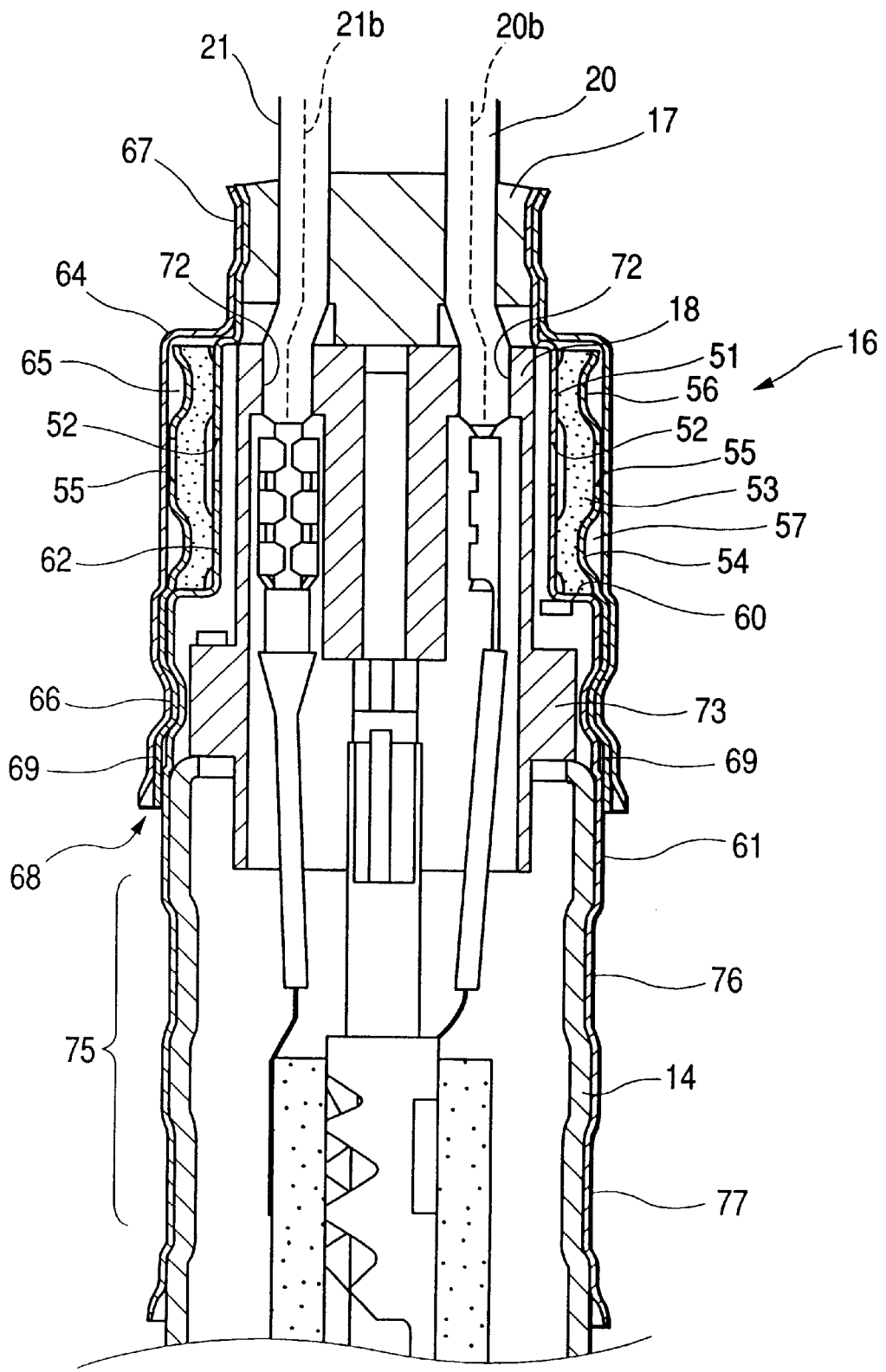
FIG. 45 is a longitudinal sectional view to show an example of forming an auxiliary filter holding part so as to spread across a stepped part of a filter holding part.

Here, as shown in FIG. 45, the front of the auxiliary filter holding part 54 may be extended axially so that the auxiliary filter holding part 54 spreads across the first portion 61 and the second portion 62. In this case, the auxiliary filter holding part 54 is crimped directly toward the first portion 61 at a position corresponding to the first portion 61, whereby an annular auxiliary crimp part 66 may be formed along the circumferential direction of the first portion 61. In doing so, the filter holding part 51 can be fixed to the auxiliary filter holding part 54 more reliably. The front margin of the protective cover 64 can be extended to a position overlapping the margin corresponding to the auxiliary filter holding part 54 and the crimp part 66 as a cover joint part can also be used as the auxiliary crimp part. In this case, the external communication part 68, namely, the grooves 69 can be formed in the auxiliary filter holding part 54.

Figure 10:
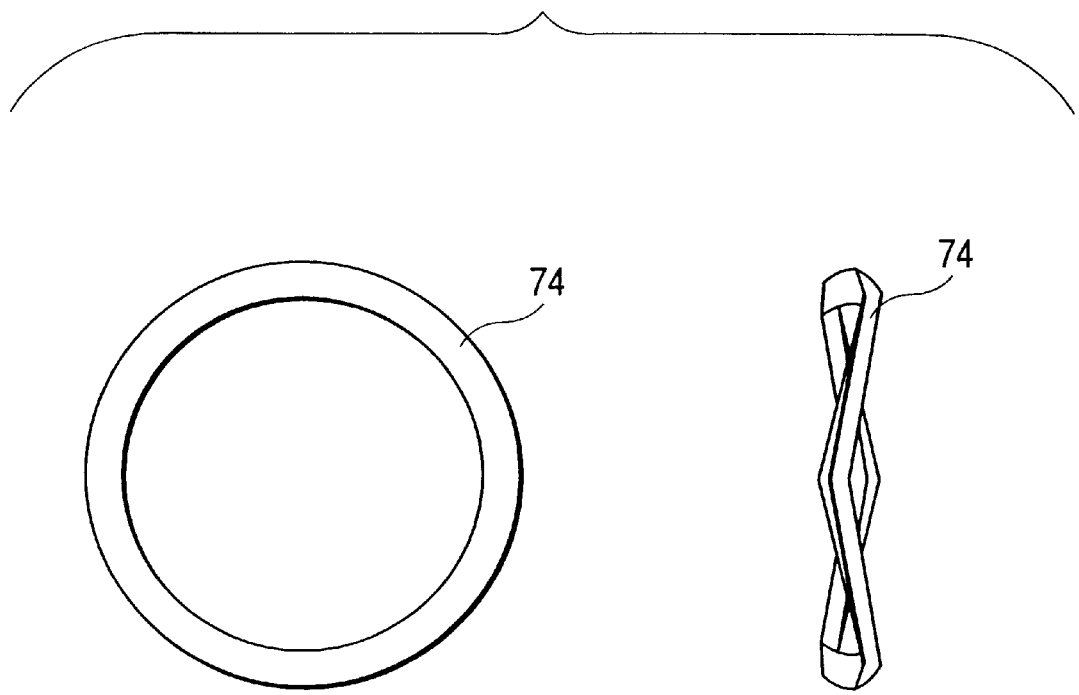
FIG. 10 is an illustration to show an example of a metal elastic member.

Referring again to FIG. 3, the filter holding part 51 of the filter assembly 16 is placed so as to allow the projection of the ceramic separator 18 to approach the inside of the second portion and cover it and so as to abut the separator support part 73 at the stepped part 60 via a metal elastic member 74. The metal elastic member 74 is formed as a spring washer, such as a wave washer as shown in FIG. 10. As shown in FIG. 3, it is inserted into the separator support part 73 and is placed in compression, whereby the metal elastic member 74 produces a proper sandwich holding force on the ceramic separator 18 between the filter assembly 16 (cover member) and the main cylinder 14 for preventing a rattle and fixing and holding the ceramic separator 18 more reliably. It also suppresses an excessive sandwich force acting on the separator support part 73 of the ceramic separator 18 because of elastic deformation of the metal elastic member when the oxygen sensor 1 is assembled, etc., and in turn prevents the ceramic separator 18 from being broken or chipped accordingly. The metal elastic member 74, which is made of metal, is excellent in heat resistance and can well maintain the ceramic separator rattle prevention effect over a long term.

The filter holding part 51 is placed so as to overlap the main cylinder 14 from the outside thereof at the tip, namely, in the first portion 61 and at the overlap, the filter holding part 51 is crimped toward the main cylinder 14, whereby an annular assembly coupling crimp part 75 is formed as a coupling part in the circumferential direction. The assembly coupling crimp part 75 causes the filter holding part 51 to be pressed against and coupled to the main cylinder 14 so that the inner peripheral surface of the filter holding part 51 becomes hermetic relative to the outer peripheral surface of the main cylinder 14.

Figure 11:
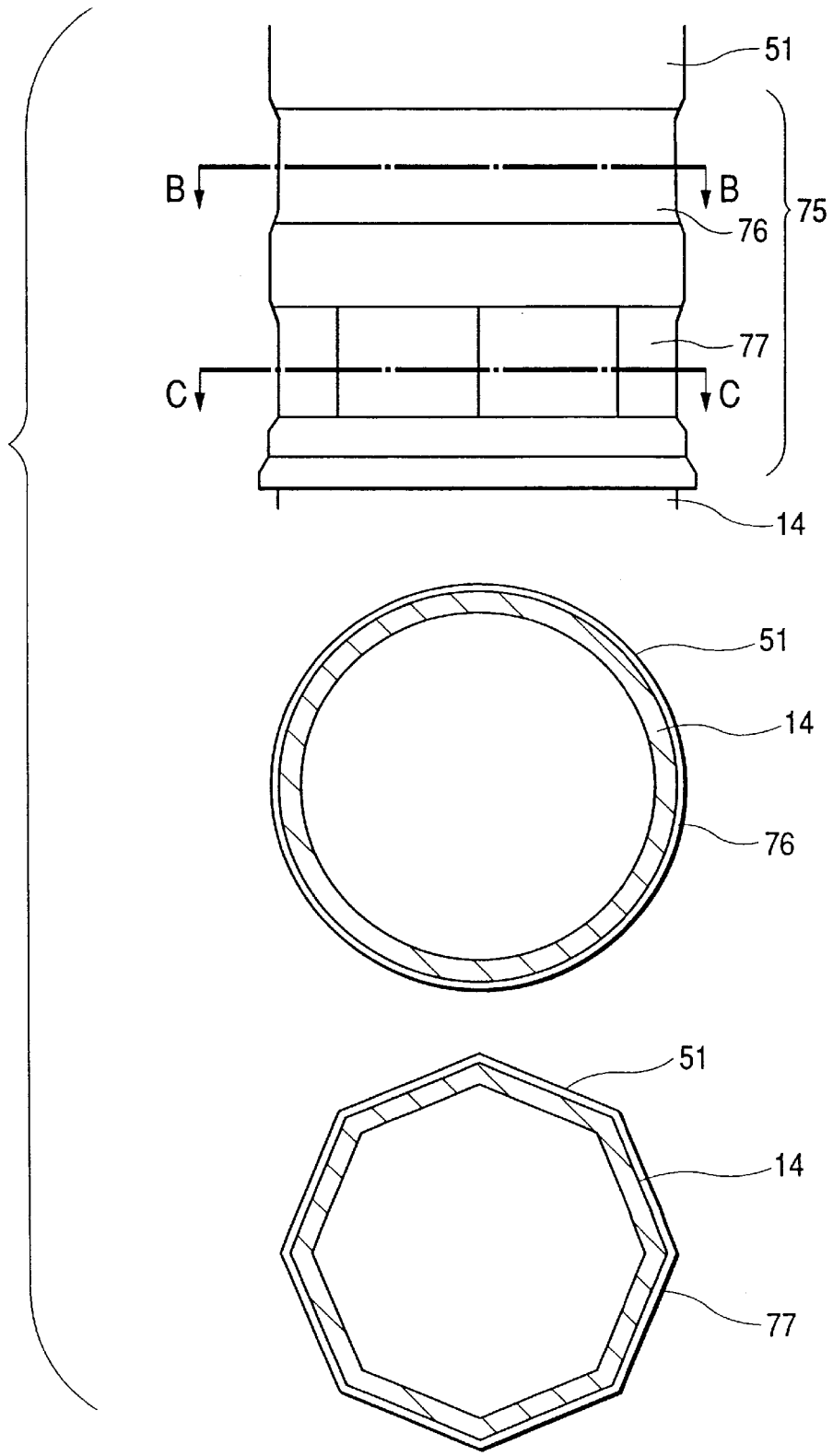
FIG. 11 is an enlarged view of an assembly coupling crimp part and sectional views taken on line B—B and line C—C in the figure.

As shown in FIG. 11, the assembly coupling crimp part 75 consists of a main crimp part 76 formed annularly in the circumferential direction by crimping the filter holding part 51 toward the main cylinder 14 and an auxiliary crimp part (rotation prevention part) 77 angular in cross section (octagonal in cross section in the embodiment) formed on the side near to the tip of the oxygen sensing element 2 rather than the main crimp part 76.

Figure 12A:
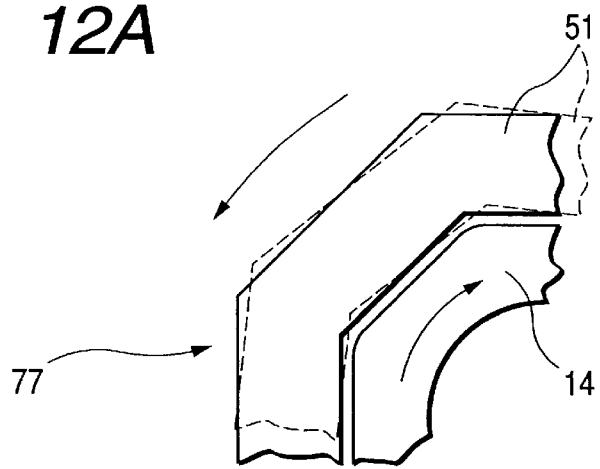
FIGS. 12A and 12B are schematic representations of the effects of a main crimp part and an auxiliary crimp part in the assembly coupling crimp part.
Figure 12B:
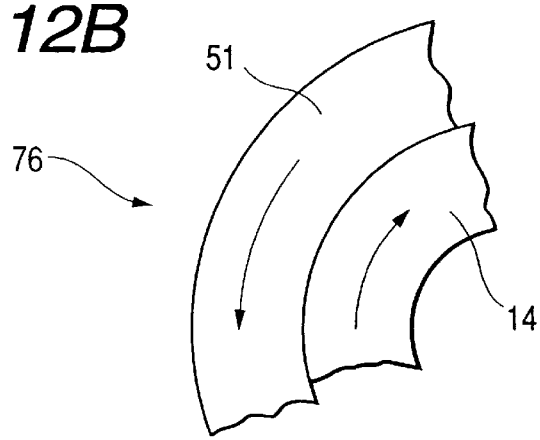

In the main crimp part 76, the contact face between the main cylinder 14 and the filter holding part 51 becomes cylindrical, thus excellent hermeticity is provided and water, etc., can be reliably prevented from leaking into the main cylinder 14 from the space between the main cylinder 14 and the filter holding part 51. However, as shown in FIG. 12B schematically, if a strong twist force acts on the main cylinder 14 and the filter holding part 51 because of external shock, etc., there can be a possibility that a slip may occur because of relative rotation between the main cylinder 14 and the filter holding part 51 on the cylindrical contact face, impairing hermeticity. Then, if the auxiliary crimp part 77 as described above is formed, its contact face is shaped like an angular cylinder as shown in FIG. 12A. Thus, if a twist force as described above acts, relative rotation between the main cylinder 14 and the filter holding part 51 does not usually occur. Accordingly, such relative rotation can be effectively prevented from occurring also in the main crimp part 76 and the hermeticity between the main cylinder 14 and the filter holding part 51 can be made more reliable. The main crimp part 76 and the auxiliary crimp part 77 may be formed by interchanging them in axial positional relationship. However, since the tip of the oxygen sensor 1 can be exposed to high temperature, the positional relationship in which the main crimp part 76 where hermeticity is prioritized is away from such a heat source is more desirable.

Figure 13:
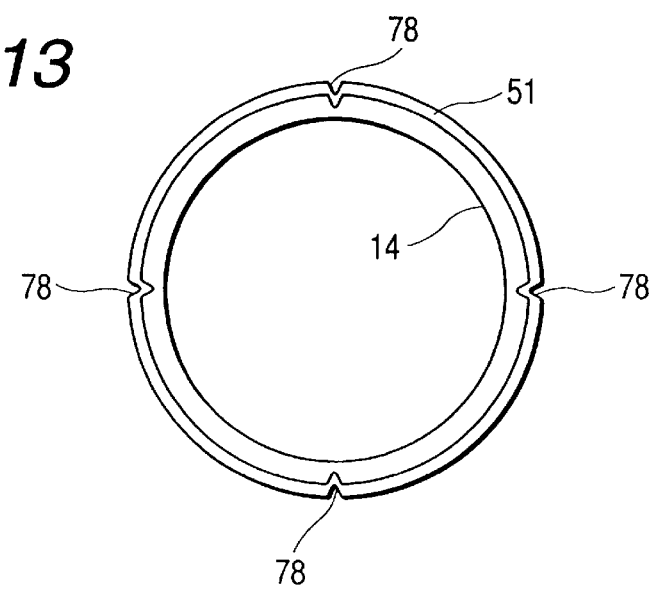
FIG. 13 is a sectional plan view to show a modified example of a rotation prevention part.

In addition to the auxiliary crimp part 77, formation of dig parts 78 digging from the filter holding part 51 to the main cylinder 14 with a predetermined spacing along the circumferential direction, for example, as shown in FIG. 13 can also function as a rotation prevention part. On the other hand, if it is little feared that relative rotation as described above will occur in the main crimp part 76, the auxiliary crimp part 77 can also be omitted. An annular weld part may be formed along the circumferential direction, for example, by laser welding, etc., as a coupling part between the filter holding part 51land the main cylinder 14.

A method of fitting the filter assembly 16 into the main cylinder 14 will be discussed. That is, as shown in FIG. 14A, the metal elastic member 74 is inserted into the ceramic separator 18 and further the front end of the ceramic separator 18 is inserted into the main cylinder 14. On the other hand, the filter assembly 16 is previously assembled as shown in FIG. 5 and is put from the outside of the ceramic separator 18 and the main cylinder 14 in the filter holding part 51, as shown in FIG. 14a. The oxygen sensing element 2, the heating element 3, and the like (FIG. 1) are previously fitted into the main cylinder 14 and the leads 20, 21, 28, and 29 (FIG. 21) from the oxygen sensing element 2 and the heating element 3 are passed through the lead insertion holes 72 (FIG. 3) of the ceramic separator 18 and further are extended to the outside from the rear end opening of the filter holding part 51.

Subsequently, as shown in FIG. 14B, an axial compression force is applied to the main cylinder 14 and the filter assembly 16, whereby the metal elastic member 74 is compressed and deformed between the filter holding part 51 and the separator support part 73 of the ceramic separator 18 and generates an urging force for sandwiching the ceramic separator 18 between the main cylinder 14 and the filter holding part 51. With this state maintained, the assembly coupling crimp part 75 is formed in the filter holding part 51 and the main cylinder 14 as shown in FIG. 14C and the filter holding part 51 and the main cylinder 14 are joined. Next, as shown in FIG. 14D, the elastic seal member 17 is fitted into the rear end opening of the filter holding part 51, the protective cover 64 is put, and as shown in FIG. 14E, the crimp parts 66 and 67 are formed. The assembling is now complete.

According to this method, the filter assembly 16 is assembled independently of fitting of the oxygen sensing element 2, etc., into the casing 10, thus the leads do not become obstruction and the assembling work can be carried out extremely efficiently. Since fitting of parts into the casing 10 can be performed in parallel with assembling of the filter assembly 16, productivity improves dramatically. Further, even if a fitting failure, etc., of the filter 53 occurs, if it can be found at the stage of the filter assembly 16, the failure does not affect the sensor finished product and waste, etc., of parts is hard to occur.

Figure 15A:
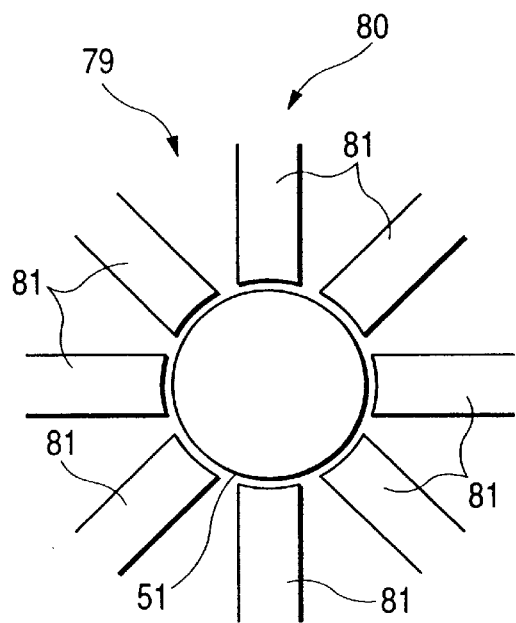
FIGS. 15A to 15C are a conceptual drawings of a crimping device.
Figure 15B:
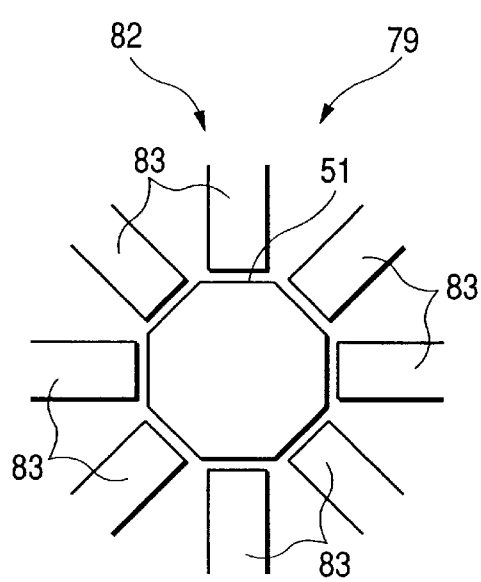
Figure 15C:
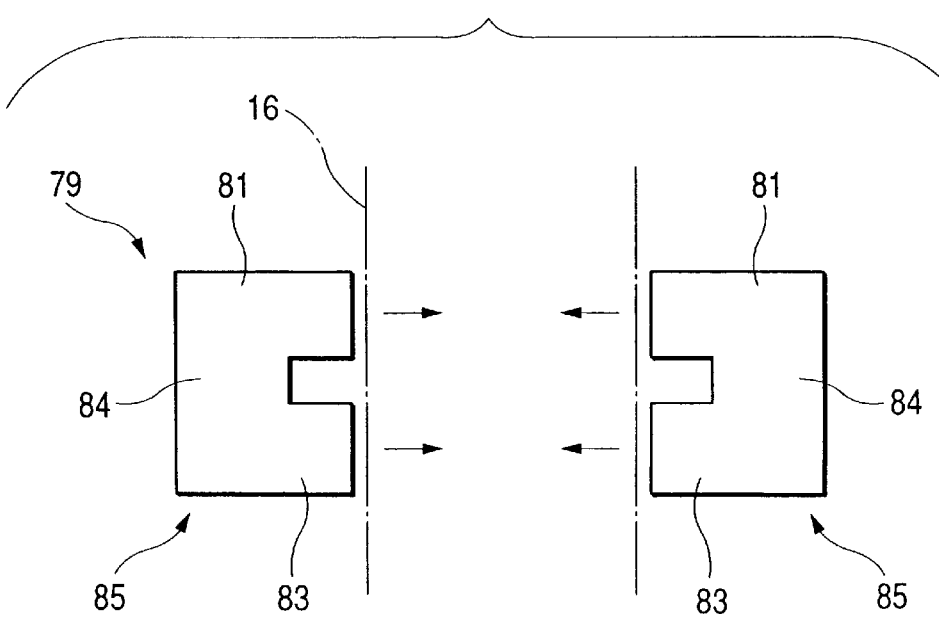

A method of forming of the assembly coupling crimp part 75 will be discussed in detail. That is, a crimping device 79 shown conceptually in FIGS. 15A to 15C is used in the method. As shown in FIGS. 15A and 15B, the crimping device 79 is made of crimp punches 81 and 83 for compressing the filter holding part 51 from the outside in the circumferential direction and first and second crimp punch units 80 and 82 spaced from each other at a predetermined distance in the axial direction of the filter holding part 51 as shown in FIG. 15C. The first crimp punch unit 80 forms the main crimp part 76 and the tip faces of the crimp punches 81 are combined to form a cylindrical face. On the other hand, the second crimp punch unit 82 forms the auxiliary crimp part 77 and the tip faces of the crimp punches 83 are combined to form an octagonal cylindrical face. As shown in FIG. 15C, the counterparts of the crimp punches 81 and 83 are coupled by a coupling part 84 to form a punch segment 85 and move toward and away from the outer peripheral surface of the filter holding part 51 in one piece in the radial direction thereof.

The punch segments 85 placed surrounding the filter holding part 51 are moved toward the filter holding part 51 all in union, whereby the filter holding part 51 is formed with the main crimp part 76 and the auxiliary crimp part 77 in batch. According to the method, the main crimp part 76 and the auxiliary crimp part 77 are formed at the same time by executing one crimping step, thus not only efficiency, but also the following advantage can be accomplished: Because of crimp punch compression, the filter holding part 51 digs locally in the main cylinder 14 and is pressed thereagainst to form the crimp part. A crease part or a relief part accompanying the dig deformation is easily formed in the filter holding part 51 in the surroundings of the press part. If the main crimp part 76 and the auxiliary crimp part 77 are formed in sequence, a crease part or a relief part caused by the crimp part formed later has an effect on the previously formed crimp part, impairing hermeticity. However, if both the crimp parts 76 and 77 are formed at the same time as described above, the effect of a crease part or a relief part can be pooled in the area between the crimp parts 76 and 77 and sufficient intimate contact, namely, hermeticity can be provided in the crimp parts 76 and 77.

Figure 16:
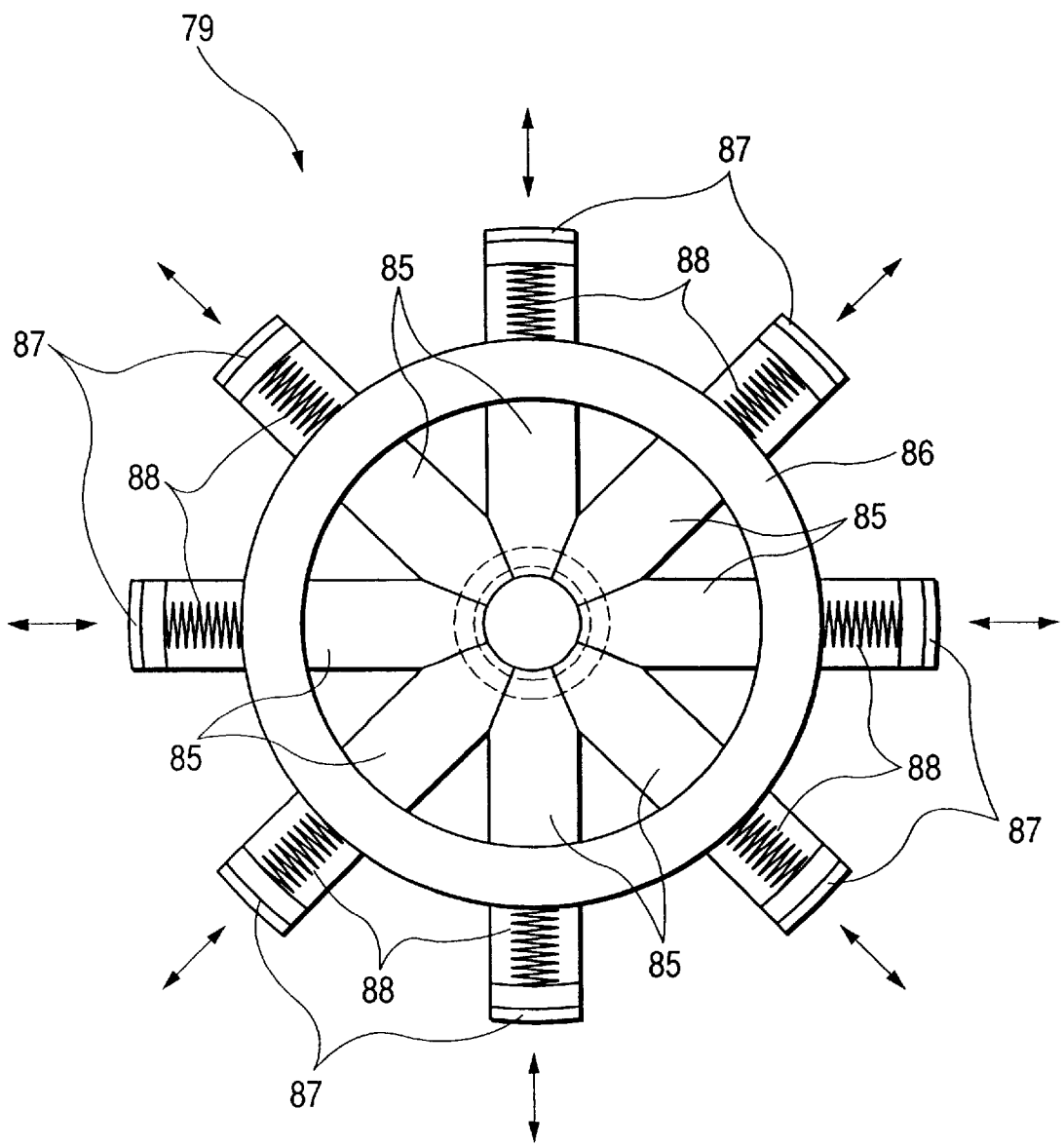
FIG. 16 is a schematic plan view to show the main part of the crimping device.
Figure 17A:
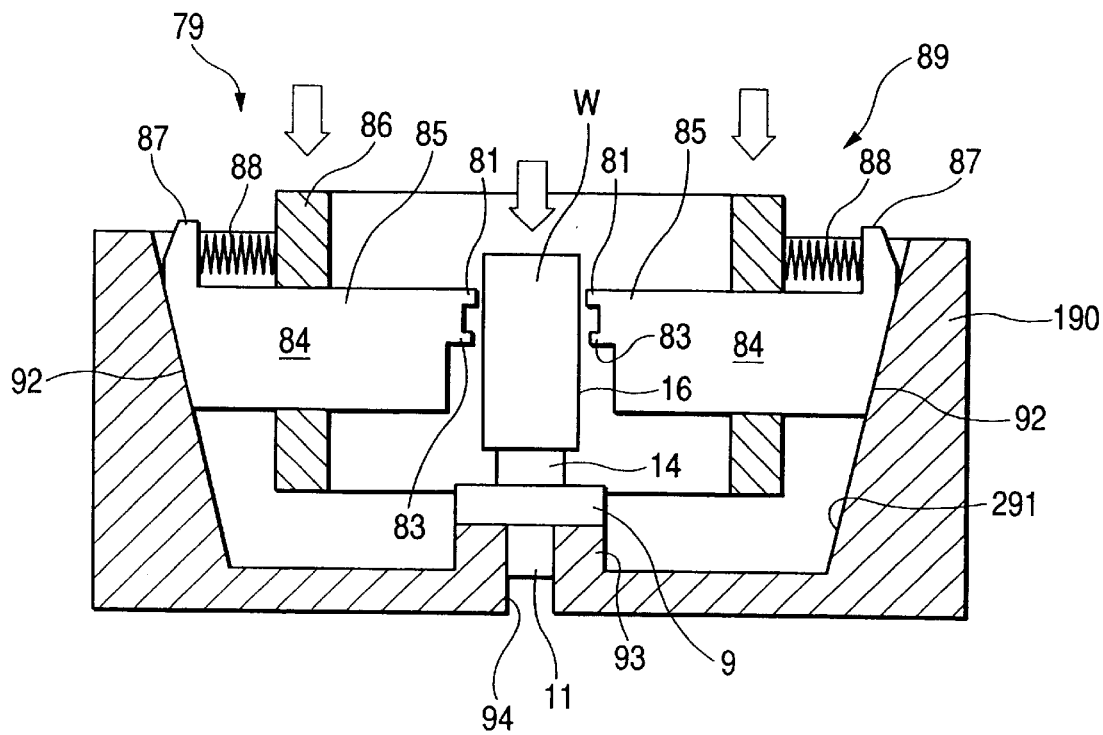
FIGS. 17A to 17B are schematic sectional views to show the main part of the crimping device.

FIG. 16 is a plan view to show an example of a more specific structure of the crimping device 79. That is, the crimping device 79 is constituted by a punch assembly 89 having a ring-like punch holder 86 and punch segments 85 placed along the circumferential direction of the punch holder 86 and piercing the punch holder 86 movably in the radial direction. Each punch segment 85 is formed at the rear with a spring support part 87 and a spring member 88 for urging the punch segment 85 outwardly is placed between the spring support part 87 and the outer peripheral surface of the punch holder 86. On the other hand, as shown in FIG. 17A, a reception unit 190 with an inner peripheral surface 291 formed as a taper face shrunk on the bottom is provided corresponding to the punch assembly 89 and a positioning projection 93 having a workpiece insertion hole 94 is formed at the center of the bottom.

A workpiece W with the filter assembly 16 put on the main cylinder 14 is set in the positioning projection 93 with the protector 11 inserted into the workpiece insertion hole 94. At this time, the main body metal shell 9 is supported on the top of the positioning projection 93 and the workpiece W is held in an erect state relative to the bottom center of the reception unit 190. The punch assembly 89 is set coaxially inside the reception unit 190 and the punch segments 85 surround the workpiece W. A taper corresponding to the inner peripheral surface 291 of the reception unit 190 is given to an outer end face 92 of the punch segment 85.

Figure 17B:
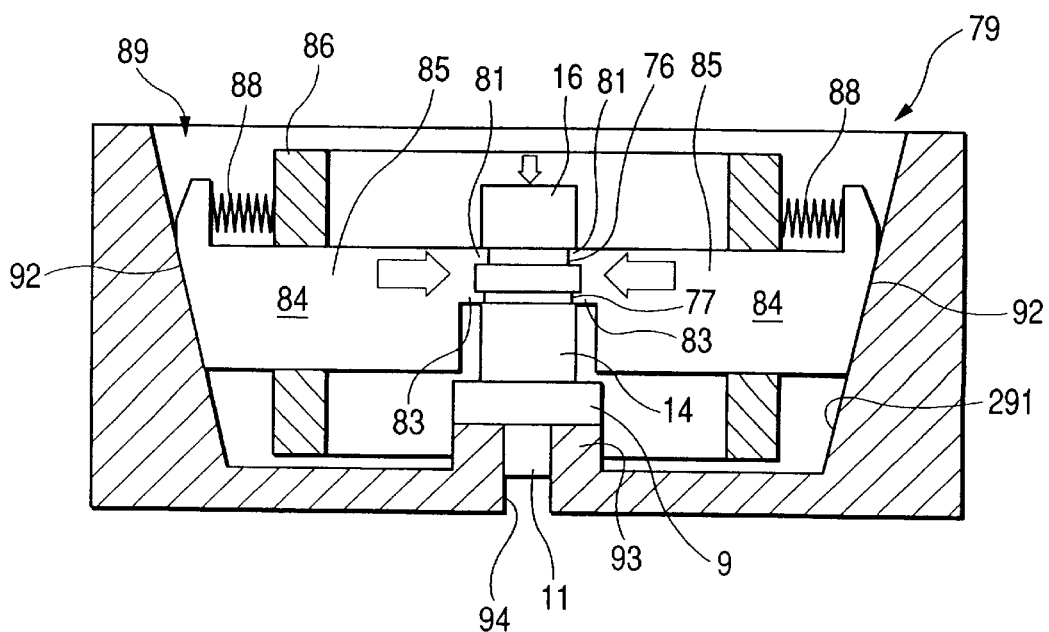

In this state, when the filter assembly 16 is pushed into the main cylinder 14 (FIG. 14B) by a pressure mechanism (not shown) and further the punch assembly 89 is pushed into the bottom of the reception unit 190, the punch segments 85 approach the workpiece W all in unison with the corresponding springs 88 compressed by the cam action between the outer end face 92 and the inner peripheral surface 291 tapered, forming the main crimp part 76 and the auxiliary crimp part 77 at the same time, as shown in FIG. 17B.

Next, the role of the metal elastic member 74 can also be replaced as follows: As shown in FIG. 42 and FIGS. 43A to 43E, a buffer support part 90 elastically deformed more easily than a main part 14b of the main cylinder 14 is formed in the rear opening end face part (casing support part) of the main cylinder 14 (casing 10) abutting the separator support part 73. If an assembling method similar to that in FIGS. 14A to 14E is adopted, the separator support part 73 is relatively pressed against the buffer support part 90, whereby the buffer support part 90 is compressed and deformed, producing an effect similar to that of the metal elastic member 74 described above. The filter assembly 16 is joined to the main cylinder 14 by the assembly coupling crimp part 75 and fixes the ceramic separator 18 to the casing 10 with the buffer support part 90 remaining compressed and deformed. That is, it plays a role of separator fixing means.

Figure 42:
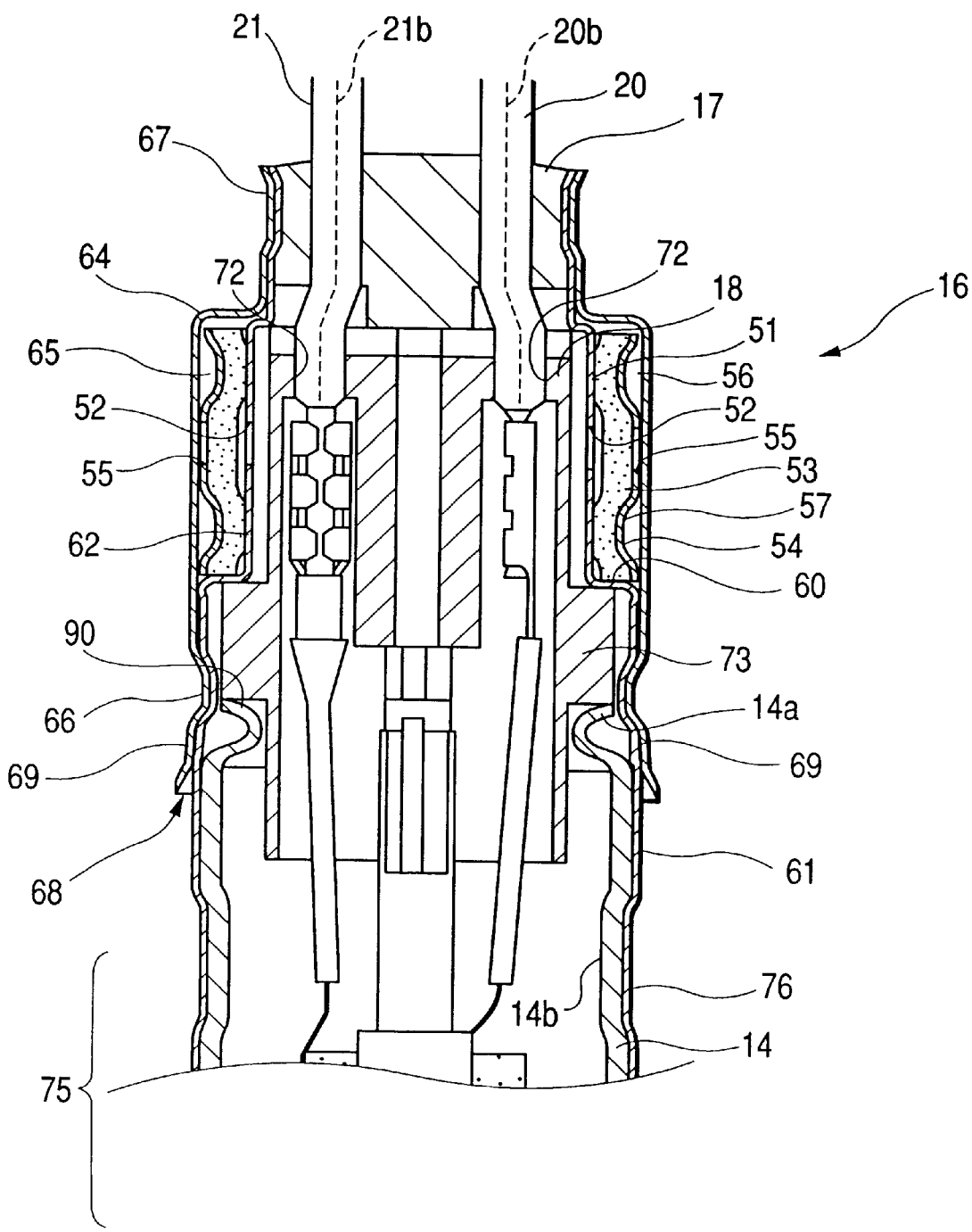
FIG. 42 is a longitudinal sectional view to show an example of forming a buffer support part as a spring part.

Specifically, as shown in FIG. 42, the buffer support part 90 can be formed as a spring part 90 integral with the main part 14b of the main cylinder 14. In the embodiment, the spring part 90 is formed by forming a thin part 14a in the opening end margin of the main cylinder 14, once bending back the thin part 14a to the inside in the radial direction of cross section, and furthermore once bending back the tip of the bent-back thin part 14a outwardly.

Figure 43A:
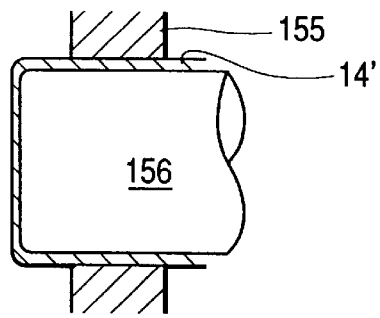
FIGS. 43A to 43E are schematic representations of an assembling process of the spring pat in FIG. 42.
Figure 43B:
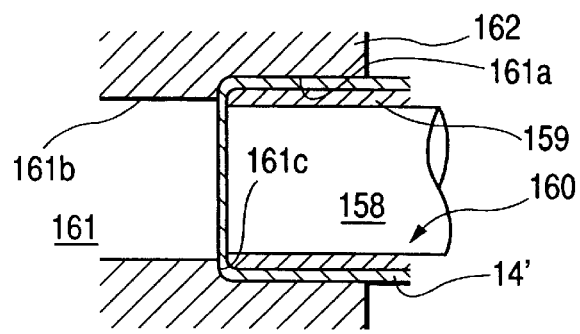
Figure 43C:
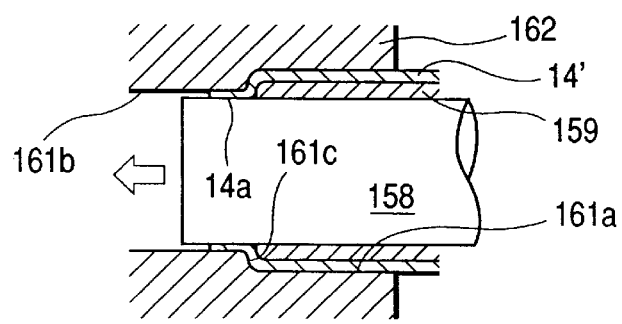

FIGS. 43A to 43E show an example of a method of forming the spring part 90. That is, as shown in FIG. 43A, a metal material is used to mold a cylindrical member 14' by multi-stage deep drawing using a die 155 and a punch 156. Next, as shown in FIG. 43B, using a complex punch 160 consisting of an inner punch 158 and an outer punch 159 placed concentrically outside the inner punch 158 and a die 162 having a die hole 161 formed with a large-diameter part 161a, a stepped part 161c, and a small-diameter part 161b in order in the depth direction, the outer margin of the cylindrical member 14' is sandwiched between the outer punch 159 and the stepped part 161c and as shown in FIG. 43C, the inner punch 158 is projected from the outer punch 159, whereby the bottom center of the cylindrical member 14' is punched. At this time, the periphery of the opening of the cylindrical member 14' is pressed into the gap between the inner punch 158 and the small-diameter part 161b of the die hole 161, forming the thin part 14a.

Figure 43D:
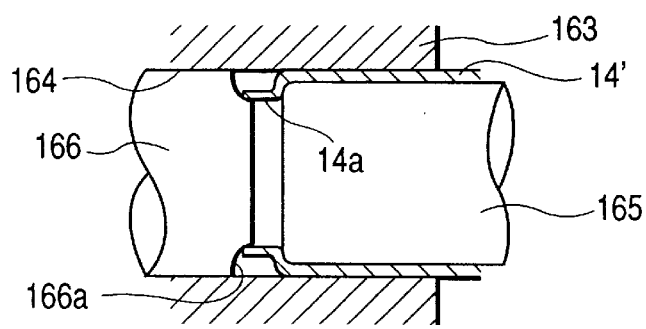
Figure 43E:
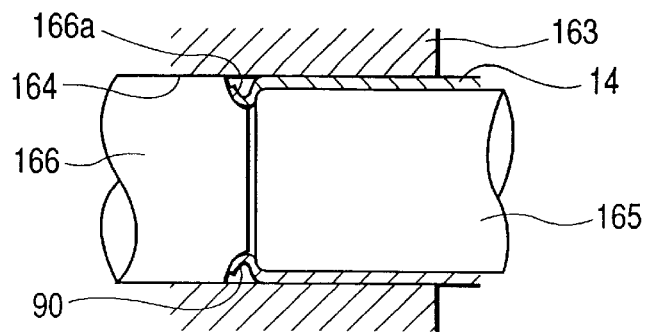

As shown in FIG. 43D, the thin part 14a is compressed and deformed so as to be crushed between a punch 165 inserted into the inside of the cylindrical member 14' and an opposed punch 166 opposed to the punch 165 in the die hole 164 of the die 163. The opposed punch 166 is formed in the tip face outer margin with a chamfer-like bend die part 166a having an inward curvature. As shown in FIG. 43E, the tip of the thin part 14a is pressed against the bend die part 166a and is bent slidingly outward, forming the spring part 90.

Figure 44:
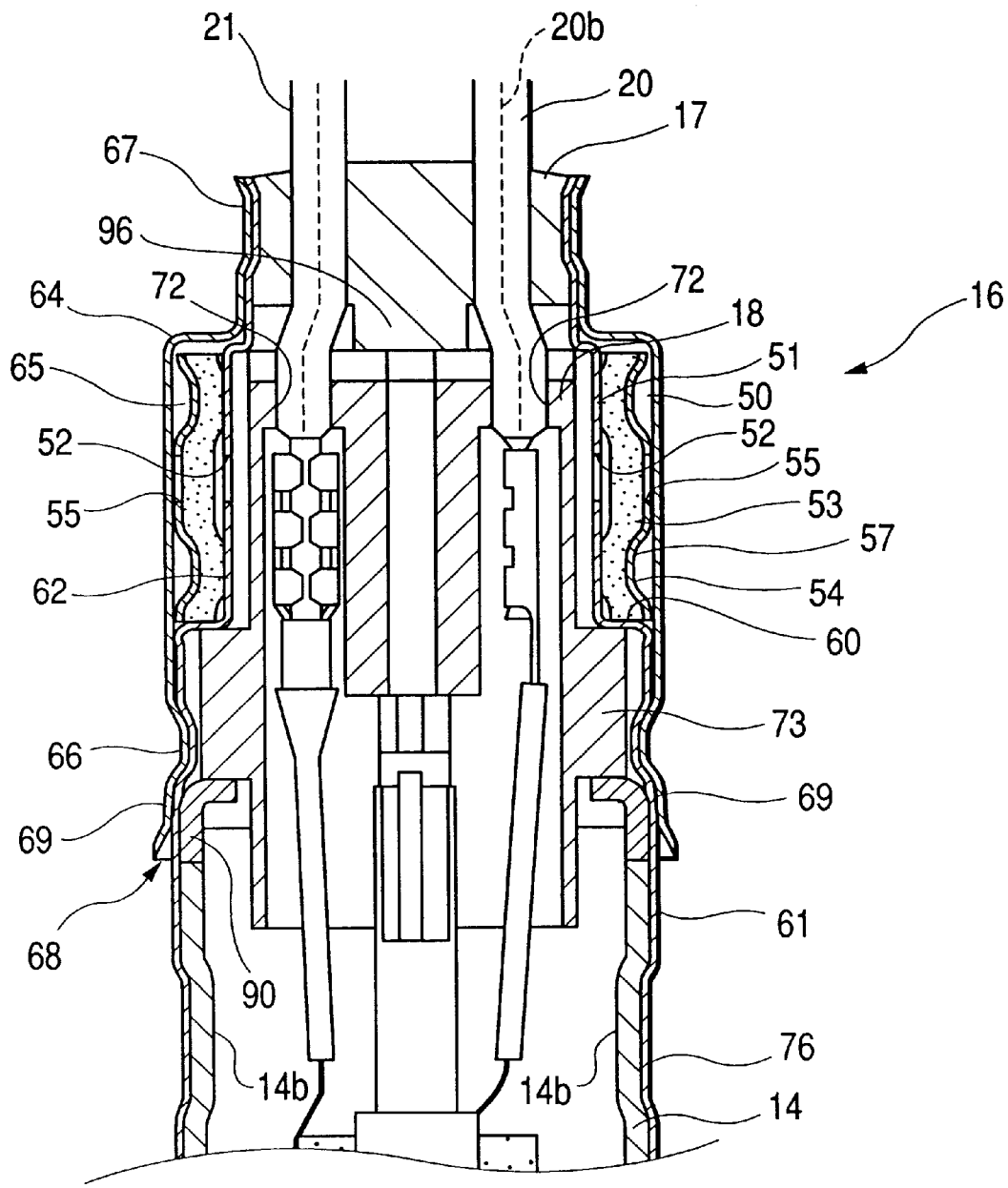
FIG. 44 is a longitudinal sectional view to show an example of forming a buffer support part as a low-hardness part.

On the other hand, as shown in FIG. 44, the buffer support part 90 may be formed so as to become a portion of lower hardness than the main part 14b of the main cylinder 14. That is, the hardness of the buffer support part 90 is made lower than that of the main part 14b, whereby when the separator support part 73 is pressed against the buffer support part 90, the buffer support part 90 is compressed and deformed, producing an effect similar to that of the metal elastic member 74 described above. The buffer support part 90 may be deformed within the elastic limit range or may be plastically deformed.

The buffer support part 90 can be formed of a different material having lower hardness than the main part 14b, for example. In this case, the different material portion can be joined to the main part 14b by welding, brazing, etc. On the other hand, for example, if the main cylinder 14 is formed of stainless steel, etc., the opening tip part is locally heat-treated by energization heating, etc., and is softened, whereby the main part 14b and the buffer support part 90 can also be formed in one piece with the same material.

Assuming that the Vickers hardness of the buffer support part 90 is Hvs and that the Vickers hardness of the main part 14b is Hvh, it is advisable to set Hvh is 320 or more. If Hvh becomes less than 320, the strength of the main cylinder 14 is insufficient and durability of the oxygen sensor 1 may be unable to be provided. Preferably, Hvh is set to 360 or more. It is advisable to adjust the hardness of the buffer support part 90 so that Hvh–Hvs (substracting Hvs from Hvs) becomes 60 or more. If Hvh–Hvs becomes less than 60, a relative deformation amount of the buffer support part 90 to the main part 14b is insufficient and an intended effect may be unable to be sufficiently accomplished. Preferably, Hvh–Hvs is set to 80 or more.

Next, as shown in FIG. 3, the ceramic separator 18 is placed so that the rear enters the inside of the filter holding part 51 in the axial direction of the oxygen sensing element 2 and that the front enters the inside of the main cylinder 14 (casing 10), and the leads 20, 21, 28, and 29 (FIG. 21) are inserted axially in the separator lead insertion holes 72. On the other hand, the elastic seal member 17 is fitted elastically into the inside of the rear opening 51a of the filter holding part 51, has seal lead insertion holes 91 for inserting the leads 20, 21, 28, and 29, and seals the space between the outer face of the leads 20, 21, 28, and 29 and the inner face of the filter holding part 51.

The rear end face of the ceramic separator 18 is positioned on the rear from the gas introduction hole 52 in the axial direction and adheres closely to the top face of a gap definition projection 96 formed in the rear end face center of the elastic seal member 17. A predetermined gap 98 is formed between the elastic seal member 17 and the ceramic separator 18 by the gap definition projection 96. A gap 92 is also formed between the inner peripheral surface of the filter holding part 51 and the outer peripheral surface of the ceramic separator 18. Gas from the gas introduction hole 52 is supplied to the gap 92 and is introduced into the casing 10 through a ventilation communication part 93 formed in the ceramic separator 18. Specifically, the ceramic separator 18 is formed with a through hole 95 for axial ventilation apart from the separator lead insertion holes 72 and is formed on the rear end face with a ventilation groove 94 communicating with the through hole 95 for ventilation at one end and opened to the outer peripheral surface of the ceramic separator 18 at the other end. That is, the through hole 95 for ventilation and the ventilation groove 94 make up the ventilation communication part 93.

Figure 18A:
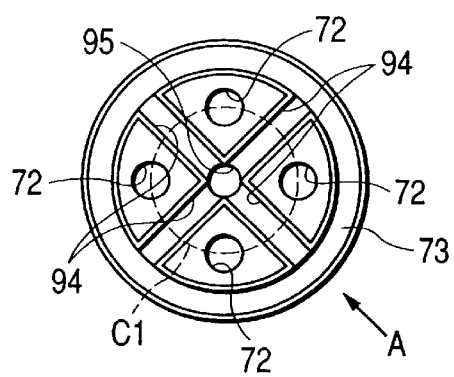
FIGS. 18A to 18E are schematic representations of a ceramic separator.
Figure 18B:
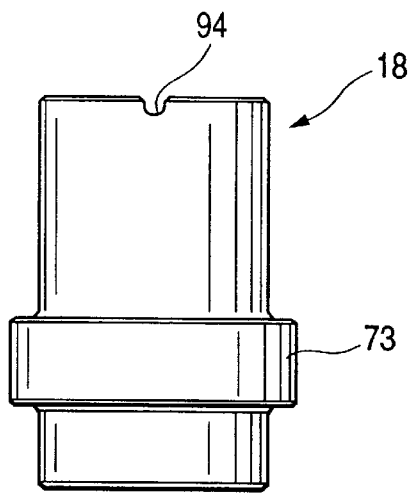
Figure 18C:
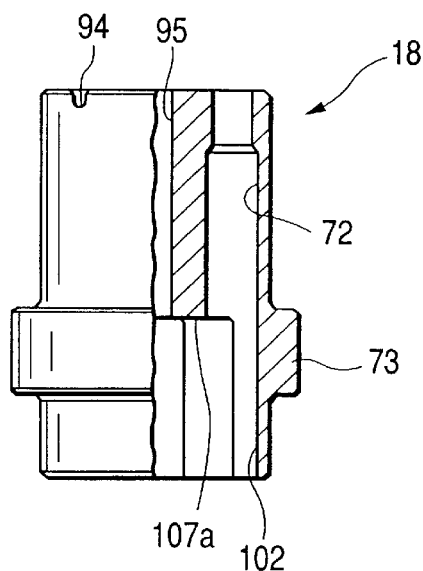
Figure 18E:
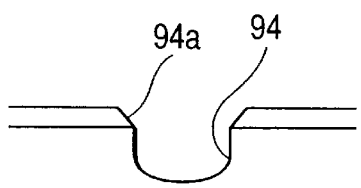
Figure 18D:
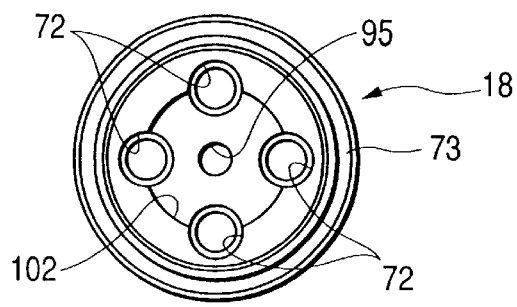

As shown in FIGS. 18A to 18D and FIG. 19A, in the ceramic separator 18, the four separator lead insertion holes 72 for inserting the leads 20, 21, 28, and 29 from the oxygen sensing element 2 and the heating element 3 are made so that the centers of the separator lead insertion holes 72 are positioned on a phantom circumferential path, which will be hereinafter called separator pitch circle, C1. The through hole 95 for ventilation is made in an area surrounded by the four separator lead insertion holes 72 at the center of the ceramic separator 18. Further, the ventilation groove 94 is shaped like a cross at a position not interfering with the four separator lead insertion holes 72 on the rear end face of the ceramic separator 18. As shown in FIG. 18E, the ventilation groove 94 is formed on the top with a chamfer part 94a on both margins in the width direction.

Figure 22A:
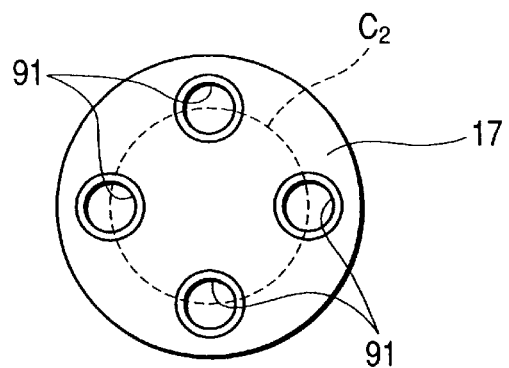
FIGS. 22A to 22C are schematic representations of an elastic seal member.
Figure 22B:
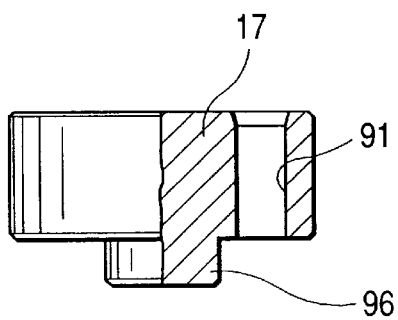
Figure 22C:
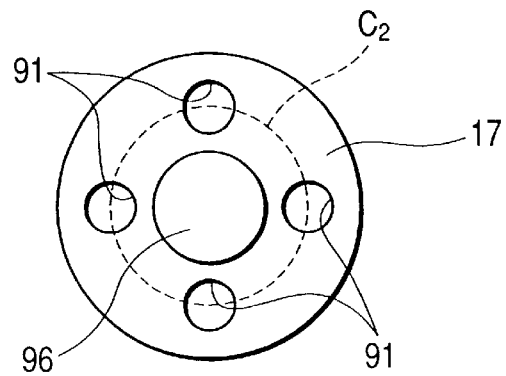

Next, as shown in FIGS. 22A to 22C, in the elastic seal member 17, the seal lead insertion holes 91 are made so that the centers thereof are positioned on a phantom circumferential path, which will be hereinafter called seal pitch circle, C2. The separator pitch circle C1 (diameter D1) and the seal pitch circle C2 (diameter D2) are set so that the diameter of one is larger than that of the other.

For example, in FIG. 3, D1>D2 and as shown in FIG. 22C, the gap definition projection 96 is formed in an area positioned in the inside of the seal lead insertion holes 91 arranged on the seal pitch circle C2.

In the described structure, the rear end face position of the ceramic separator 18 is set behind the gas introduction hole 52, whereby if water drops, etc., enter the filter assembly 16 through the gas introduction hole 52, they cannot flow into the casing 10 unless the water drops are once drawn into the rear end face of the ceramic separator 18 because the flange-like separator support part 73 blocks the opening of the main cylinder 14. Therefore, the effect of making it harder to allow water drops to flow into the oxygen sensing element 2 can be accomplished. In this case, the reference gas flowing in through the gas introduction hole 52 must also be drawn into the rear end face of the ceramic separator 18, but can be introduced into the casing 10 through the ventilation groove 94 and the through hole 95 for ventilation without a hitch.

On the other hand, the leads 20, 21, 28, and 29 are inserted into the elastic seal member 17 and the ceramic separator 18 in different pitch circle diameters, thus each lead is always bent between the elastic seal member 17 and the ceramic separator 18. However, the proper gap 98 is formed between the elastic seal member 17 and the ceramic separator 18 and the leads 20, 21, 28, and 29 can be bent in the gap 98 comparatively moderately, so that the leads will not be bent, damaged, or broken during the assembling of the oxygen sensor 1.

If the elastic seal member 17 and the ceramic separator 18 differ little in pitch circle diameter, they can also be brought into intimate contact with each other without forming the gap 98. If the gap 98 is formed, the tip face of the gap definition projection 96 adheres closely to the elastic seal member 17. In any case, the contact area between the elastic seal member 17 and the ceramic separator 18 overlaps the formation area of the through hole 95 for ventilation. However, even in such a case, the entrance of the through hole 95 for ventilation is not sealed and ventilation of the reference gas to the casing 10 is enabled because the ceramic separator 18 is formed on the top with the ventilation groove 94.

Figure 19A:
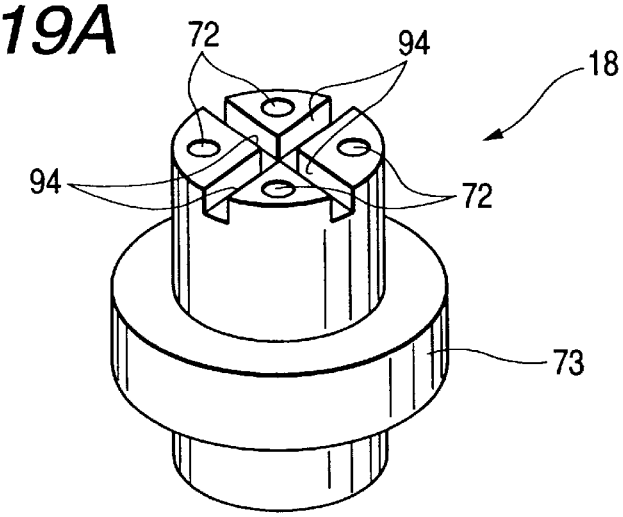
FIGS. 19A to 19C are perspective views to show the ceramic separator and modified examples thereof.
Figure 19B:
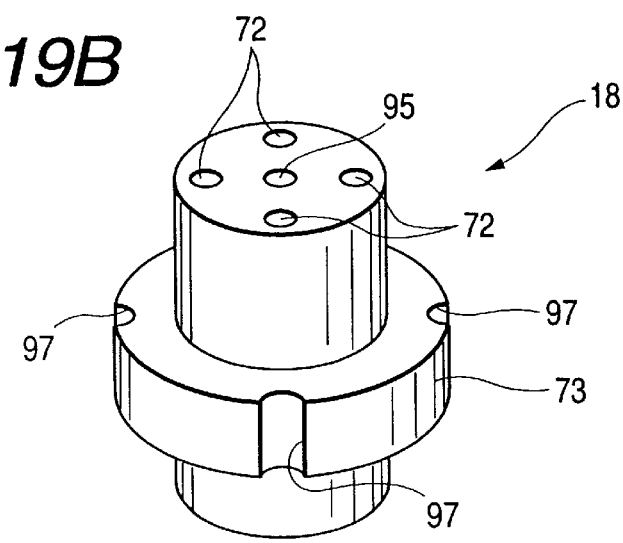
Figure 19C:
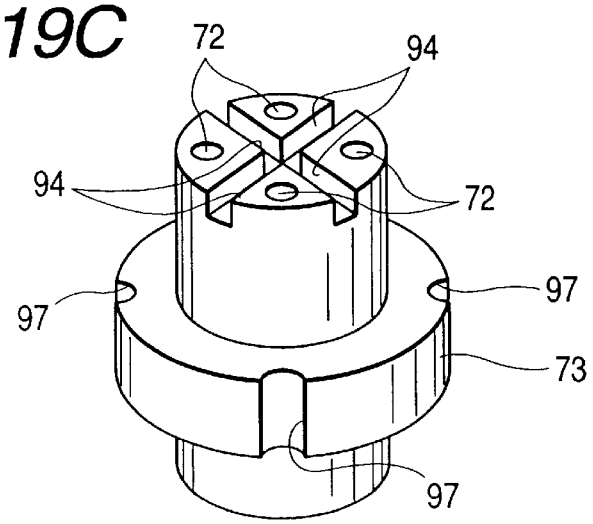
Figure 20:
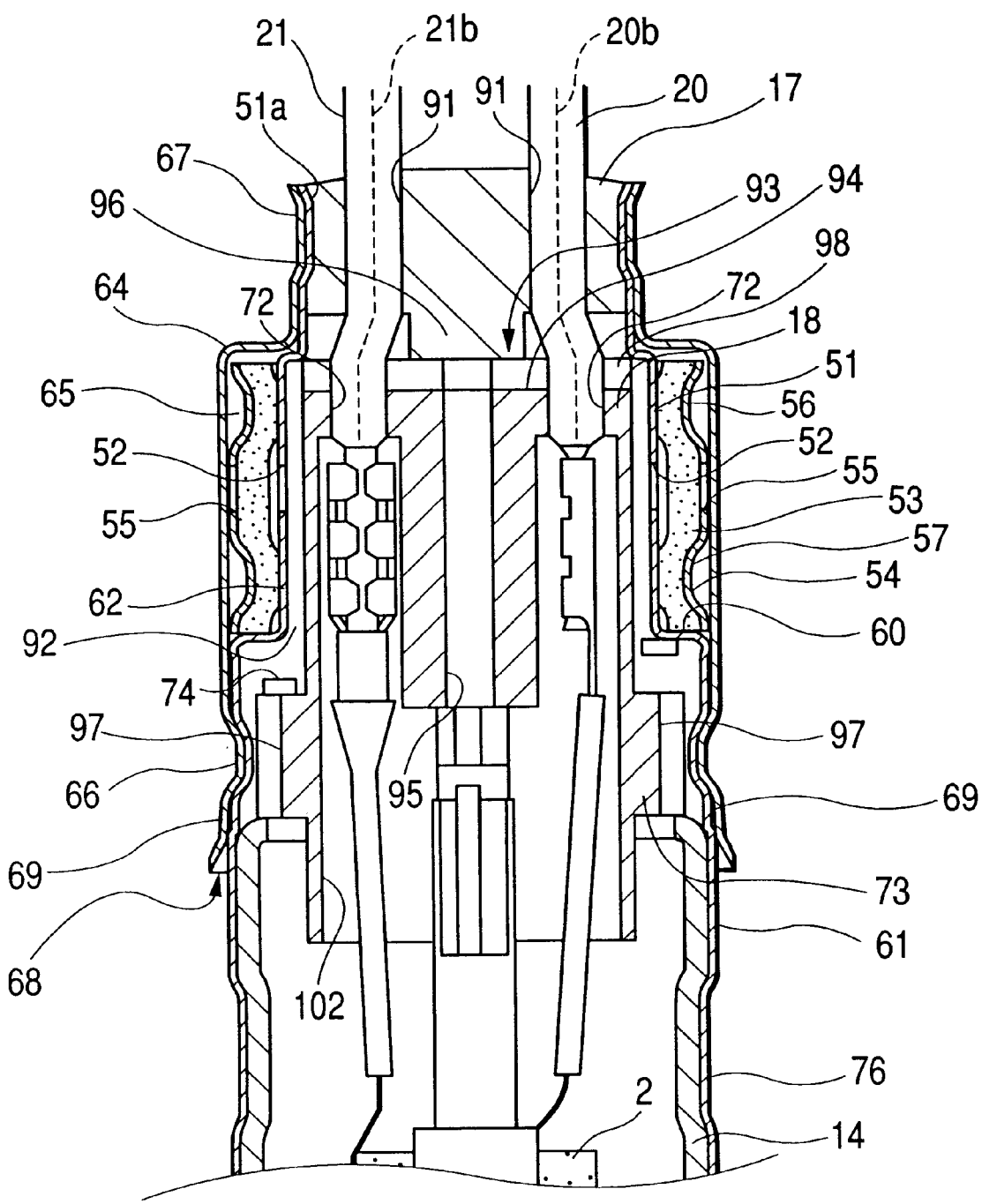
FIG. 20 is a longitudinal sectional view to show the main part of the oxygen sensor using the ceramic separator in FIG. 19c.

As shown in FIGS. 19B and 19C, the flange-like separator support part 73 (flange part) may be formed with through parts 97 for ventilation axially penetrating the separator support part 73. In the embodiment, the through parts 97 for ventilation are grooves (or notches) made at predetermined angle intervals in the outer peripheral surface of the separator support part 73. If the through parts 97 for ventilation are formed, the ventilation groove 94 can be omitted as shown in FIG. 19B. On the other hand, as shown in FIG. 19C, both the ventilation groove 94 and the through parts 97 for ventilation may be formed, in which case two ventilation passages of the ventilation groove 94 and the through hole 95 for ventilation and the through parts 97 for ventilation are formed, thus ventilation of the reference gas to the casing 10 is enabled more reliably. FIG. 20 shows an example of fitting the ceramic separator 18 into the oxygen sensor 1.

Figure 23A:
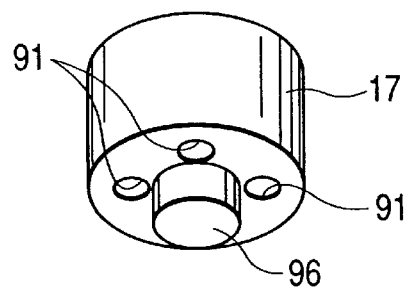
FIGS. 23A to 23C are perspective views to show the elastic seal member and modified examples thereof.
Figure 23B:
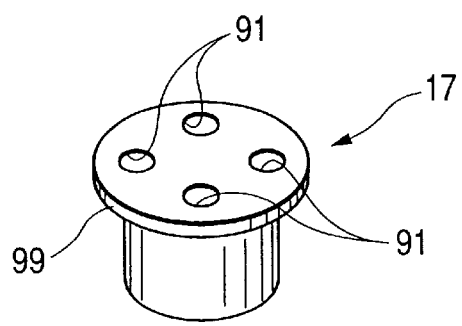
Figure 23C:
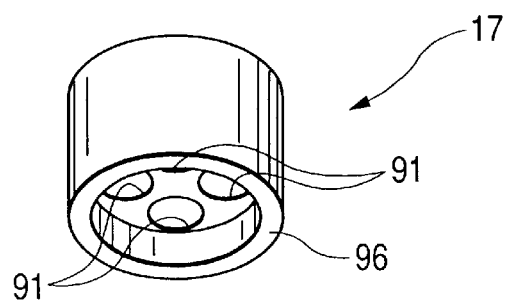
Figure 25:
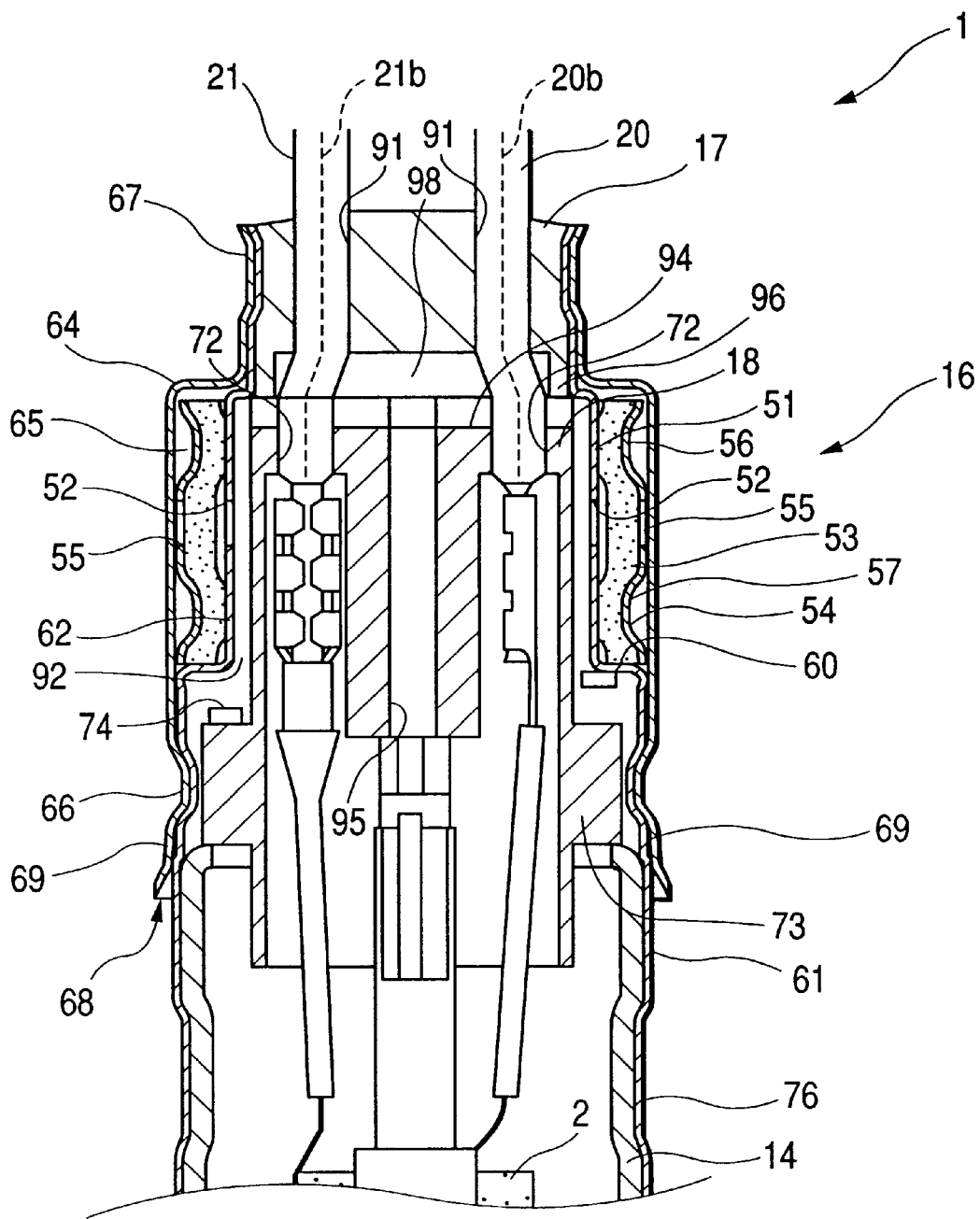
FIG. 25 is a longitudinal sectional view to show the main part of the oxygen sensor using the elastic seal member in FIG. 23c.

The gap definition projection 96 of the elastic seal member 17 can also be formed like a continuous or intermittent convex stripe along the periphery of the front end face of the elastic seal member 17, as shown in FIG. 23C and FIG. 25. In FIG. 25, the diameter D1 of the separator pitch circle C1 is larger than the diameter D2 of the seal pitch circle C2 (namely, D1>D2), but the structure can also be applied to the case where D1<D2, and is effective if D1 is small and the gap definition projection 96 contact area cannot sufficiently be provided in the area surrounded by the separator lead insertion holes 72, for example.

Figure 24:
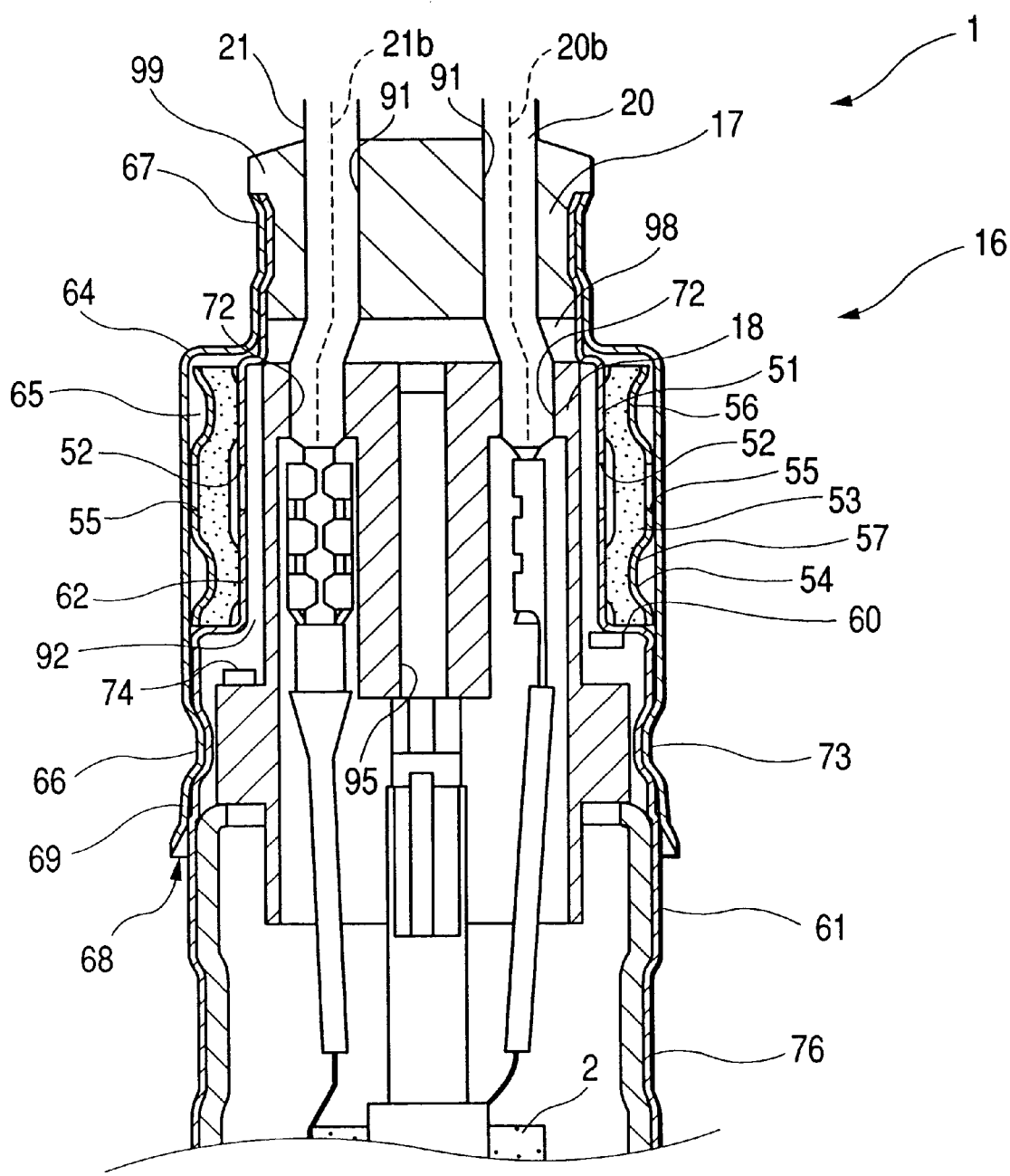
FIG. 24 is a longitudinal sectional view to show the main part of the oxygen sensor using the elastic seal member in FIG. 23b.

To form the gap 98 between the ceramic separator 18 and the elastic seal member 17, the elastic seal member 17 may be formed in the rear end margin with a flange part 99 projecting outward from the outer peripheral surface of the elastic seal member 17, as shown in FIG. 23B and FIG. 24. In this case, the flange part 99 of the elastic seal member 17 abuts the rear end face of the filter holding part 51, whereby the position of the front end face of the elastic seal member 17 in the filter holding part 51 is defined.

In the described oxygen sensor 1, while air as the reference gas is introduced through the filter 53 of the filter assembly 16 as described above, exhaust gas introduced through the gas permeation ports 12 of the protector 11 comes in contact with the outer face of the oxygen sensing element 2 and an oxygen concentration cell electromotive force occurs in the oxygen sensing element 2 in response to the oxygen concentration difference between the inner and outer faces. This oxygen concentration cell electromotive force is taken out as an oxygen concentration detection signal in the exhaust gas from the electrode layers 2b and 2c through the leads 21 and 20. Here, if the exhaust gas temperature is sufficiently high, the oxygen sensing element 2 is heated by the exhaust gas and is activated, but if the exhaust gas temperature is low at the engine starting time, etc., the oxygen sensing element 2 is heated forcibly by the heating element 3 and is activated.

Figure 28A:
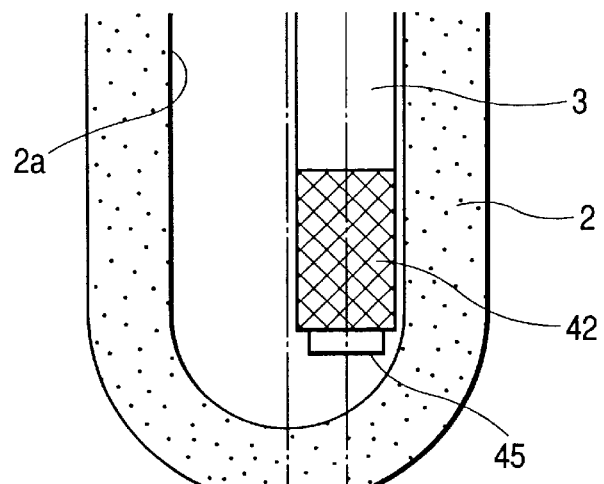
FIGS. 28A and 28B are partially sectional views to show the concept of the main part in FIG. 2 and a partially sectional view of a control example.
Figure 28B:
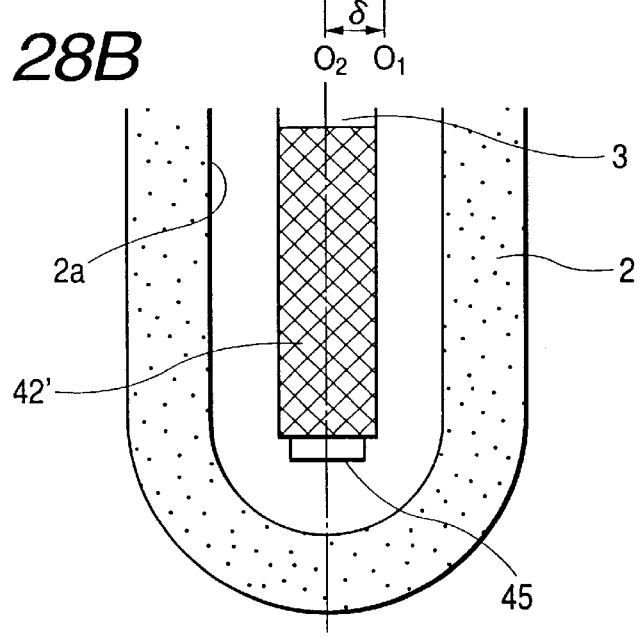
Figure 29A:
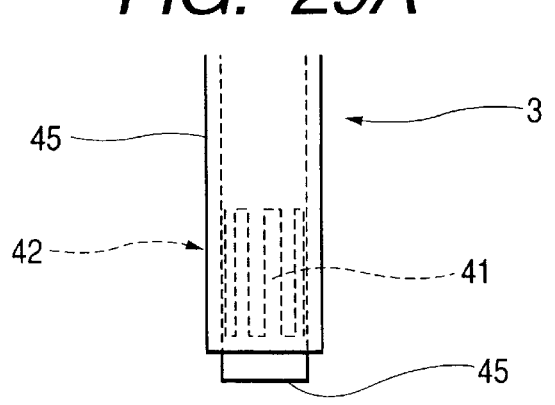
FIGS. 29A and 29B are a drawing to show an example of the heating part in FIG. 1.

The heating element 3 normally is a ceramic heater; it is constituted by a heating section 42 made up of a ceramic rod 45 consisting essentially of alumina, for example, as a core and a resistance line part (resistance pattern) 41 (FIG. 29) shaped like meandering, for example, on the surface of the ceramic rod 45, as shown in FIGS. 28A and 28B. It is provided by printing a predetermined pattern of resistance paste on a sheet-like external layer ceramic part 43 (FIG. 29) and winding the ceramic part 43 around the ceramic rod 45, then calcining. The ceramic rod 45 projects slightly from the tip of the external layer ceramic part 43 and the resistance pattern 41 is energized for generating heat through the leads 28 and 29 (FIG. 21) extending from the heater terminal parts 40 (FIG. 1, etc.,). The heating part 42 is one-sided to the tip of the heating element 3 and generates heat locally at the tip.

As shown in FIG. 28A, a center axis O1 in the proximity of the heating part 42 of the heating element 3 is offset by a given amount δ so that it is one-sided relative to a center axis O2 of the oxygen sensing element 2, so that the tip surface of the heating part 42 of the heating element 3 is in contact with a hollow part inner wall 2a of the oxygen sensing element 2, which will be hereinafter also called element inner wall 2a, in a state in which it is pressed against the wall 2a at predetermined face pressure. As seen in FIG. 1, the contact position is a position one-sided slightly to the intermediate side from the tip of the closed side of the oxygen sensing element 2 and more preferably a position almost corresponding to the gas permeation port 12 of the protector 11.

As shown conceptually in FIG. 30B, if a first phantom plane P1 containing the center axis O2 of the hollow part of the oxygen sensing element 2 and a second phantom plane P2 containing the center axis O2 of the hollow part and being orthogonal to the first plane P1 are set in the hollow part and the hollow part is divided by the first plane P1 and the second plane P2 into four areas, the heating element 3 is placed so that the whole of the portion of the center axis O1 positioned in the hollow part fits in any of the four areas. More specifically, also as shown in FIGS. 28A and 28B, the heating element 3 is placed so that the center axis O1 becomes almost parallel with the center axis O2 of the hollow part, whereby the heating element 3 is constituted by the heating part 42 having a side parallel with the hollow part inner wall 2a of the oxygen sensing element 2.

Figure 21A:
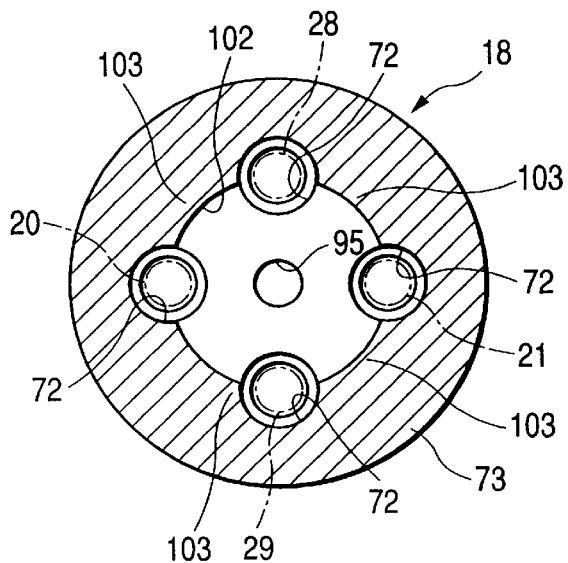
FIGS. 21A to 21C are schematic representations to show positional relationship between a heating element end housing hole and separator lead insertion holes in the ceramic separator.
Figure 21C:
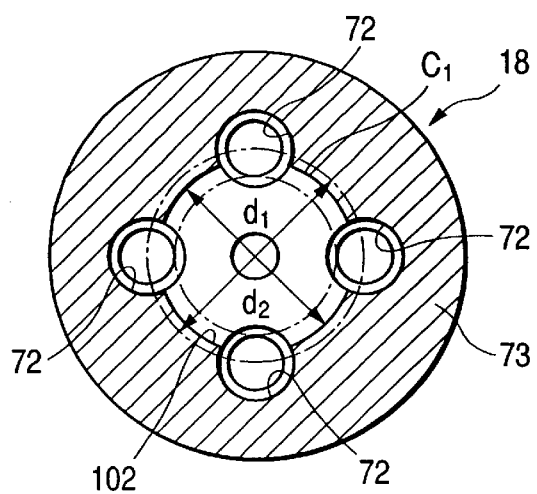
Figure 21B:
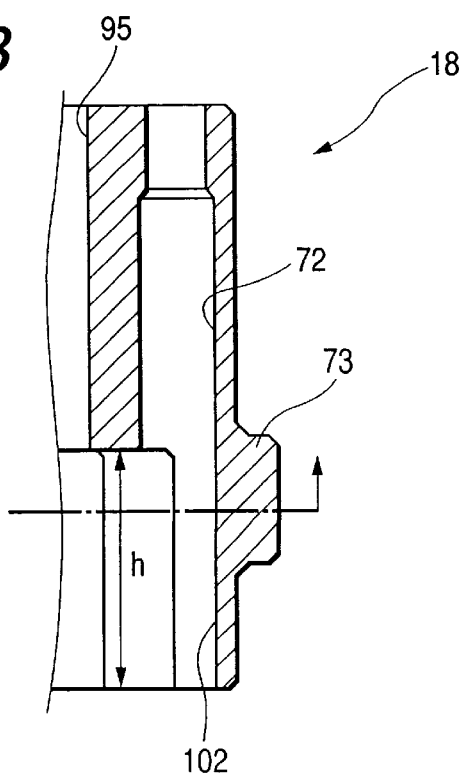

In response to offsetting the heating element 3 so as to be one-sided relative to the center axis of the hollow part of the oxygen sensing element 2, the ceramic separator 18 is designed as follows: As shown in FIG. 3, the ceramic separator 18 is formed with a heating element end housing hole 102 opened in the front end face of the ceramic separator 18 with a bottom 102a positioned in an axial intermediate part of the ceramic separator 18. The whole length of the oxygen sensor 1 can be shortened by housing the rear end part of the heating element 3 in the heating element end housing hole 102. Specifically, as shown in FIGS. 21A to 21B, the heating element end housing hole 102 is formed by cutting away the center of the ceramic separator 18 so as to overlap the separator lead insertion holes 72 from the inside and has an inner diameter set larger than the outer diameter of the heating element 3.

If the heating element 3 is offset as described above, the rear end part thereof is offset relative to the axis of the ceramic separator 18. Since the heating element end housing hole 102 for housing the rear end part of the heating element 3 has the inner diameter set larger than the outer diameter of the heating element 3, a diametrical move of the rear end part as the heating element 3 is offset is allowed within a given limit. That is, if the heating element 3 is offset, the rear end part thereof is prevented from interfering with the inner wall of the ceramic separator 18 and the offset amount can be set comparatively flexibly.

The separator lead insertion holes 72 are placed on the separator pitch circle C1 as described above and as shown in FIG. 21B, the inner diameter d1 of the heating element end housing hole 102 is set smaller than the diameter d2 of the separator pitch circle (namely, d1<d2). That is, the portion of the ceramic separator 18 positioned between the adjacent separator lead insertion holes 72 functions as a partition wall 103 for separating the leads 20, 21, 28, 29; as the heating element end housing hole 102 is made, the partition wall 103 is cut away from the inside. If d1≧d2, the diametrical length of the partition wall 103 becomes too short and the separation effect of the leads 20, 21, 28, 29 may be degraded, leading to a short circuit, etc.

It is desirable that the ratio between the diameter d2 of the pitch circle C1 of the lead insertion holes 72 and the outer diameter D of the end of the heating element 3, d2/D, is adjusted in the range of 1.7 to 2.8. If d2/D becomes less than 1.7, a sufficient offset amount of the heating element 3 cannot be provided, resulting in an insufficient lateral strike state of the heating element 3; a sufficient effect of shortening the sensor start-up time may be unable to be expected. If d2/D exceeds 2.8, the leads 20, 21, 28, 29 are too bent and damage, etc., to the leads easily occurs. It is advisable to set the ratio between depth h and inner diameter d1 of the heating element end housing hole 102, h/d1, to 1.2 or less. For example, to incline the heating element 3 to offset it, if h/d1 exceeds 1.2, the depth h of the housing hole becomes too large relative to the diameter d1 and a sufficient inclination amount of the heating element 3, namely, a sufficient offset amount cannot be provided; a sufficient effect of shortening the sensor start-up time may be unable to be expected.

Next, it is the terminal metal shell 23 (FIG. 1) that serves the function of offsetting the center axis O1 of the heating element 3 from the center axis O2 of the hollow part of the oxygen sensing element 2 in the above-described positional relationship and elastically pressing the heating part 42 against the element inner wall 2a. In this case, the terminal metal shell 23 plays the following three roles: First, electric connection to the lead 20 as an output terminal of the electrode layer 2c inside the oxygen sensing element 2; second, fitting of the heating element 3 to the inside of the oxygen sensing element 2 (function similar to the conventional function); and third, elastically pressing the tip of the heating element 3 agiant the element inner wall 2a in a lateral strike structure.

Figure 26A:
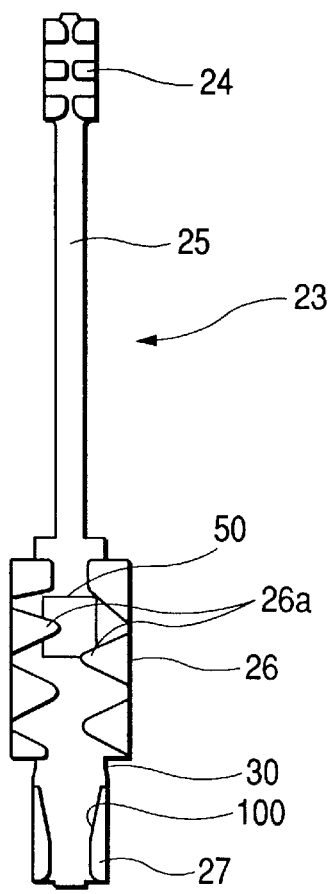
FIGS. 26A to 26B are drawings to show a discrete state of a terminal metal shell in FIG. 1.
Figure 26B:
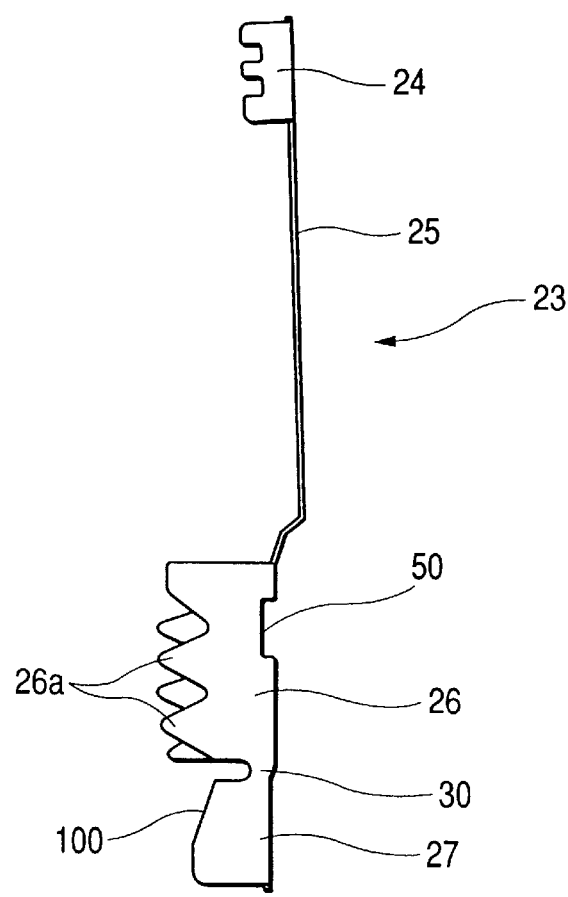
Figures 27A, 27B:
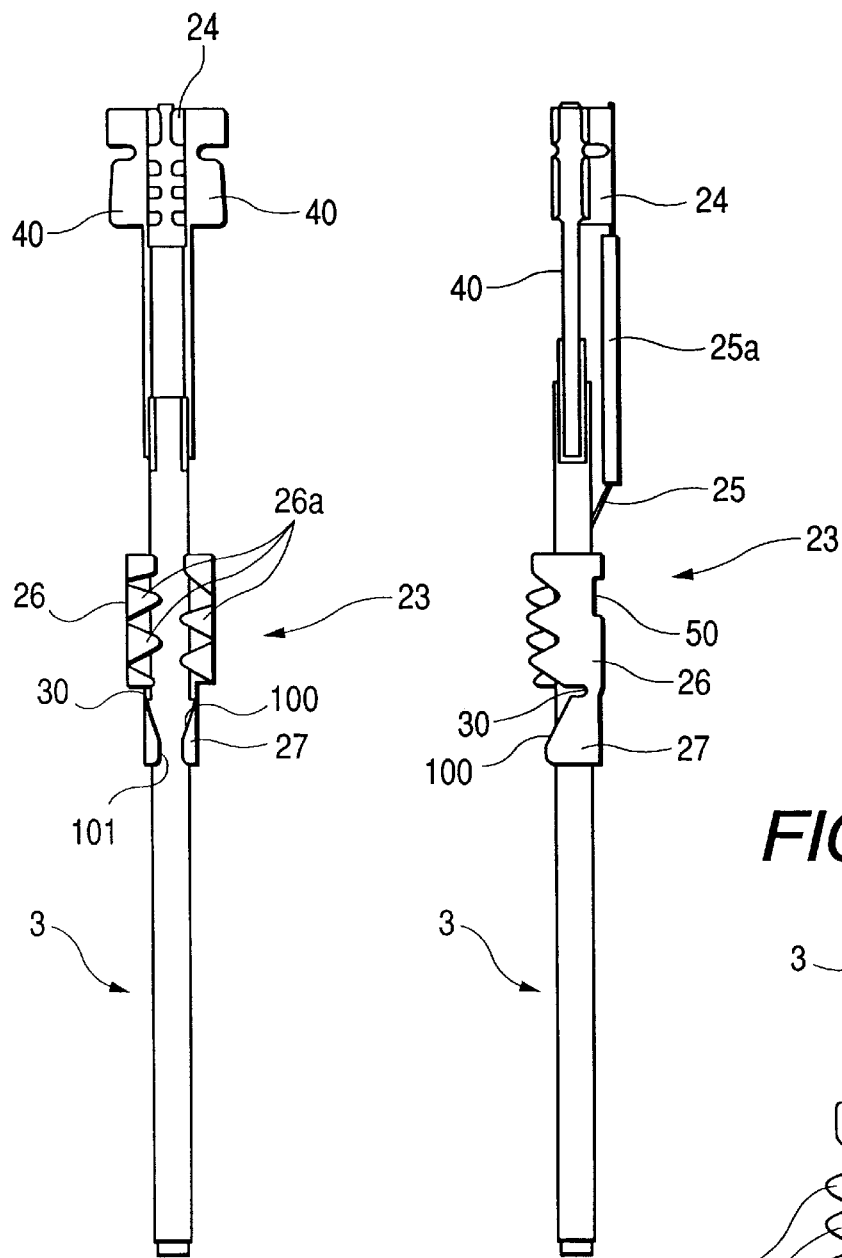
FIGS. 27A to 27C are drawings to show an assembly of fitting the terminal metal shell into the heating element in FIG. 1.
Figure 27C:
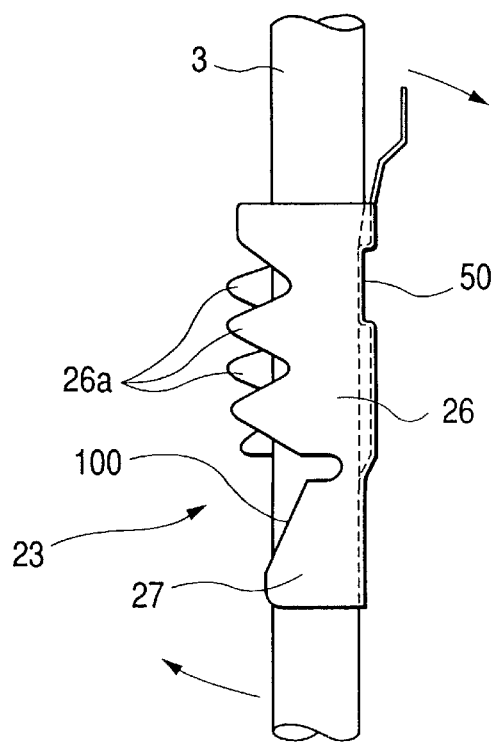

FIGS. 26A and 26B show a discrete state of the terminal metal shell 23 and FIGS. 27A to 27C show a state in which the terminal metal shell 23 is fitted into the heating element 3. As seen in the figures, a heating element grip part 27 is formed at the tip of the heating element 3 relative to the internal electrode connection part 26, namely, the side close to the heating part 42. The heating element grip part 27 has a transverse section shaped like a C letter surrounding the heating element 3. When the heating element 3 is not inserted, the heating element grip part 27 has an inner diameter a little smaller than the outer diameter of the heating element 3. As the heating element 3 is inserted, the diameter of the heating element grip part 27 is elastically enlarged for gripping the heating element 3 by a friction force. The heating element grip part 27 is disposed only at one place on one side of the internal electrode connection part 26.

The internal electrode connection part 26 is formed so as to surround the heating element 3 by bending like a cylinder, a plate-like portion formed with contact parts 26a like saw teeth in both left and right margins. It positions the heating element 3 axially with respect to the hollow part by the friction force between the outer peripheral surface and the hollow part inner wall 2a of the oxygen sensing element 2 and comes in contact with the inner electrode layer 2c (FIG. 2) at the tips of the contact parts 26a. A predetermined gap is formed between the internal electrode connection part 26 and the heating element 3. The left and right contact parts 26a have portions corresponding to the crests and troughs of the saw teeth in offset relation on the left and the right. For example, when the internal electrode connection part 26 is inserted into the oxygen sensing element 2 at the sensor assembling time, the left and right contact parts 26a do not get caught in the opening margin of the oxygen sensing element 2, in turn facilitating fitting of the internal electrode connection part 26 into the oxygen sensing element 2. The height of each of the contact parts 26a like saw teeth is set slightly large, whereby when the plate-like portion is bent like a cylinder to form the internal electrode connection part 26, the effect of increasing the width in the bending direction for facilitating working is also accomplished.

As shown in FIGS. 27A to 27C, a heating element insertion guide part 100 is formed in the margin far from the tip of the oxygen sensing element 2 in the axial direction of the heating element grip part 27, namely, the front margin. Specifically, the heating element grip part 27 is formed with a slit 101 from one margin to an opposite margin in the axial direction and the heating element insertion guide part 100 is formed like a taper by cutting away both side portions of the slit 101 slantingly toward one margin from an intermediate position of the slit.

The heating element 3 can be fitted into the terminal metal shell 23 by inserting the heating element 3 into the heating element grip part 27 of the terminal metal shell 23 from the tip. It is pushed into the heating element grip part 27 while widening the heating element grip part 27 diametrically outward from the opening. At this time, the heating element 3 may be unable to be inserted smoothly because the tip margin of the heating element 3 is caught in the end margin of the grip part 27. Particularly, if the slit 101 as described above is formed so that the grip part 27 can be elastically deformed diametrically, the heating element 3 is easily caught in the margin of the slit 101. Then, if the slit 101 is formed with the taper-like heating element insertion guide part 100, insertion of the heating element 3 is guided smoothly by the effect of the taper, thus the heating element 3 will not be caught in the margin and can be fitted efficiently into the terminal metal shell 23. However, if catching the heating element 3 in the margin, etc., does not introduce a large problem at the assembling time, the heating element insertion guide part 100 may be omitted.

Referring again to FIG. 1, the internal electrode connection part 26 is formed with a positioning projection part 50 projecting from the inner face and abutting the outer peripheral surface of the heating element 3 at a position corresponding to a coupling part 30 of the heating element grip part 27 to the internal electrode connection part 26 in the proximity of the end on the opposed side to the side where the heating element grip part 27 is coupled. The positioning projection part 50 is formed, for example, by denting the wall of the internal electrode connection part 26 inward by press working, etc., for positioning the heating element 3 in offset relation to the center axis O2 of the hollow part of the oxygen sensing element 2 as described above.

The hollow part inner wall 2a of the oxygen sensing element 2 is given a slight taper with the bottom shrunk in diameter for the purpose of enhancing the releasability at the molding time, etc., when it is manufactured by molding and calcining solid electrolyte powder. In contrast, the heating element 3 is placed so that the center axis O1 thereof becomes almost parallel with the center axis O2 of the oxygen sensing element 2, as shown in FIGS. 28A and 28B, etc. Thus, it is necessary to make the gap formed between the heating element 3 and the hollow part inner wall 2a larger as it heads for the base end of the heating element 3. The gap amount at the formation position of the positioning projection part 50 is defined to be a predetermined value, whereby the positioning projection part 50 satisfies the positional relationship wherein the heating element 3 comes in contact with the hollow part inner wall 2a in the proximity of the heating part 42 and the two center axes O1 and O2 become almost parallel with each other.

In the manufacturing process of the oxygen sensor 1, normally the terminal metal shell 23 is fixed to the heating element 3 and then their assembly is inserted into the oxygen sensing element 2. Here, assuming that there is no restraint force of the heating element 3 from the wall of the oxygen sensing element 2, the radial coupling position relationship of the heating element grip part 27 to the internal electrode connection part 26 is defined so that the heating element grip part 27 and the positioning projection part 50 hold the center axis O1 of the heating element 3 with the heating part 42 a little inclined so as to be away from the center axis O2 of the hollow part of the oxygen sensing element 2, whereby when the assembly is inserted, the tip of the heating element 3 is inserted into the element inner wall 2a while sliding in elastic contact with the element inner wall 2a and as indicated by arrows in FIG. 27C, the heating element 3 is attached to the oxygen sensing element 2 while the inclination state is corrected in the direction in which the center axis O1 of the heating element 3 becomes parallel with the center axis O2 of the hollow part. The coupling part 30 between the heating element grip part 27 to the internal electrode connection part 26 is formed in a narrow shape by forming a U-shape notch in the circumferential direction from both sides. When the heating element 3 is attached to the oxygen sensing element 2, the coupling part 30 becomes elastically deformed inward and presses the heating part 42 of the heating element 3 against the hollow part inner wall 2a of the oxygen sensing element 2 by an elastic restoration force, producing a lateral strike form as shown in FIG. 1.

In this state, a resultant bend moment of stress exerted on the heating element 3 by the element inner wall 2a, stress acting on the heating element 3 in the positioning projection part 50, and stress acting on the heating element 3 in the heating element grip part 27 occurs in the heating element 3. The coupling part of the narrow part adjacent to the internal electrode connection part 26 adjusts the stress or the bend moment so that the heating element 3 is not broken by the bend moment, in other words, stress exceeding the allowable strength range of the heating element 3 does not occur.

That is, the coupling part 30 also plays a roll in absorbing and buffering the bend force given to the heating element 3 via the heating element grip part 27 and the positioning projection part 50 in the insertion step for preventing damage, etc., to the heating element 3. The elastic force can be adjusted by adjusting the width of the narrow part. In other words, the narrow width of the coupling part 30 is set properly, whereby the elastic force can be adjusted to a proper value and in the lateral strike structure of the heating element 3 in FIG. 1, the elastic press force against the element inner wall 2a can be provided as a necessary sufficient value.

Figure 29B:
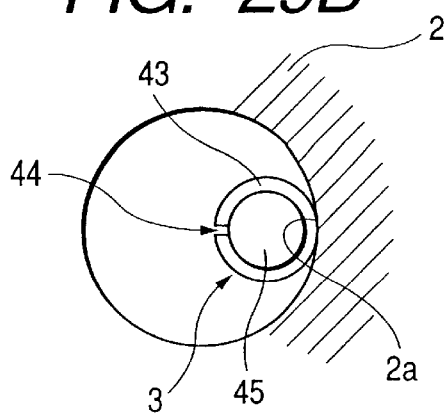

Next, as shown in FIG. 29B, a slit-like part 44 parallel with the axial direction occurs at one point of the outer periphery of the heating element 3 as a joint gap when the external layer ceramic part 43 of the heating element 3 is wound around the ceramic rod 45, the resistance pattern 41 does not exist in the proximity of the slit-like part 44, and a heating sparse portion results. In the lateral strike structure of the heating element 3 against the element inner wall 2a, it is desirable to strike the surface of the heating part 42 on the opposite side to the slit-like part 44 against the element inner wall 2a. In doing so, effective heat transmission occurs from the sufficient heating portion directly to the oxygen sensing element 2.

The hollow part inner wall 2a of the oxygen sensing element 2 is shaped like a taper. The difference between inner diameter mean value (simply, inner diameter) DA of the hollow part inner wall 2a and outer diameter DB of the heating element 3, ΔD=DA−DB, is set to 0.1–0.35 mm, preferably 0.15–0.30 mm. The ratio of ΔD to the outer diameter DB of the heating element 3, ΔD/DB, is set to 0.13 or less, preferably 0.10 or less.

The operation of the oxygen sensor 1 will be discussed.

FIG. 28B shows an example of a structure in which the center axis O1 of the heating element 3 is concentric with the center axis O2 of the oxygen sensing element 2. As seen by comparing it with FIG. 28A, in the example in FIG. 28A, the center axis O1 of the heating element 3 is offset by distance 8 from the center axis O2 of the oxygen sensing element 2 with the center axis O1 of the heating element 3 almost parallel with the center axis O2 of the oxygen sensing element 2 and the tip surface of the heating part 42 is pressed against the element inner wall 2a from side as a lateral strike structure. For easy understanding in FIG. 28A, the gap between the heating element 3 and the oxygen sensing element 2 is drawn bombastically; when the inner diameter of the element inner wall 2a is 2.8–3.2 mm and the outer diameter of the heating element 3 is 2.43–2.63 mm, it is advisable to set the offset amount δ to about 0.085–0.385 mm, for example, to provide the lateral strike structure reliably without producing an excessive press force between the heating element 3 and the oxygen sensing element 2. As compared with a heating part 42' in FIG. 28B, the heating part 42 in FIG. 28A is one-sided to the narrow area on the tip side of the heating element 3, as described above.

Such a lateral strike structure of the heating element 3 against the element inner wall 2a is adopted, whereby heat generated in the heating part 42 is transmitted promptly to the oxygen sensing element 2 by heat conduction based on the above-mentioned contact for heating the oxygen sensing element 2 and the oxygen sensing element 2 is also heated by heat radiation of the locally heated portion in the proximity of the contact part. The synergistic heat transmission of the heat conduction and the heat radiation heats the oxygen sensing element 2 rapidly, shortening the rise time to activation temperature.

Here, as shown in FIG. 2, the oxygen sensing element 2 is heated locally by the heating part 42 placed in the lateral strike state against the element inner wall 2a. The sensor start-up time is maintained to a similar degree to that of the sensor of the structure shown in FIG. 28B or is shortened. The following is possible as the factor: For a sufficient oxygen concentration cell electromotive force to occur in the oxygen sensing element 2 formed of an oxygen ion conductive solid electrolyte, it is necessary to sufficiently raise catalyst activity of the electrode layers 2b and 2c to an oxygen molecule dissociation or rebonding reaction as well as to sufficiently lessen the electric resistance value of the oxygen sensing element 2. The detection output level of the sensor is determined by tradeoffs of the electric resistance value of the oxygen sensing element 2 and the catalyst activity of the electrode layers 2b and 2c.

When the oxygen sensing element 2 is heated locally by the heating part 42, a decrease in electric resistance of the oxygen sensing element 2 as the solid electrolyte is activated develops less than that in the structure shown in FIG. 28B, for example. However, as shown in FIG. 2, locally heated portion 2d is heated to higher temperature, thus the catalyst activity of the electrode layers 2b and 2c is raised in the portion. When the catalyst activity of the electrode layer 2b improves, dissociation of oxygen molecules in measured gas is promoted and the effect compensates for the concentration cell electromotive force of the solid electrolyte and in turn the detection output level of the sensor, resulting in shortening of the sensor activation time (start-up time).

The heating element 3 is placed so that the center axis O1 of the heating element 3 becomes almost parallel with the center axis O2 of the oxygen sensing element 2, whereby the side of the heating part 42 becomes almost parallel with the hollow part inner wall 2a of the oxygen sensing element 2 and the walls of the oxygen sensing element 2 can be heated more uniformly by the heating part 42 and in turn the effect of shortening the oxygen sensor activation time is enhanced furthermore.

Further, as shown in FIG. 1, in the terminal metal shell 23, the heating element grip part 27 is coupled only to the side of the internal electrode connection part 26 near to the heating part 42 of the heating element 3, thus the length of the terminal metal shell 23 in the axial direction of the heating element 3 becomes short and in turn the oxygen sensor 1 is shortened in the axial length and is made compact. Since the heating element 3 is gripped by one grip part 27, when the heating element 3 with the terminal metal shell 23 attached is inserted into the hollow part of the oxygen sensing element 2 for assembling the oxygen sensor 1, an excessive lateral force via the terminal metal shell 23 becomes hard to act on the heating element 3 and damage, etc., to the heating element 3 at the assembling time can be prevented, as described above.

Figure 31:
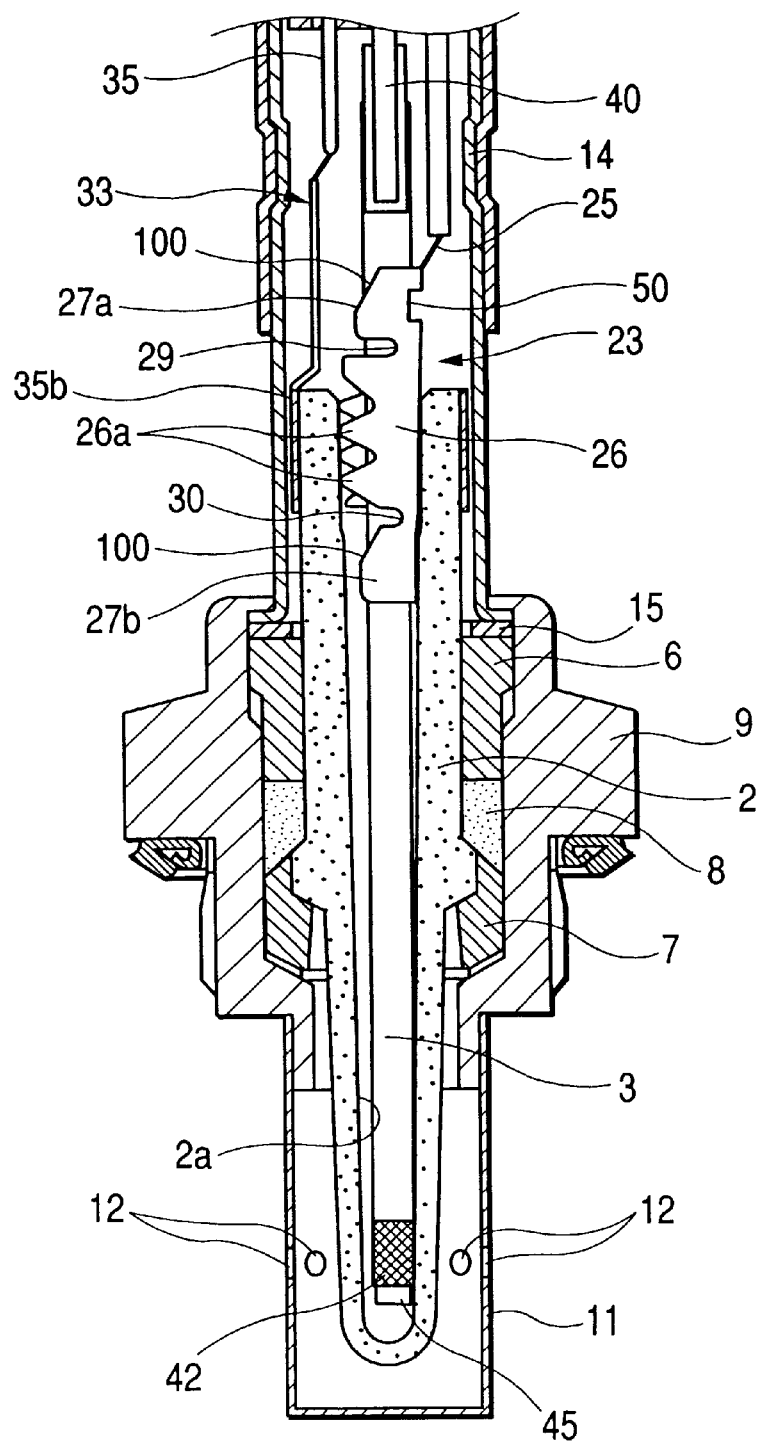
FIG. 31 is a longitudinal sectional view to show a first modified example of the oxygen sensor in FIG. 1.
Figure 32:
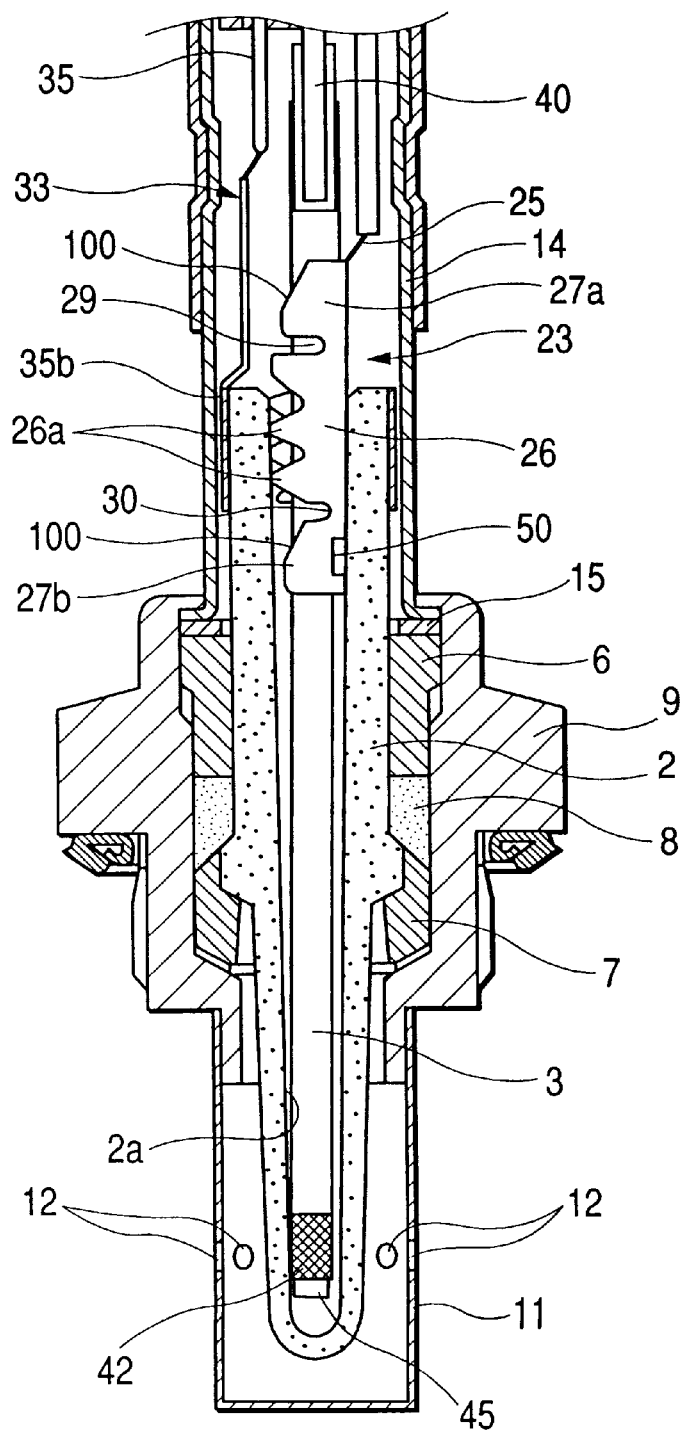
FIG. 32 is a longitudinal sectional view to show a second modified example of the oxygen sensor in FIG. 1.

As shown in FIG. 31 and FIG. 32, in the terminal metal shell 23, two heating element grip parts 27a and 27b can also be coupled to both axial sides of the internal electrode connection part 26 via coupling parts 29 and 30. The positioning projection part 50 may be formed in either of the heating element grip parts 27a and 27b. In this case, the inner diameter of the heating element grip part 27a, 27b needs to be preset largely considering the projection amount of the positioning projection part 50.

For example, in FIG. 31, the positioning projection part 50 is formed in the heating element grip part 27a far from the heating part 42. In FIG. 32, the positioning projection part 50 is formed in the heating element grip part 27b near to the heating part 42. In this case, the heating part 42 of the heating element 3 abuts the hollow part inner wall 2a of the oxygen sensing element 2 on the opposite side to the side where the coupling part 29 or 30 is positioned, whereby the heating element 3 is inclined to the hollow part inner wall 2a a little largely and the center axis O1 of the heating element 3 crosses the center axis O2 of the hollow part at a predetermined inclination θ, as shown in FIG. 33.

Figure 33:
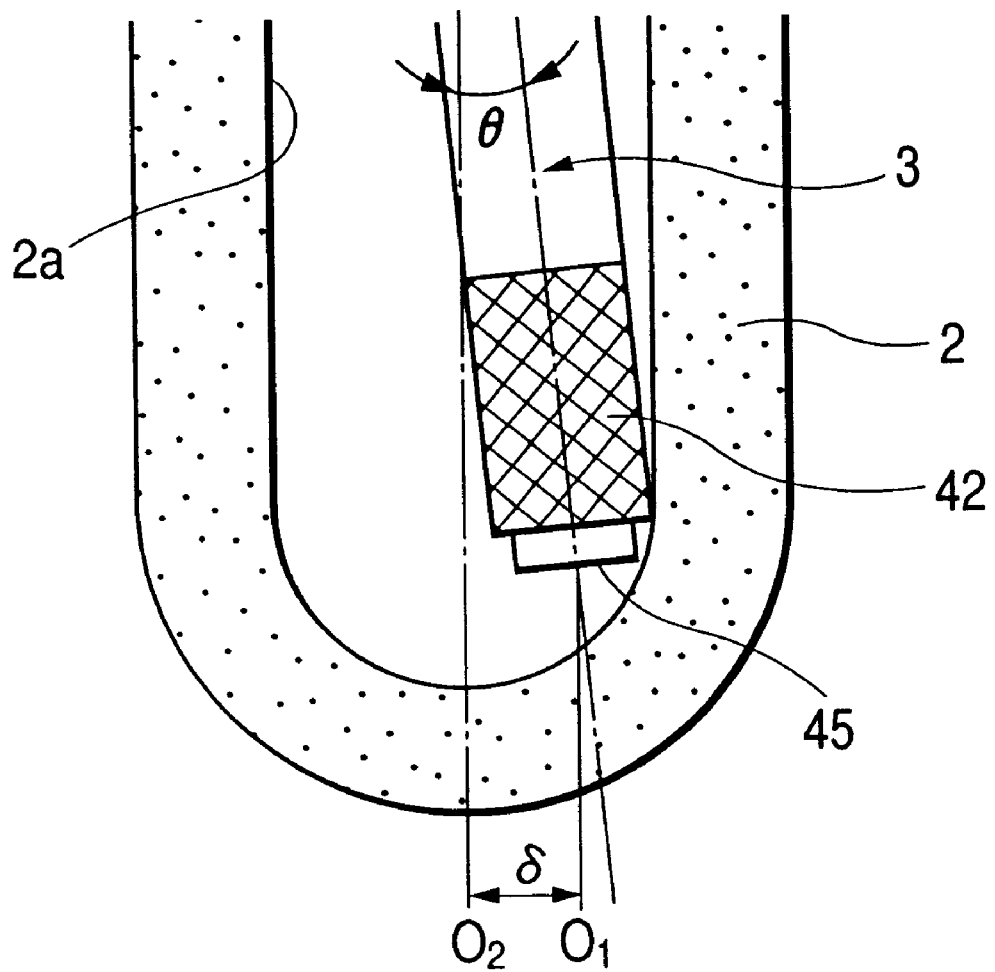
FIG. 33 is a partially sectional view to show the concept of the proximity of a heating element in FIG. 32.

In FIG. 33, for easy understanding, the gap between the heating element 3 and the oxygen sensing element 2 and the inclination θ are drawn bombastically. When the inner diameter of the element inner wall 2a is 2.8–3.2 mm and the outer diameter of the heating element 3 is 2.43–2.63 mm, it is advisable to set the offset amount δ of the center axis O1 in the proximity of the heating part 42 to the center axis O2 of the oxygen sensing element 2 and the inclination θ to about 0.085–0.385 mm and about 0.1°–0.5° respectively, for example, to provide the lateral strike structure reliably without producing an excessive press force between the heating element 3 and the oxygen sensing element 2.

Figure 34:
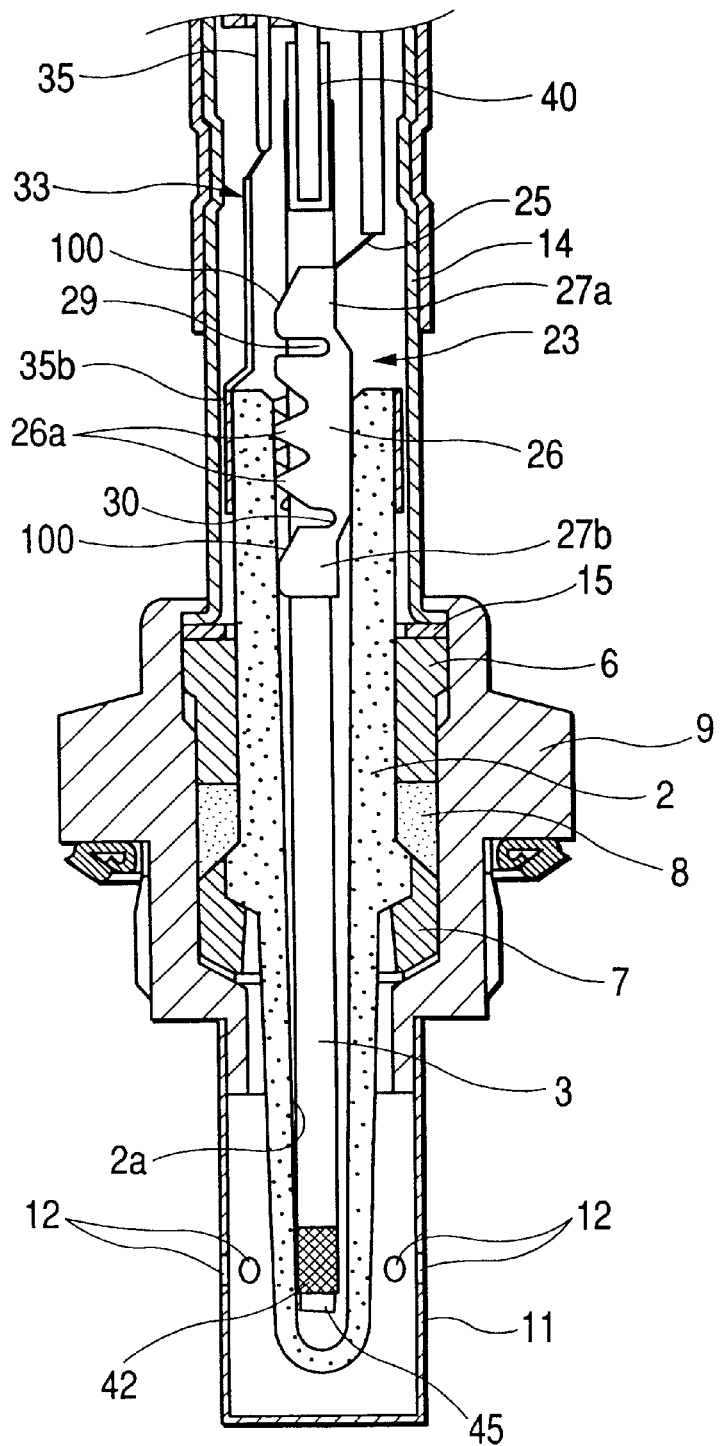
FIG. 34 is a longitudinal sectional view to show a third modified example of the oxygen sensor in FIG. 1.

Next, in a structure shown in FIG. 34, the terminal metal shell 23 is constituted by the internal electrode connection part 26 formed almost as in FIG. 1. In the axial direction of the heating element 3, the internal electrode connection part 26 is formed on one side with first heating element grip part 27a similar to that described above and formed on the other side with second heating element grip part 27b. Here, as shown in FIGS. 35A and 35B, the pair of the heating element grip parts 27a and 27b is coupled to the internal electrode connection part 26 so that the center axes of the heating element grip parts 27a and 27b are positioned on a common axis O10 offset from and almost parallel with center axis O11 of the hollow part of the oxygen sensing element 2.

Specifically, in the terminal metal shell 23, the first heating element grip part 27a and the second heating element grip part 27b are connected integrally to the periphery on the same side in the diametric direction of the heating element 3 by the first and second coupling parts 29 and 30 of narrow parts to the corresponding ends of the internal electrode connection part 26. The coupling parts 29 and 30 are bent inward in the diametric direction of the internal electrode connection part 26 to form stepped parts and the bend amount is adjusted, whereby the center axis O10 of the heating element grip parts 27a and 27b is offset by a predetermined offset amount d (as described later) in the opposite direction to the formation side of the coupling parts 29 and 30 almost in parallel with the center axis O11 of the hollow part of the oxygen sensing element 2. According to the structure, the heating element 3 can be held on the two grip parts 27a and 27b more stably.

Figure 36A:
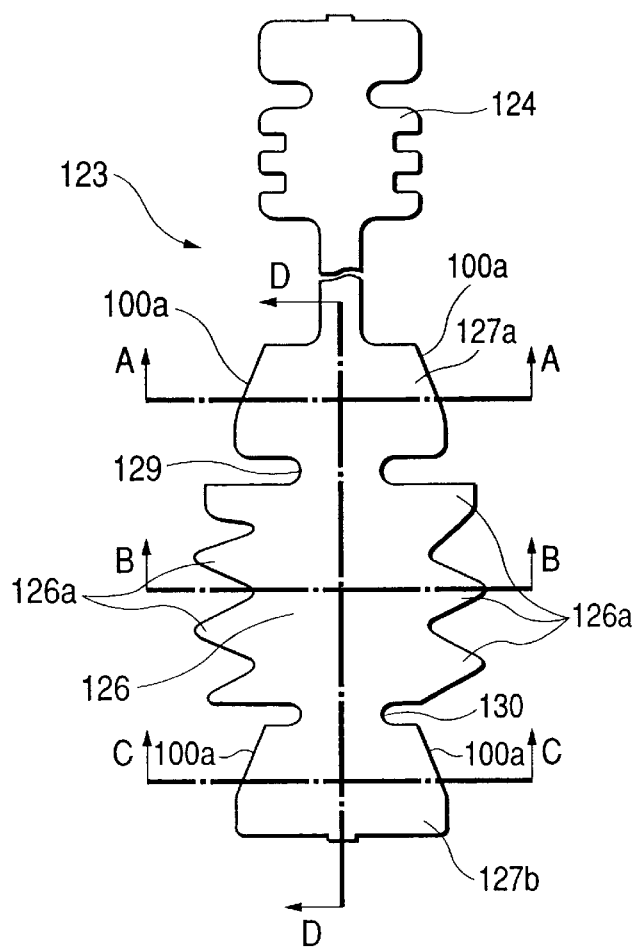
FIGS. 36A to 36E are drawings to show an example of a plate-like metal member to manufacture the terminal metal shell in FIG. 35.
Figure 36E:
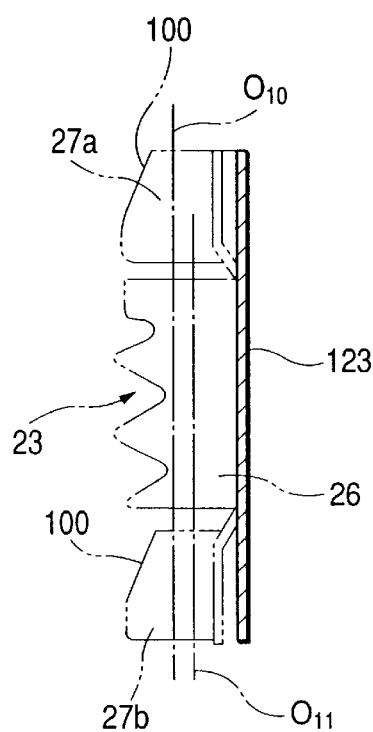
Figure 36B:
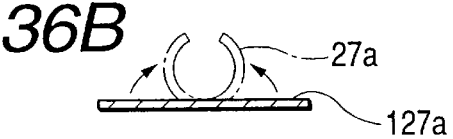
Figure 36C:
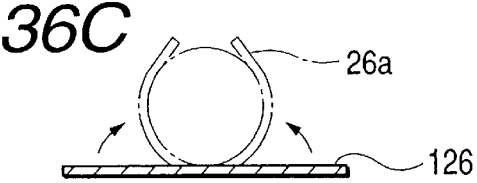
Figure 36D:
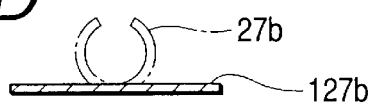
Figure 37:
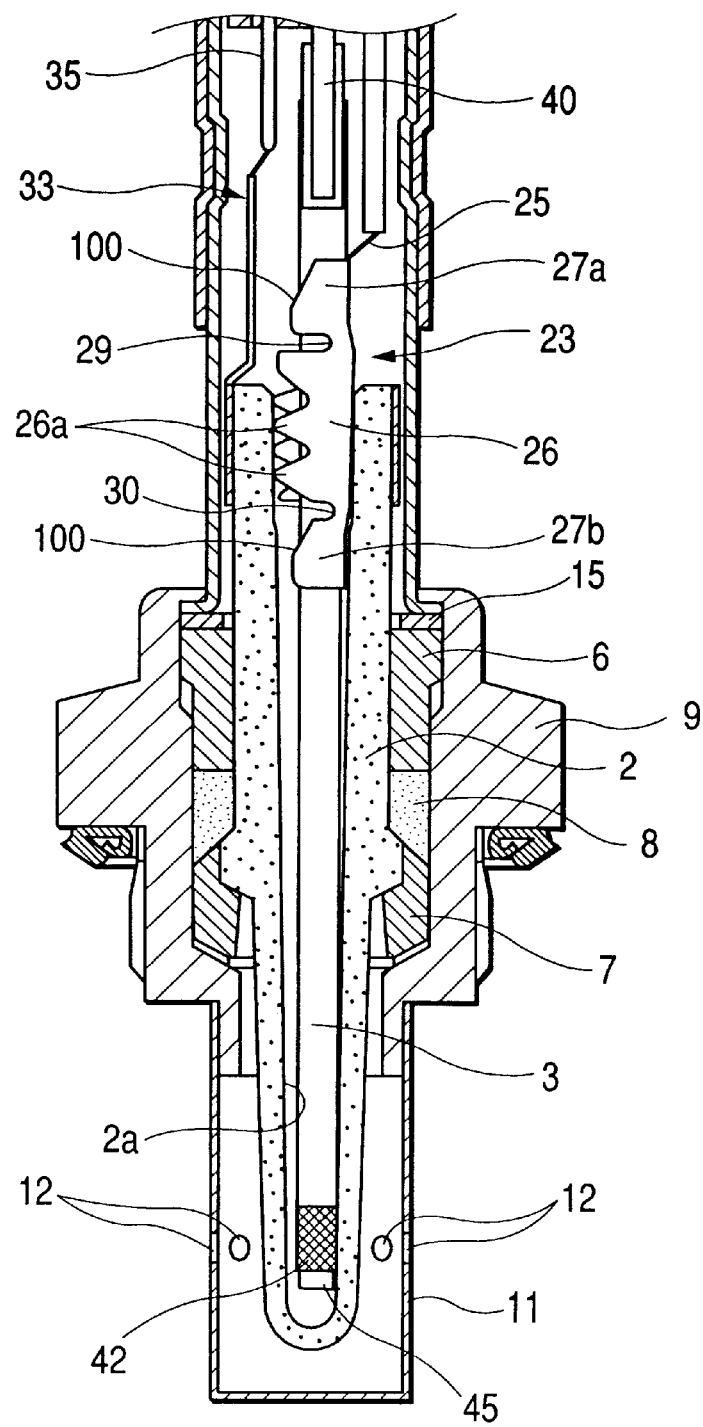
FIG. 37 is a longitudinal sectional view to show a fourth modified example of the oxygen sensor in FIG. 1.

The terminal metal shell 23 as described above can be manufactured by bending a plate-like metal member 123 shaped as shown in FIG. 36A, for example. That is, as shown in FIG. 36A, the plate-like metal member 123 is constituted by three plate-like parts 127a, 126, and 127b integrated by connection parts 129 and 130 to become the coupling parts 29 and 30 in the intermediate part in the width direction. As shown in FIGS. 36B to 36D, the portions projecting on both sides of the connection parts 129 and 130 are bent like a cylinder in the width direction, thereby forming first heating element grip part 27a, internal electrode connection part 26a, and second heating element grip part 27b. As shown in FIG. 36E, the coupling parts 29 and 30 are bent like stepped forms so that the center axis O10 of the heating element grip parts 27a and 27b is placed at a predetermined position.

In the plate-like metal member 123, both margins in the width direction of the plate-like parts (first plate-like parts) 127a and 127b to become the heating element grip parts 27a and 27b are bent and opposed to each other to form slit 101 and the end part of one of the margins is cut away slantingly to form the heating element insertion guide part 100.

Figure 38A:
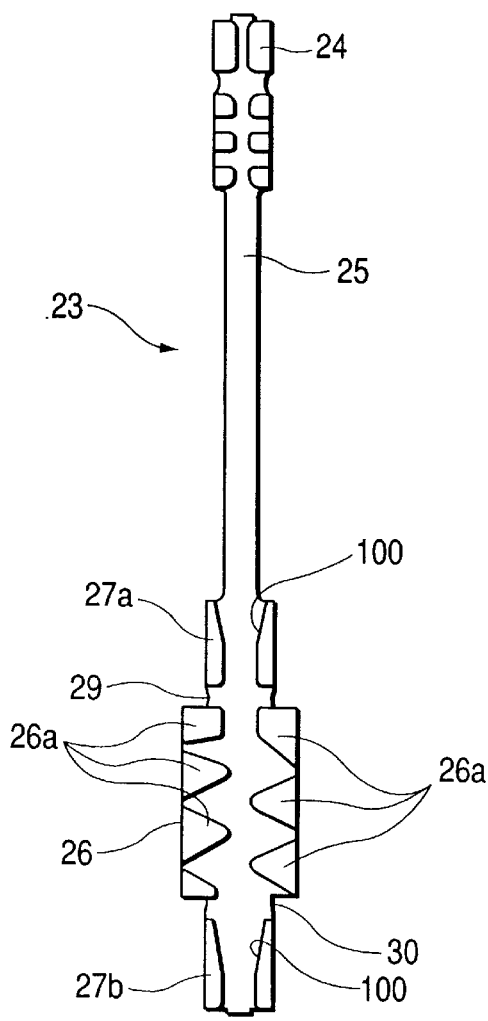
FIGS. 38A to 38C are drawings to show a discrete state of a terminal metal shell in FIG. 37.
Figure 38B:
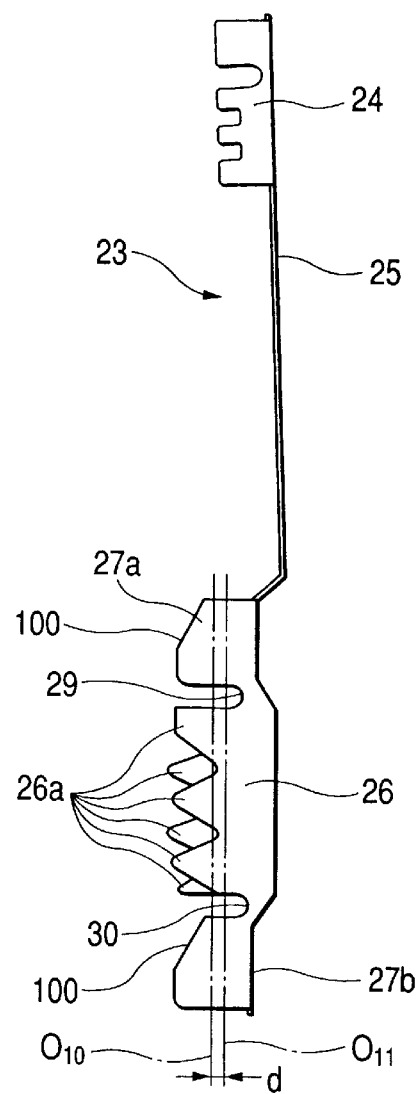
Figure 38C:
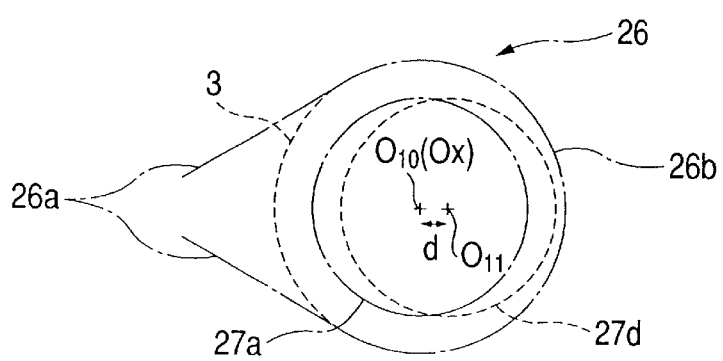

Next, in a structure in FIGS. 38A to 38C, first heating element grip part 27a and second heating element grip part 27b are formed as in the structure in FIGS. 35A and 35B, but the second heating element grip part 27b has the center axis O11 offset by distance d from the center axis O10 of the first heating element grip part 27a, as shown in FIG. 38B. That is, the first heating element grip part 27a and the second heating element grip part 27b are connected integrally to the periphery on the same side in the diametric direction of the heating element 3 by the first and second coupling parts 29 and 30 of narrow parts to the corresponding ends of the internal electrode connection part 26. The first and second coupling parts 29 and 30 are bent inward in the diametric direction of the internal electrode connection part 26 to form stepped parts and the bend amount is adjusted, whereby the offset amount d between the center axes O10 and O11 of the first heating element grip part 27a and the second heating element grip part 27b is adjusted. According to the structure, the heating element 3 is held in an inclination state by the two grip parts 27a and 27b offset from each other and is pressed against the element inner wall 2a, so that it can be held in the inclination state more stably and the lateral strike effect of the heating element 3 is accomplished more reliably.

Figure 39:
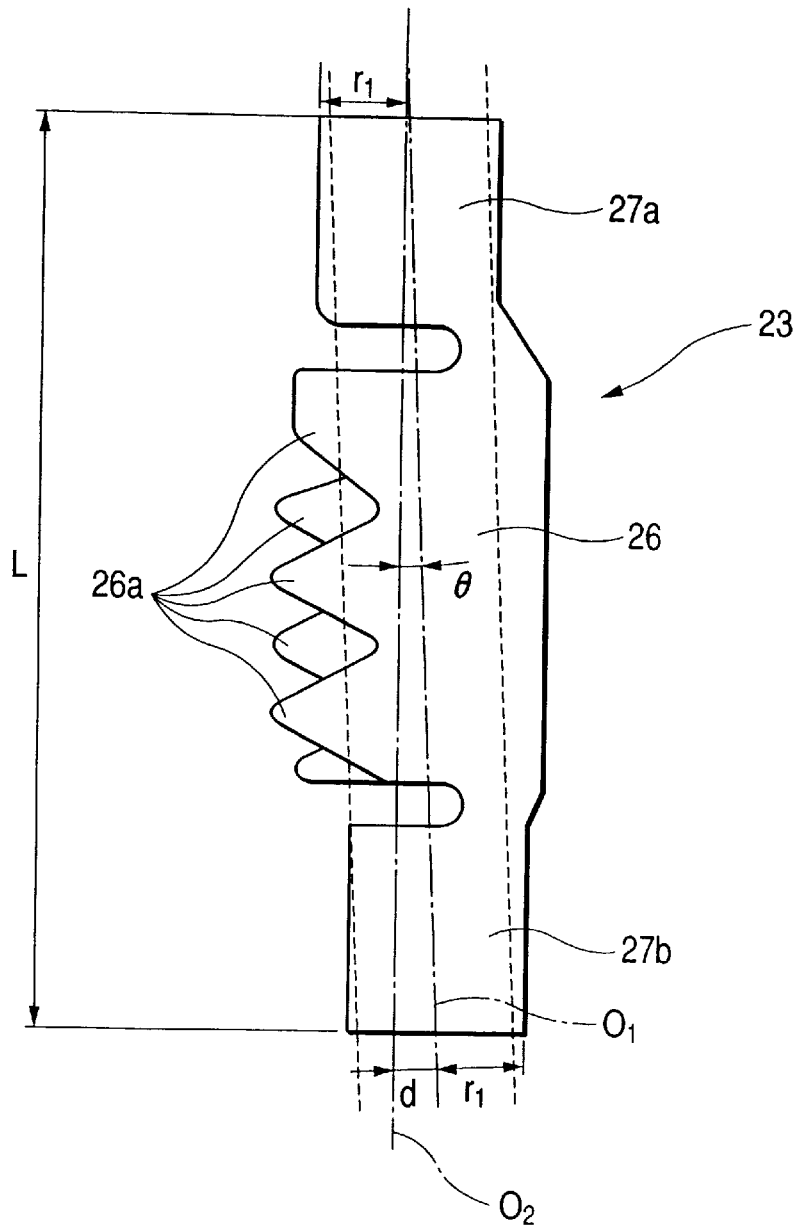
FIG. 39 is a drawing to show bombastically the effect of the terminal metal shell in FIG. 37.

Here, for example, the offset amount d between the center axes O10 and O11 of the first heating element grip part 27a and the second heating element grip part 27b can be set as follows: As shown bombastically in FIG. 39 for easy understanding, for example, when the inner diameter of the element inner wall 2a is 2.8–3.2 mm and the outer diameter of the heating element 3 is 2.43–2.63 mm, it is advisable to set the angle between the center axis O1 of the heating element 3 and the center axis O2 of the hollow part of the oxygen sensing element 2, θ, to about 0.1°–0.5° as described above. Assuming that the distance between axial end faces of the first heating element grip part 27a and the second heating element grip part 27b is L, tan θ=d/L and tan 0.1°=0.0017 and tan 0.5°=0.0087, thus d may be set so that 0.0017L≦d≦0.0087L.

Also in the structure, the two heating element grip parts 27a and 27b are formed each with heating element insertion guide part 100. That is, since the two grip parts 27a and 27b are provided and moreover are formed in offset relation from each other to hold the heating element 3 in the inclination state, the heating element 3 attempts to enter the lower grip part 27b in the offset state after it is inserted into the upper grip part 27a. Thus, the above-described problem of catching the heating element in the grip part easily occurs particularly in the lower grip part 27b. Then, the heating element insertion guide parts 100 are formed as described above, whereby the heating element 3 can be smoothly fitted into the terminal metal shell 23 also in the structure. Since the above-described problem of catching the heating element in the grip part occurs less in the upper grip part 27a than the lower grip part 27b, only the lower grip part 27b may be formed with the heating element insertion guide part 100.

Figure 40:
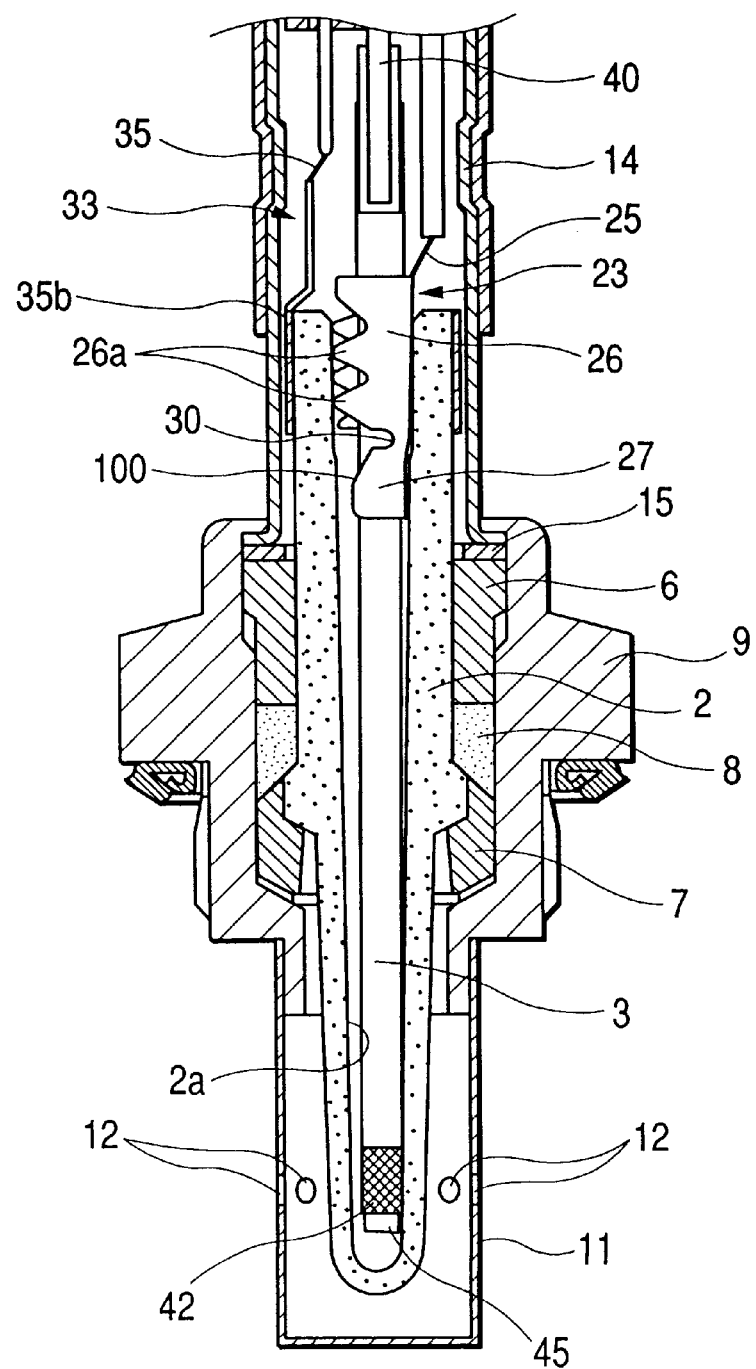
FIG. 40 is a longitudinal sectional view to show a fifth modified example of the oxygen sensor in FIG. 1.

In a structure shown in FIG. 40, only one heating element grip part 27 is provided for the internal electrode connection part 26 as in the structure in FIG. 1, but the positioning projection part 50 is not formed unlike the structure in FIG. 1. According to the structure in FIG. 40, the heating element 3 is gripped by the one grip part 27 with some motion freedom in the direction crossing the axis. Therefore, if the heating element 3 is inserted into the hollow part of the oxygen sensing element 2 together with the terminal metal shell 23, as the tip of the heating element 3 comes in contact with the inner wall of the oxygen sensing element 2, the heating element 3 is positioned in parallel with the inner wall accordingly and a larger effect of shortening the oxygen sensor activation time can be expected. In this case, ΔD or ΔD/DB is adjusted in the above-described range, whereby the tip of the heating element 3 becomes more easily parallel with the inner wall of the hollow part of the oxygen sensing element 2 and the effect of shortening the oxygen sensor 1 activation time can be enhanced furthermore.

As another effect, when the oxygen sensor 1 is assembled, an excessive lateral force via the terminal metal shell 23 becomes hard to act on the heating element 3 and in turn damage to the heating element 3, etc., at the assembling time can be prevented. Further, the length of the terminal metal shell 23 in the axial direction of the heating element can be shortened and in turn the length of the oxygen sensor in the axial direction of the heating element can be shortened for making the oxygen sensor compact.

Figure 41:
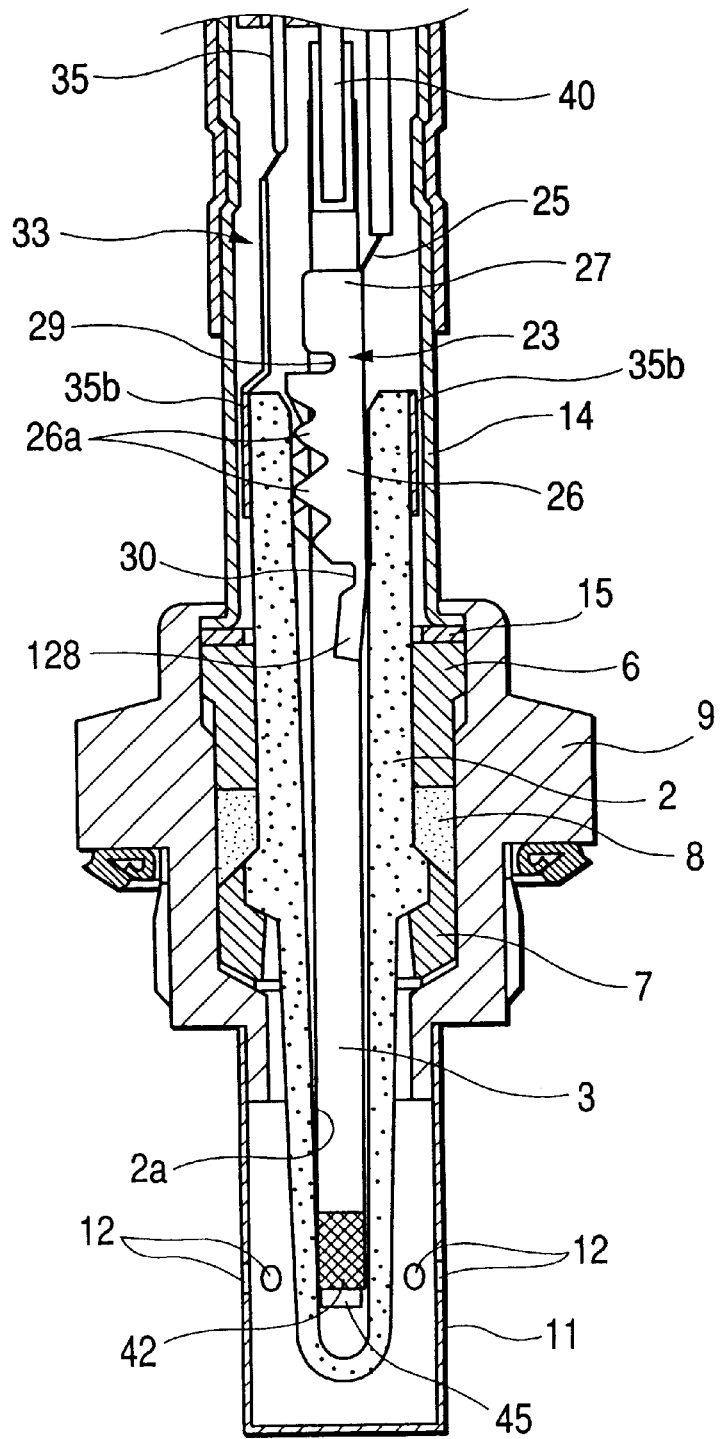
FIG. 41 is a longitudinal sectional view to show a sixth modified example of the oxygen sensor in FIG. 1.

Next, in a structure shown in FIG. 41, the heating element grip part 27 is connected to the axial rear end of the internal electrode connection part 26 and a guide part 128 is connected to the front end. The guide part 128 has a transverse section shaped almost like a half circle and is inclined inward by a predetermined angle relative to the center axis of the terminal metal shell 23, more particularly, the center axis of the heating element grip part 27 and the internal electrode connection part 26, so that it presses the heating element 3 against the element inner wall 2a in a direction perpendicular to the axial direction of the heating element 3.

At least one of the following aspects of the invention can be added to the structure of the oxygen sensor according to the present invention:

Aspect (A) of Invention

An oxygen sensor of the invention is constituted by an oxygen sensing element shaped like a shaft, a cylindrical casing for housing the oxygen sensing element, a filter assembly being placed almost coaxially with the casing as a cylindrical body separate from the casing and coupled to the casing from the rear while allowing leads from the oxygen sensing element to extend to the rear outside of the filter assembly, and a coupling part for coupling the filter assembly and the casing. The filter assembly is constituted by a filter holding part making a cylindrical form almost coaxially coupled to the casing from the rear of the casing, having an inside communicating with the inside of the casing, and being formed in a wall with one or more gas introduction holes, a filter being placed so as to block the gas introduction hole or holes in the filter holding part from the inner or outer face side for rejecting permeation of liquid and allowing gas to pass through, and an auxiliary filter holding part for fixing the filter to the filter holding part. Outside air is introduced into the casing through the filter and the gas introduction hole.

In the oxygen sensor, the casing and the filter assembly can be formed as separate bodies and the filter assembly can be placed on the rear of the casing, then the coupling part is formed, thereby coupling the casing and the filter assembly.

The oxygen sensor is characterized by the fact that the ventilation structure containing the filter is formed as the filter assembly separate from the casing and is coupled to the casing. Thus, the following advantages can be accomplished:

(1) The filter assembly can be assembled independently of fitting of the oxygen sensing element, etc., into the casing, thus the sensing element leads, for example, do not become obstruction and the assembling work can be carried out extremely efficiently.

(2) Since fitting of parts into the casing can be performed in parallel with assembling of the filter assembly, productivity improves dramatically. Even if a fitting failure, etc., of the filter occurs, if it can be found at the stage of the filter assembly, the failure does not affect the sensor finished product and waste, etc., of parts is hard to occur.

The filter assembly is constituted by a filter holding part being placed coaxially and integrally with the rear of the casing so that the inside of the filter holding part communicates with the inside of the casing and formed in a wall with one or more gas introduction holes, a filter being placed so as to block the gas introduction hole or holes on the outside of the filter holding part for rejecting permeation of liquid and allowing gas to pass through, and an auxiliary filter holding part being formed like a cylinder placed on the outside of the filter and formed in a wall with one or more auxiliary gas introduction holes for sandwiching the filter between the auxiliary filter holding part and the filter holding part. In this case, outside air is introduced into the casing through the auxiliary gas introduction hole, the filter, and the gas introduction hole. That is, the filter can be held reliably by the auxiliary filter holding part and the filter holding part and the filter is also easily fitted into the filter holding part. For example, if the filter is formed like a cylinder, it is fitted into the outside of the filter holding part, further the auxiliary filter holding part is fitted from the outside, and the holding part coupling part for coupling the filter holding part and the auxiliary filter holding part may be formed at a position not interfering with the gas introduction hole or the auxiliary gas introduction hole.

A plurality of the gas introduction holes and a plurality of the auxiliary gas introduction holes can be made with a predetermined spacing along a circumferential direction in positional relationship corresponding to each other in an axial intermediate part in the filter holding part and the auxiliary filter holding part, whereby outside air can be uniformly introduced into the casing from the filter assembly side. For example, cylindrical filter can be placed on the outside of the filter holding part so as to surround the filter holding part in the circumferential direction and the auxiliary filter holding part can be formed with an annular filter crimp part along the circumferential direction of the auxiliary filter holding part as a holding part coupling part by crimping the auxiliary filter holding part toward the filter holding part with the filter between. Assembling of the filter assembly is furthermore facilitated by making the holding part coupling part the annular filter crimp part. The annular filter crimp part can be formed on both sides sandwiching axially the gas introduction hole and auxiliary gas introduction hole row. In this case, in each crimp part, the filter margin is sandwiched between the auxiliary filter holding part and the filter holding part, whereby a passage bypassing the filter margin from the auxiliary gas introduction hole and leading to the gas introduction hole in the filter holding part is hard to form and the possibility that water, etc., will pass through the passage and leak into the filter holding part and in turn the casing is also lessened.

If the filter is shaped like a cylinder as described above and is placed along the outer periphery of the filter holding part, the filter crimp part can be formed along the circumferential direction on the rear end of the auxiliary filter holding part. A filter check part to visually check the filter positioned between the auxiliary filter holding part and the filter holding part can be formed on the rear end of the auxiliary filter holding part. In doing so, the following advantage can be provided: When the cylindrical filter is fitted into the outside of the filter holding part and in this state, further the auxiliary filter holding part is fitted while it is relatively moved axially to the filter holding part, the filter can move in association with the auxiliary filter holding part, causing a position shift. In this case, in this state, if the filter cramp part is formed, the filter is detached from the filter cramp part and sealing becomes incomplete. However, such a crimp failure of the filter can be easily found because the filter can be visually checked as described above in the filter check part.

To form the filter crimp part in the front end margin of the auxiliary filter holding part, the filter crimp part can also be formed with a filter check exposure part for exposing the filter partially. In doing so, whether or not the filter is normally crimped can also be determined easily in the front end margin of the auxiliary filter holding part.

Next, the filter assembly can be coupled to the casing by various methods. For example, the filter holding part can be placed so as to overlap the casing at the tip of the filter holding part from the outside and an annular assembly coupling crimp part as the coupling part can be formed in the circumferential direction of the filter holding part and the casing by crimping the filter holding part toward the casing in the overlap and can press the inner peripheral surface of the filter holding part against the outer peripheral surface of the casing in hermetic relation. That is, the filter assembly can be easily fitted into the casing by the assembly coupling crimp part. An annular weld part (for example, resistance weld part or laser weld part) may be formed in place of or together with the crimp part.

Next, the filter holding part can have the axial front relative to a stepped part formed in an axial intermediate part of the filter holding part as a first portion and the rear as a second portion so that the second portion is made smaller in diameter than the first portion. In this case, the gas introduction hole can be made in a wall of the second portion. On the other hand, the rear end part of the casing can be inserted into the first portion of the filter holding part to a position at which it abuts directly or indirectly via a member the stepped part. The casing overlap is formed in the first portion and the assembly coupling crimp part (or weld part) can be formed here.

According to the structure of the oxygen sensor, the stepped part can be used to easily positioning axially the filter holding part to the casing. If a gas introduction hole is made in the small-diameter second portion and the filter and the auxiliary filter holding part are fitted into the hole from the outside, when the filter and the filter holding part are fitted in order from the upper side, for example, in a state in which the filter holding part is upright with the second portion up, the filter and the filter holding part can be stricken against the stepped part and stopped. Thus, assembling of the filter assembly is facilitated furthermore. In this case, the inner diameter of the auxiliary filter holding part needs to be preset smaller than the outer diameter of the first portion.

The oxygen sensor can further include a ceramic separator formed with a plurality of lead insertion holes axially penetrating the ceramic separator for inserting leads from the oxygen sensing element. In this case, the ceramic separator can be placed so that the rear thereof enters the inside of the filter holding part in the axial direction of the oxygen sensing element and the front enters the inside of the casing. A part of the ceramic separator is entered in the inside of the filter holding part, whereby free space formed in the filter holding part on the rear of the ceramic separator becomes small and in turn the axial length of the oxygen sensor can be shortened accordingly for making the whole oxygen sensor compact.

In this case, the ceramic separator can be formed with a separator support part projecting from an outer peripheral surface of the ceramic separator, for example, like a flange at an intermediate position in the axial direction thereof. The ceramic separator can be placed so as to abut directly or indirectly via a member the rear end face of the casing in the separator support part in a state in which a portion positioned ahead the separator support part is entered in the rear end inside of the casing, and can be placed in a state in which a portion positioned behind the separator support part is projected to the outside of the casing. If the stepped part is formed in the axial intermediate part, the filter holding part can be placed so as to allow the projection of the ceramic separator to enter the inside of the second portion and cover it and abut directly or indirectly via a member the separator support part in the stepped part from an opposite side to the casing. That is, the separator support part is sandwiched between the end face of the casing and the stepped part of the filter holding part, whereby the ceramic separator can be supported more stably in the casing and in turn trouble such as breaking or chipping of the ceramic separator because of a rattle becomes hard to occur.

For example, the ceramic separator can be formed with a ventilation communication part axially penetrating the ceramic separator from the rear end face to the front end face thereof for introducing outside air flowing in through the gas introduction hole into the inside of the casing, whereby outside air as the reference gas can be introduced into the oxygen sensing element reliably and promptly. If water drops, etc., are entered through the gas introduction hole for some reason, there is a possibility that the water drops will leak into the oxygen sensing element through the ventilation communication part. In this case, the rear end face of the ceramic separator can be positioned behind the gas introduction hole. In doing so, if water drops are entered, they must be bypassed to the rear end face of the ceramic separator to leak into the casing from the ventilation communication part, thus the possibility that the water drops will leak into the oxygen sensing element can be more lessened.

Aspect (B) of the Invention

An oxygen sensor of the invention is constituted by an oxygen sensing element shaped like a shaft, a cylindrical casing for housing the oxygen sensing element, and a gas introduction structure for introducing outside air into the casing. The gas introduction structure has a filter holding part making a cylindrical form coaxial with the casing on the rear of the casing, having an inside communicating with the casing, and being formed in a wall with one or more gas introduction holes and a filter being placed so as to block the gas introduction hole or holes of the filter holding part for rejecting permeation of liquid and allowing gas to pass through, for introducing outside air into the casing through the filter and the gas introduction hole or holes. Placed on the outside of the gas introduction structure is a protective cover formed like a cylinder for covering the outside of the gas introduction structure for blocking or suppressing a direct jet of liquid drops to the filter or deposition of deposits of oil, dirt, etc., on the filter.

That is, the filter for rejecting permeation of liquid and allowing gas to pass through is placed in the gas introduction structure and further the protective cover is placed on the outside thereof, whereby the entry of water drops, etc., in the casing becomes harder to occur. Thus, if the oxygen sensor is attached to a part in the proximity of a tire of a vehicle, when the vehicle is driven while strongly jumping up water in a pool, etc., or high-pressure water is stricken directly to the filter at the vehicle washing time, the entry of water drops, etc., in the oxygen sensor can be prevented effectively using the filter and the protective cover in combination.

The gas introduction structure can be constituted by a filter holding part being placed coaxially and integrally with the rear of the casing and formed in a wall with one or more gas introduction holes, a filter being placed so as to block the gas introduction hole or holes on the outside of the filter holding part for rejecting permeation of liquid and allowing gas to pass through, and an auxiliary filter holding part being formed like a cylinder placed on the outside of the filter and formed in a wall with one or more auxiliary gas introduction holes for sandwiching the filter between the auxiliary filter holding part and the filter holding part. In this case, outside air can be introduced into the casing through the auxiliary gas introduction hole, the filter, and the gas introduction hole. That is, the filter can be held reliably by the auxiliary filter holding part and the filter holding part and the filter is also easily fitted into the filter holding part. For example, if the filter is formed like a cylinder, it is fitted into the outside of the filter holding part, further the auxiliary filter holding part is fitted from the outside, and the holding part coupling part for coupling the filter holding part and the auxiliary filter holding part may be formed at a position not interfering with the gas introduction hole or the auxiliary gas introduction hole.

The protective cover can have both side portions sandwiching the gas introduction hole in an axial direction joined to the outer face of the filter holding part by a cover joint part with a gas retention space produced between the protective cover and the filter at a position corresponding to the gas introduction hole, and an external communication part for allowing the gas retention space to communicate with the outside and introducing outside air into the gas retention space can be provided, whereby outside air as the reference gas is introduced into the inside of the protective cover through the external communication part and can smoothly pass through the filter as the gas retention space is formed, so that the outside air (reference gas) can be introduced into the casing without a hitch although the protective cover is provided.

In this case, the cover joint part can be formed annularly along the circumferential direction of the protective cover and the external communication part can be formed like a passage crossing the annular cover joint part between the protective cover and the filter holding part. That is, the entry of water drops, etc., into the inside of the cover member becomes hard to occur owing to the annular cover joint part and moreover as the external communication part is formed like a passage crossing the annular cover joint part, the outside air can be introduced into the cover member without a hitch.

The structure can be realized comparatively easily as follows: A plurality of predetermined-length grooves as the external communication part extending in the axial direction of the filter holding part are formed with a predetermined spacing along the circumferential direction on the outer peripheral surface of the filter holding part ahead the air introduction hole. The cover joint part is an annular crimp part formed so as to cross the grooves and leave a gap between the protective cover and the filter holding part at the bottom of each groove by crimping the protective cover toward the filter holding part. Thus, outside air is introduced into the gas retention space through the grooves from front opening of the gap formed between the protective cover and the filter holding part. In this case, the crimp pressure and the groove depth may be adjusted to such a degree that the gap can be provided at the groove bottom.

The front end margin of the protective cover can be extended to the front by a predetermined length from the end of each groove. Thus, the probability that if the oxygen sensor is caught in a splash, etc., water drops, etc., enter the inside of the protective cover can be more lessened.

Next, the filter holding part can have the axial front relative to a stepped part formed in an axial intermediate part of the filter holding part as a first portion and the rear as a second portion so that the second portion is made smaller in diameter than the first portion. In this case, the gas introduction hole is made in a wall of the second portion. According to the structure of the oxygen sensor, when the filter and the filter holding part are fitted in order from the upper side, for example, in a state in which the filter holding part is upright with the second portion up, the filter and the filter holding part can be stricken against the stepped part and stopped. Thus, assembling of the gas introduction structure is facilitated furthermore. In this case, the inner diameter of the auxiliary filter holding part needs to be preset smaller than the outer diameter of the first portion.

In the structure of the oxygen sensor, the grooves can be formed on the outer peripheral surface of the first portion. The protective cover is fixedly secured to the first portion by the annular crimp part in the front end part and is fixedly secured to the outer peripheral surface of an end part of the second portion by another crimp part in the rear end part. Thus, the gas retention space can be easily formed between the protective cover and the second portion of smaller diameter, of the filter holding part.

The oxygen sensor can further include a ceramic separator being formed with a plurality of lead insertion holes axially penetrating the ceramic separator for inserting leads from the oxygen sensing element. The ceramic separator can be formed with a separator support part like a flange projecting from the outer peripheral surface of the ceramic separator at an intermediate position in the axial direction thereof. The ceramic separator is placed so as to abut directly or indirectly via a member the rear end face of the casing in the separator support part in a state in which a portion positioned ahead the separator support part is entered in the rear end inside of the casing. The annular crimp part as the cover joint part can be formed at a position corresponding to the outer peripheral surface of the flange-like separator support part. Thus, the compression force when the crimp part is formed can be received on the outer peripheral surface of the flange-like separator support part, so that the crimp part can be formed reliably.

Aspect (C) of Invention

An oxygen sensor of the invention is constituted by an oxygen sensing element shaped like a shaft, a cylindrical casing for housing the oxygen sensing element, and a gas introduction structure. The gas introduction structure is constituted by a filter holding part making a cylindrical form almost coaxial with the casing on the rear of the casing, having an inside communicating with the inside of the casing, and being formed in a wall with one or more gas introduction holes, a filter being placed so as to block the gas introduction hole or holes on the outside of the filter holding part for rejecting permeation of liquid and allowing gas to pass through, and an auxiliary filter holding part being formed like a cylinder placed on the outside of the filter and formed in a wall with one or more auxiliary gas introduction holes for sandwiching the filter between the auxiliary filter holding part and the filter holding part, for introducing outside air into the casing through the auxiliary gas introduction hole, the filter, and the gas introduction hole. The filter comes in intimate contact with the inner face of the auxiliary filter holding part at least in surroundings of the auxiliary gas introduction hole and a predetermined gap is formed between the outer face of the filter holding part and the filter at least in surroundings of the gas introduction hole.

In the described oxygen sensor, distribution resistance of outside air passing through the filter is lessened because the annular gap is made inside, and the outside air can be smoothly introduced into the casing through the gas introduction holes. On the other hand, the outer face of the filter adheres closely to the inner face of the auxiliary filter holding part, thus dust, oil, water drops, etc., become hard to remain between the filter and the auxiliary filter holding part through the auxiliary gas introduction hole and in turn degradation of oil or water repellency on the outer face of the filter is stopped or suppressed, always providing good ventilation. Since oil becomes hard to remain, the entry of vapor of oil evaporated at high temperature into the sensor through the filter is suppressed. Thus, for example, if the reference gas temperature becomes high, sensor output degradation becomes hard to occur.

The auxiliary filter holding part can be formed with filter crimp parts for coupling the auxiliary filter holding part to the filter holding part via the filter on both axial sides with the auxiliary gas introduction hole between. A portion positioned between the filter crimp parts of the auxiliary filter holding part can be bent outward together with the filter to form a convex form and the auxiliary gas introduction hole can be made in the top of the convex part. The top of the convex part can be flattened at least in surroundings of the auxiliary gas introduction hole and the inner face of the filter holding part can be brought into intimate contact with the filter in the flattened part. That is, if filter crimp parts are formed on both sides with the auxiliary gas introduction hole between, the portion between the crimp parts of the auxiliary filter holding part is bent outward to form a convex form, as described above. However, the top of the convex part is flattened, whereby the intimate contact structure between the auxiliary filter holding part and the filter can be provided easily. For example, a method of forming filter crimp parts while regulating convex part swelling on the top of the convex part using a flattening member is available as a method of forming the flattened portion in the auxiliary filter holding part.

In this case, in the portion sandwiched between the crimp parts, the auxiliary filter holding part and the filter holding part can be bent outward larger than the corresponding portion of the filter holding part and the gap can be formed between the filter holding part and the filter based on the bend amount difference between the auxiliary filter holding part and the filter holding part. That is, the auxiliary filter holding part is compressed and deformed comparatively largely in association with crimp and the bend amount in the convex part also grows, but the inner filter holding part is not so compressed and the bend amount is also small. On the other hand, the filter, which is flexible, is bent outward following the auxiliary filter holding part. Resultantly, the gap can be easily formed between the filter holding part and the filter based on the bend amount difference between the filter holding part and the auxiliary filter holding part.

A plurality of the gas introduction holes and a plurality of the auxiliary gas introduction holes can be made with a predetermined spacing along a circumferential direction in positional relationship corresponding to each other in an axial intermediate part in the filter holding part and the auxiliary filter holding part, whereby outside air can be uniformly introduced into the casing from the gas introduction structure side. For example, cylindrical filter can be placed on the outside of the filter holding part so as to surround the filter holding part in the circumferential direction and the auxiliary filter holding part can be formed with an annular filter crimp part along the circumferential direction of the auxiliary filter holding part as a holding part coupling part by crimping the auxiliary filter holding part toward the filter holding part with the filter between. Specifically, the annular filter crimp part can be formed on both sides sandwiching axially the gas introduction hole and auxiliary gas introduction hole row. In this case, in each crimp part, the filter margin is sandwiched between the auxiliary filter holding part and the filter holding part, whereby a passage bypassing the filter margin from the auxiliary gas introduction hole and leading to the gas introduction hole in the filter holding part is hard to form and the possibility that water, etc., will pass through the passage and leak into the filter holding part and in turn the casing is also lessened. In this case, the convex part is formed annularly between the crimp parts, the top of the convex part is flattened annularly, and the auxiliary gas introduction holes are made in the flattened part.

The filter holding part may be formed with a concave part dented inward at least in surroundings of the gas introduction hole and the gap may be formed between the filter holding part and the filter in the concave part. In this case, the concave part may be formed like a dimple provided by denting the periphery of the gas introduction hole or formed annularly along the arrangement direction of the gas introduction holes.

Aspect (D) of Invention

An oxygen sensor of the invention is constituted by an oxygen sensing element shaped like a shaft, a cylindrical casing for housing the oxygen sensing element, and a cover member being placed coaxially with the casing so that the inside of the cover member communicates with the casing and coupled to the casing from the axial rear. The cover member is placed so as to overlap the casing on the axial front of the cover member from the outside. The overlap is formed with a main crimp part being formed annularly in the circumferential direction of the cover member and the casing by crimping the cover member toward the casing and a rotation prevention part for preventing the cover member and the casing from relatively rotating around the axis of the cover member and the casing in the annular main crimp part.

According to the structure of the oxygen sensor, in the main crimp part, the contact face between the casing and the cover member becomes cylindrical, thus excellent hermeticity is provided and water, etc., can be reliably prevented from leaking into the casing from the space between the casing and the cover member. The rotation prevention part is formed together with the main crimp part, whereby a twist force around the axis acts on the space between the casing and the cover member, relative rotation is hard to occur therebetween and in turn the hermeticity in the main crimp part can be made more reliable.

If the rotation prevention part is an auxiliary crimp part formed by crimping the cover member toward the casing at least on one side of the main crimp part in the axial direction of the cover member, it can be easily formed and is also excellent in the rotation prevention effect. Specifically, the auxiliary crimp part can be formed to be adjacent to the main crimp part with a predetermined spacing therebetween in the axial direction of the cover member and can be formed annularly along the circumferential direction of the cover member. The annular auxiliary crimp part is formed to be adjacent to the main crimp part, whereby the rotation prevention effect can be enhanced furthermore. In this case, more specifically, the auxiliary crimp part can be made polygonal in axis cross section. In doing so, the contact face between the casing and the cover member becomes like an angular cylinder, and relative rotation between the casing and the cover member if a twist force acts becomes extremely hard to occur.

Preferably, the auxiliary crimp part is formed on the side near to the oxygen sensing element rather than the main crimp part. That is, since the tip of the oxygen sensor can be exposed to high temperature, the positional relationship in which the main crimp part where hermeticity is prioritized is away from such a heat source is more desirable.

The main crimp part and the auxiliary crimp part can be formed in batch using two crimp punch units each containing a plurality of crimp punches for compressing the cover member from the circumferential outside, the crimp punch units being spaced from each other at a predetermined distance in the axial direction of the cover member. According to the method, the main crimp part and the auxiliary crimp part are formed at the same time by executing one crimping step, thus not only efficiency, but also the following advantage can be accomplished: Because of crimp punch compression, the cover member digs locally in the casing and is pressed thereagainst to form the crimp part. A crease part or a relief part accompanying the dig deformation is easily formed in the cover member in the surroundings of the press part. If the main crimp part and the auxiliary crimp part are formed in sequence, a crease part or a relief part caused by the crimp part formed later has an effect on the previously formed crimp part, impairing hermeticity. However, if both the crimp parts are formed at the same time as described above, the effect of a crease part or a relief part can be pooled in the area between the crimp parts and sufficient intimate contact, namely, hermeticity can be provided in the crimp parts.

The cover member of the oxygen sensor can be the filter assembly (in aspect (A) of the invention) being placed almost coaxially with the casing as a cylindrical body separate from the casing and coupled to the casing from the rear while allowing leads from the oxygen sensing element to extend to the rear outside of the filter assembly.

Aspect (E) of Invention

An oxygen sensor of the invention is constituted by an oxygen sensing element shaped like a shaft, a cylindrical casing for housing the oxygen sensing element, and a gas introduction structure. The gas introduction structure is constituted by a filter holding part making a cylindrical form almost coaxial with the casing on the rear of the casing, having an inside communicating with the inside of the casing, and being formed in a wall with one or more gas introduction holes, a filter being placed so as to block the gas introduction hole or holes on the outside of the filter holding part for rejecting permeation of liquid and allowing gas to pass through, and an auxiliary filter holding part being formed like a cylinder placed on the outside of the filter and formed in a wall with one or more auxiliary gas introduction holes for sandwiching the filter between the auxiliary filter holding part and the filter holding part, for introducing outside air into the casing through the auxiliary gas introduction hole, the filter, and the gas introduction hole. The filter holding part has the axial front relative to a stepped part formed in an axial intermediate part of the filter holding part as a first portion and the rear as a second portion so that the second portion is made smaller in diameter than the first portion, and the gas introduction hole is made in a wall of the second portion. The auxiliary filter holding part is placed so as to spread across the first and second portions of the filter holding part. A main coupling part for coupling the filter holding part and the auxiliary filter holding part to each other with the filter between is formed at a position corresponding to the second portion. An auxiliary coupling part for coupling the filter holding part and the auxiliary filter holding part to each other is formed at a position corresponding to the first portion.

In the described oxygen sensor, the filter holding part consists of at least two portions of the first portion and the second portion different in diameter and adjacent to each other via the stepped part, the auxiliary filter holding part is shaped like a cylinder spreading across the two portions, and the main coupling part is formed in the second portion. In addition, the auxiliary coupling part is formed in the first portion. Thus, if a twist force around the axis is added to the space between the auxiliary filter holding part and the filter holding part, relative rotation is hard to occur therebetween. Resultantly, the seal of the filter sandwiched between the auxiliary filter holding part and the filter holding part is hard to break and the entry of water drops, etc., into the casing is hard to occur.

In the structure of the oxygen sensor, the filter can be placed so as to circumferentially surround only the second portion of the filter holding part. In this case, the main coupling part can be an annular main crimp part formed along the circumferential direction of the second portion by crimping the auxiliary filter holding part toward the second portion of the filter holding part with the filter between. The auxiliary coupling part can be an annular auxiliary crimp part formed along the circumferential direction of the first portion by directly crimping the auxiliary filter holding part toward the first portion of the filter holding part. According to the structure of the oxygen sensor, the main coupling part and the auxiliary coupling part can be easily formed by crimping and moreover the filter sealability between the auxiliary filter holding part and the filter holding part can be well provided. In the auxiliary crimp part, no filter intervenes between the auxiliary filter holding part and the filter holding part and both are directly crimped, so that the strength against twist can be enhanced furthermore.

A plurality of the gas introduction holes and a plurality of the auxiliary gas introduction holes can be made with a predetermined spacing along a circumferential direction in positional relationship corresponding to each other in an axial intermediate part in the filter holding part and the auxiliary filter holding part. The main crimp part can contain two crimp parts formed on both sides with the row of the gas introduction holes or the auxiliary gas introduction holes between. According to the structure of the oxygen sensor, outside air can be uniformly introduced into the casing in the gas introduction structure. The filter sealability can be better provided by the two main crimp parts.

Aspect (F) of Invention

An oxygen sensor of the invention is constituted by:
(1) an oxygen sensing element shaped like a shaft;
(2) a cylindrical casing for housing the oxygen sensing element;
(3) a ceramic separator being placed coaxially with the casing, supported directly or indirectly via a member in a casing support part formed at the rear end of the casing, and formed with a plurality of lead insertion holes axially penetrating the ceramic separator for inserting leads from the oxygen sensing element;
(4) a cover member being placed coaxially with the casing and coupled to the casing from the rear with the ceramic separator covered from the outside while allowing the leads to extend to the rear outside of the cover member; and
(5) a metal elastic member being placed at least between the cover member and the ceramic separator or between the casing support part and the ceramic separator in a compression state for producing a sandwich retaining force for the ceramic separator between the cover member and the casing support part.

In the structure of the oxygen sensor, the metal elastic member produces a proper sandwich holding force on the ceramic separator between the cover member and the casing for preventing a rattle and fixing and holding the ceramic separator more reliably. On the other hand, the metal elastic member also suppresses an excessive sandwich force acting on the separator support part of the ceramic separator because of elastic deformation of the metal elastic member when the oxygen sensor is assembled, etc., and in turn prevents the ceramic separator from being broken or chipped accordingly. The metal elastic member, which is made of metal, is excellent in heat resistance and can well maintain the ceramic separator rattle prevention effect over a long term even in a hostile operating environment at high temperature.

The ceramic separator can be formed with a separator support part projecting from the outer peripheral surface of the ceramic separator. The separator support part can be shaped like a flange along the circumferential direction of the ceramic separator, for example. The metal elastic member can be a spring washer being inserted into the ceramic separator and placed at least between the cover member and the separator support part or between the casing support part and the separator support part in a compression state. Such a spring washer is adopted as the metal elastic member, whereby it can be fitted into the ceramic separator extremely easily and an sufficient elastic force can be provided. Specifically, a wave washer, namely, a washer formed with axial wave-shaped swell in the ring circumferential direction can be used as the spring washer, whereby a comparatively uniform sandwich force around the axis can be produced for the ceramic separator and the ceramic separator can be supported more stably.

Next, the separator support part can be formed at an axial intermediate position of the ceramic separator. In this case, the ceramic separator can be placed with an axial front portion housed in the rear end of the casing, the separator support part abutting directly or indirectly via a member an opening end face part of the casing as the casing support part, and a rear portion projecting to the outside of the casing. The cover member covers the projection of the ceramic separator from the outside and can be formed at an axial intermediate position on the inner peripheral surface with a cover support part abutting directly or indirectly via a member the separator support part from the opposite side to the opening end face part of the casing. The spring washer can be placed between at least one of the cover support part and the end face of the casing and the separator support part. In the structure of the oxygen sensor, the separator support part is formed at an axial intermediate position of the ceramic separator, the front portion of the ceramic separator ahead the separator support part is housed in the casing, and the rear portion is housed in the cover member, whereby the ceramic sensor can be held more stably.

The cover member can have the axial front relative to a stepped part formed in an axial intermediate part of the cover member as a first portion and the rear as a second portion so that the second portion is made smaller in diameter than the first portion. The stepped part can be used as the cover support part and the spring washer can be placed between the cover support part and the separator support part. That is, to efficiently assemble the oxygen sensor of the structure, with the cylindrical casing upright, the ceramic separator is inserted through the upper opening and further the cover member is put from the upper side. In this case, if the spring washer is placed as described above, it can be easily and reliably fitted into the ceramic separator inserted into the casing and the oxygen sensor can be assembled more efficiently. The cover member is formed with the stepped part as described above, so that the spring washer can be sandwiched reliably between the stepped part and the separator support part.

In the structure of the oxygen sensor, the cover member of the oxygen sensor can be the filter assembly (in aspect (A) of the invention) being placed almost coaxially with the casing as a cylindrical body separate from the casing and coupled to the casing from the rear by the coupling part while allowing leads from the oxygen sensing element to extend to the rear outside of the filter assembly.

Aspect (G) of Invention

An oxygen sensor of the invention is constituted by an oxygen sensing element shaped like a shaft, a cylindrical casing for housing the oxygen sensing element, and a ceramic separator being placed coaxially with the casing, abutting a casing support part formed at the rear end of the casing and supported on the casing support part, and being formed with a plurality of lead insertion holes axially penetrating the ceramic separator for inserting leads from the oxygen sensing element. The casing support part is a buffer support part elastically deformed more easily than the main part of the casing in the axial direction of the casing and separator fixing means is provided for fixing the ceramic separator to the casing with the buffer support part compressed and deformed in the press direction by relatively pressing the ceramic separator against the buffer support part in the axial direction.

In the structure of the oxygen sensor, the buffer support part produces a proper sandwich holding force on the ceramic separator between the separator fixing means and the casing for preventing a rattle and fixing and holding the ceramic separator more reliably. On the other hand, it also suppresses an excessive sandwich force acting on the separator support part of the ceramic separator because of elastic deformation of the buffer support part when the oxygen sensor is assembled, etc., and in turn prevents the ceramic separator from being broken or chipped accordingly. Since the buffer support part is integrated with the casing as the casing support part, the need for disposing a rubber ring, etc., as another member as with the conventional oxygen sensor is eliminated. Resultantly, the number of parts is decreased for simplifying the sensor assembling step and in turn the sensor manufacturing efficiency can be improved.

In the structure of the oxygen sensor, the casing can be made of metal and the buffer support part can be made of the same metal material as the casing or different metal material from the casing. Thus, the buffer support part, which is made of metal, is excellent in heat resistance and can well maintain the ceramic separator rattle prevention effect over a long term even in a hostile operating environment at high temperature.

Specifically, the buffer support part can be a spring part integrated with the main part. The spring part is integrated with the main part, whereby the buffer support part can be elastically deformed reliably and in turn a necessary sufficient sandwich holding force on the ceramic separator can be produced between the separator fixing means and the casing for fixing the ceramic separator more reliably.

In this case, the spring part can be formed by bending back the opening end margin of the casing once or more than once in the radial direction of cross section. According to this method, the spring part can be formed easily in the opening end margin of the casing by press working, etc. More specifically, the spring part 90 can be formed by forming a thin part in the opening end margin of the casing, once bending back the thin part to the inside in the radial direction of cross section, and furthermore once bending back the tip of the bent-back thin part outwardly. As the thin part is formed, bend working for forming the spring part is more facilitated and moreover the spring part can be formed more easily by twice performing bend working.

The buffer support part may be formed so as to become a portion of lower hardness than the main part of the casing. That is, the hardness of the buffer support part is made lower than that of the main part, whereby the buffer support part can be compressed and deformed relatively to the main part to provide a similar function to the spring part. The buffer support part can be formed of a different material having lower hardness than the main part, for example. In this case, the different material portion can be joined to the main part by welding, brazing, etc. A formation method by applying local softening heat treatment to the portion of the casing to form the buffer support part by energization heating, etc., is also available. In this case, on the other hand, for example, the buffer support part and the main part are formed in one piece with the same material.

Assuming that the Vickers hardness of the buffer support part is Hvs and that the Vickers hardness of the main part is Hvh, it is advisable to set Hvh is 320 or more. If Hvh becomes less than 320, the strength of the casing is insufficient and durability of the oxygen sensor may be unable to be provided. More preferably, Hvh is set to 360 or more. It is advisable to adjust the hardness of the buffer support part so that Hvh−Hvs becomes 60 or more. If Hvh−Hvs becomes less than 60, a relative deformation amount of the buffer support part to the main part is insufficient and an intended effect may be unable to be sufficiently accomplished. More preferably, Hvh−Hvs is set to 80 or more.

The ceramic separator can be formed with a separator support part projecting from the outer peripheral surface of the ceramic separator. The separator support part can be shaped like a flange along the circumferential direction of the ceramic separator, for example. The buffer support part as a casing support part can be formed in the opening end face part of the casing and the separator support part can be abutted against the buffer support part, whereby the ceramic separator can be fitted extremely easily by simply inserting the ceramic separator into the casing through the opening thereof.

In the structure of the oxygen sensor, a cover member being placed coaxially with the casing and coupled to the casing from the rear with the ceramic separator covered from the outside while allowing the leads to extend to the rear outside of the cover member can be provided. In this case, the cover member can be formed at an axial intermediate position on the inner peripheral surface with a cover support part abutting the separator support part from the opposite side to the buffer support part. Thus, it is coupled to the casing with the buffer support part compressed and deformed, thereby forming the separator fixing means. The cover member can be provided for holding and fixing the ceramic separator more stably and reliably.

The cover member of the oxygen sensor can be the filter assembly (in aspect (A) of the invention) being placed almost coaxially with the casing as a cylindrical body separate from the casing and coupled to the casing from the rear while allowing leads from the oxygen sensing element to extend to the rear outside of the filter assembly.

Aspect (H) of Invention

An oxygen sensor of the invention is constituted by an oxygen sensing element shaped like a shaft, a cylindrical casing for housing the oxygen sensing element, a ceramic separator being placed in the casing and formed with a plurality of lead insertion holes axially penetrating the ceramic separator for inserting leads from the oxygen sensing element, and an elastic seal member being coaxially integrated with a rear opening or the rear of the casing and having an inside fitted elastically into the inside of a different cylindrical body communicating with the casing and seal lead insertion holes for inserting the leads for sealing a gap between outer faces of the leads and the inner face of the casing or the different cylindrical body. The axial rear end face of the ceramic separator adheres closely to the axial front end face of the elastic seal member. The ceramic separator is formed with a ventilation communication part axially penetrating the ceramic separator. An opening of the ventilation communication part on the side near to the elastic seal member in the axial direction is made at a position where the opening is not shielded by the elastic seal member.

In the structure of the oxygen sensor, the opening of the ventilation communication part on the side near to the elastic seal member is not shielded by the elastic seal member, thus ventilation of the ceramic separator in the ventilation communication part is not blocked although the elastic seal member is brought into intimate contact with the ceramic separator.

Specifically, the ceramic separator can be formed with a through hole for axial ventilation in addition to the separator lead insertion holes and can be formed on the rear end face with a ventilation groove communicating with the through hole for ventilation at one end and opened to the outer peripheral surface of the ceramic separator at the opposite end. In this case, the through hole for ventilation and the ventilation groove make up the ventilation communication part. According to the structure of the oxygen sensor, the opening at the opposite end of the ventilation groove is opened to the outer peripheral surface of the ceramic separator, thus not shielded by the elastic seal member and gas ventilation in the ventilation groove and its following through hole for ventilation can be made reliable. A lateral through hole opened at one end to the outer peripheral surface of the ceramic separator and at the opposite end communicating with the through hole for ventilation may be made in a direction crossing the axial direction in an axial intermediate part of the ceramic separator. However, to manufacture the ceramic separator by molding and calcining powder, if the ventilation groove is formed on the end face of the ceramic separator, a powder molded article can be manufactured by far easily and the manufacturing efficiency is high.

The oxygen sensor can be configured more specifically as follows: A gas introduction structure which has a filter holding part making a cylindrical form almost coaxial with the casing on the rear of the casing, having an inside communicating with the inside of the casing, and being formed in a wall with one or more gas introduction holes and a filter being placed so as to block the gas introduction hole or holes of the filter holding part for rejecting permeation of liquid and allowing gas to pass through is provided for introducing outside air into the casing through the filter and the gas introduction hole or holes (corresponding to the above-mentioned different cylindrical body). A ceramic separator is placed so that the rear thereof enters the inside of the filter holding part in the axial direction of the oxygen sensing element and the front enters the inside of the casing and is formed with a plurality of lead insertion holes axially penetrating the ceramic separator for inserting leads from the oxygen sensing element. An elastic seal member is fitted elastically into a rear opening of the filter holding part and having seal lead insertion holes for inserting the leads for sealing the gap between the outer faces of the leads and the inner face of the filter holding part. The rear end face of the ceramic separator is positioned on the rear side behind the gas introduction hole in the axial direction and adheres closely to the axial front end face of the elastic seal member. On the other hand, a gap is formed between the inner peripheral surface of the filter holding part and the outer peripheral surface of the ceramic separator at least at the lead insertion position and gas through the gas introduction hole is supplied to the gap. The ceramic separator is formed with the ventilation communication part for guiding the gas introduced into the gap into the casing.

According to the structure of the oxygen sensor, the filter for rejecting permeation of liquid and allowing gas to pass through is used to form a part of the gas introduction structure, so that water drops, etc., are prevented from entering the casing and outside air as a reference gas can be sufficiently introduced into the casing. In this case, the rear end face position of the ceramic separator is set behind the gas introduction hole. If water drops, etc., enter the gas introduction structure through the gas introduction hole, the ceramic sensor blocks the way of the water drops. Thus, the water drops, etc., become harder to flow into the casing. On the other hand, the reference gas flowing in through the gas introduction hole can be introduced into the casing through the ventilation groove and the through hole for ventilation without a hitch.

Next, the oxygen sensing element can be formed like a hollow shaft with the tip closed and a shaft-like heating element for heating the oxygen sensing element can be placed in the hollow part. In this case, the ceramic separator can have the four separator lead insertion holes for inserting the leads from the oxygen sensing element and the heating element so that centers of the lead insertion holes are positioned on a phantom circumferential path (separator pitch circle). The through hole for ventilation can be made in an area surrounded by the four separator lead insertion holes at the center of the ceramic separator. Further, the ventilation groove can be shaped like a cross at a position not interfering with the four separator lead insertion holes on the rear end face of the ceramic separator. Thus, efficient use of the limited volume of the ceramic sensor can be made to efficiently place and form the insertion holes of the leads from the oxygen sensing element and the heating element, the through hole for ventilation, and the ventilation groove in optimum sizes.

On the other hand, the oxygen sensor of the invention can be configured as follows: The ceramic separator is formed with a separator support part like a flange projecting from the outer peripheral surface of the ceramic separator at an intermediate position in the axial direction thereof, is placed so as to abut directly or indirectly via a member the rear end face of the casing in the separator support part in a state in which a portion positioned axially ahead the separator support part is entered in the rear end inside of the casing, and is placed in a state in which an axial rear portion is projected to the outside of the casing. The projection of the ceramic separator from the casing is covered with a cover member as the different cylindrical body from the outside. One or a plurality of the ventilation communication parts are formed so as to axially penetrate the flange part of the ceramic separator. Since the flange part can be used to provide the gas ventilation passage, the structure of the oxygen sensor is useful, for example, if the main part of the ceramic separator does not have a space for forming the ventilation communication part. If one ventilation communication part is made in the main part of the ceramic separator and another ventilation communication part is also made in the flange part, gas can be ventilated more smoothly.

Specifically, the ventilation communication part can be a plurality of grooves or notches made at predetermined angle intervals in the outer peripheral surface of the flange part, whereby gas can be ventilated uniformly in the circumferential direction of the flange part and moreover a powder molded article before it is calcined can also be formed easily and the manufacturing efficiency is high.:

In the structure of the oxygen sensor, the cover member of the oxygen sensor can be the filter assembly (in aspect (A) of the invention) being placed almost coaxially with the casing as a cylindrical body separate from the casing and coupled to the casing from the rear while allowing leads from the oxygen sensing element to extend to the rear outside of the filter assembly.

Aspect (I) of Invention

An oxygen sensor of the invention constituted by an oxygen sensing element shaped like a hollow shaft with the tip closed having electrode layers on inner and outer faces and a shaft-like heating element being placed in the hollow part of the oxygen sensing element for heating the oxygen sensing element, characterized in that the center axis of the heating element is offset to one side with respect to the center axis of the hollow part of the oxygen sensing element in the proximity of the heating part of the heating element. It is desirable that the surface of the heating part of the heating element is in contact with the hollow part inner wall of the oxygen sensing element as a result of such offset.

If the center axis of the heating element is offset to one side with respect to the center axis of the hollow part of the oxygen sensing element as described above, it is considered that the oxygen sensing element is locally heated on the offset side and the heating state around the center axis of the oxygen sensing element becomes uneven. In comparison with common knowledge, the structure in which the oxygen sensing element is heated unevenly involves a large number of disadvantages such that it is feared that it will take time until the electric resistance value of the oxygen sensing element becomes sufficiently low as a whole, resulting in the prolonged sensor start-up time. However, the inventor et al. found out that unexpectedly the sensor activation time is equal to the former sensor activation time or is shortened by adopting the seemingly undesirable structure.

For example, if the lateral strike structure in which the heating part comes in contact with the oxygen sensing element is adopted, heat generated in the heating part of the heating element can be conducted from the heating part directly to the oxygen sensing element based on the contact and radiation heat in the proximity of the contact point can also act effectively on the oxygen sensing element, thereby raising the temperature of the oxygen sensing element in a short time for shortening the sensor activation time. If a structure in which the heating part of the heating element is in contact with the hollow part inner wall of the oxygen sensing element from side is adopted, even if thermal expansion of the heating part or the oxygen sensing element occurs, the structure is hard to receive the effect of the thermal expansion as compared with a structure wherein the tip of the heating part is stricken against the inner face of the tip of the oxygen sensing element. In other words, if the heating part or the oxygen sensing element receives a heat history, the contact state therebetween becomes easy to maintain good by adopting the lateral strike structure.

If the heating part is stricken against the hollow part inner wall of the oxygen sensing element from side, the heat conduction efficiency as a whole becomes higher than that in the structure wherein the tip of the heating part is stricken against the tip of the oxygen sensing element because of the effects of direct heat conduction caused by the contact and the radiation heat. The contact state between the oxygen sensing element and the heating part of the heating element in the oxygen sensor can be stably made reliable as described above, so that variations in the oxygen sensing element heating state are decreased, leading to the effect of decreasing variations in the characteristics of the oxygen sensor.

The oxygen sensor is constituted by a cylindrical casing for housing the oxygen sensing element and a ceramic separator being placed almost coaxially with the rear end of the oxygen sensing element and formed with a plurality of lead insertion holes axially penetrating the ceramic separator for inserting leads from the oxygen sensing element and the heating element. The lead insertion holes are arranged so as to surround the center axis of the ceramic separator. The ceramic separator is formed with a heating element end housing hole opened at one end in the front end face of the ceramic separator with the bottom positioned in an axial intermediate part of the ceramic separator and an inner diameter set larger than the outer diameter of the heating element. The heating element end housing hole is formed by cutting away the center of the ceramic separator so as to overlap the separator lead insertion holes from the inside and the rear end part of the heating element is housed in the heating element end housing hole.

If the heating element is offset as described above, the rear end part thereof is offset with respect to the axis of the ceramic separator. Since the heating element end housing hole for housing the rear end part of the heating element has the inner diameter set larger than the outer diameter of the heating element, a diametrical move of the rear end part accompanying with the offset of the heating element is allowed within a given limit. That is, if the heating element is offset, the rear end part thereof is prevented from interfering with the inner wall of the ceramic separator and the offset amount can be set comparatively flexibly.

If the lead insertion holes are made so that the centers thereof are placed on a phantom circumferential circle (pitch circle), it is advisable to set the inner diameter $d1$ of the heating element end housing hole smaller than the diameter $d2$ of the separator pitch circle (namely, $d1<d2$). That is, the portion of the ceramic separator positioned between the adjacent separator lead insertion holes functions as a partition wall for separating the leads; as the heating element end housing hole is made, the partition wall is cut away from the inside. If $d1 \geq d2$, the diametrical length of the partition wall becomes too short and the separation effect of the leads may be degraded, leading to a short circuit, etc.

It is desirable that the ratio between the diameter $d2$ of the pitch circle C1 of the lead insertion holes and the outer diameter D of the end of the heating element, $d2/D$, is adjusted in the range of 1.7 to 2.8. If $d2/D$ becomes less than 1.7, a sufficient offset amount of the heating element cannot be provided, resulting in an insufficient lateral strike state of the heating element; a sufficient effect of shortening the sensor start-up time may be unable to be expected. If $d2/D$ exceeds 2.8, the leads are too bent and damage, etc., to the leads easily occurs. On the other hand, it is advisable to set the ratio between depth h and inner diameter $d1$ of the heating element end housing hole, $h/d1$, to 1.2 or less. For example, to incline the heating element to offset it, if $h/d1$ exceeds 1.2, the depth h of the housing hole becomes too large relative to the diameter $d1$ and a sufficient inclination amount of the heating element, namely, a sufficient offset amount cannot be provided; a sufficient effect of shortening the sensor start-up time may be unable to be expected.

The oxygen sensing element can be formed on the inside and the hollow part inner wall with porous electrodes, such as Pt porous electrodes, each having a reversible catalyst function (oxygen dissociation function) for an oxygen molecule dissociation reaction to pour oxygen into the solid electrolyte forming the oxygen sensing element and an oxygen rebonding reaction to cause oxygen to be released from the solid electrolyte. In this case, if the oxygen sensing element is heated locally, the sensor start-up time is maintained to a similar degree to the former sensor start-up time or is shortened. The following is possible as the factor:

With the oxygen sensor, for example, a reference gas of air, etc., is introduced into the oxygen sensing element and the gas to be measured, such as exhaust gas, is brought into contact with the outside of the oxygen sensing element, then the oxygen concentration in the measured gas is detected according to the oxygen concentration cell electromotive force produced at the oxygen sensing element based on the oxygen concentration difference between the inside and outside of the oxygen sensing element. In this case, for a sufficient oxygen concentration cell electromotive force to occur in the oxygen sensing element formed of an oxygen ion conductive solid electrolyte, it is necessary to sufficiently raise catalyst activity of the porous electrodes to an oxygen molecule dissociation or rebonding reaction as well as to sufficiently lessen the electric resistance value of the oxygen sensing element. The detection output level of the sensor is determined by tradeoffs of the electric resistance value of the oxygen sensing element and the catalyst activity of the porous electrodes.

It is estimated that the catalyst activity of the porous electrode made of Pt, etc., for example, tends to grow rapidly in response to temperature rather than the oxygen ion mobility of a solid electrolyte of $ZrO_2$ family, etc. When the oxygen sensing element is heated locally in the structure of the invention, a decrease in electric resistance of the oxygen sensing element as the solid electrolyte is activated develops less than that in the former structure in which the oxygen sensing element and the heating element are placed concentrically because of uneven heating. However, the locally heated portion is heated to higher temperature as compared with the former structure, thus the catalyst activity of the porous electrodes is raised in the portion and dissociation of oxygen molecules in the measured gas is promoted. Then, the effect compensates for the concentration cell electromotive force of the solid electrolyte and in turn the detection output level of the sensor, resulting in the effect of making the sensor activation time equal to the former sensor activation time or shortening the sensor activation time.

Next, if the heating part of the heating element has a heating sparse portion of a sparse heating distribution in a part of the outer peripheral surface in the circumferential direction thereof, it can be brought into contact with the hollow part inner wall of the oxygen sensing element in a portion other than the heating sparse portion. For example, to print a heating resistance pattern on a ceramic green sheet, wind it around a core, and calcine it, thereby forming the heating part, a heating pattern becomes sparse on the joint side. Thus, for example, the heating part surface on the opposite side can be brought into contact with the hollow part inner wall of the oxygen sensing element. This means that it is more effective to bring the sufficient heating portion although a given heat transmission effect is also produced if the heating sparse portion comes in contact with the hollow part inner wall. The heating part of the heating element is offset in the circumferential direction, so that heating energy concentrates on a smaller volume and particularly the effect of shortening the activation time after the heater energization time is produced.

The fact that the heating part of the heating element is unevenly distributed in the tip of the heating element is effective on prompt heating of the oxygen sensing element. That is, the heating part can also be spread on the whole of the heating element, but in doing so, heat energy is easily dispersed. To effectively heat the oxygen sensing element, if the heating part is unevenly distributed in the tip of the heating element, it generates heat locally; it is preferred. The sensor activation time can be more shortened by using the local heating pattern of the heating part and the lateral strike structure based on offset placement in combination.

Further, a structure can be adopted wherein the heating element is fitted into the oxygen sensing element via a terminal metal shell for pressing the heating part of the heating element against the hollow part inner wall of the oxygen sensing element, whereby the lateral strike structure as described above is guaranteed more stably and the effect of decreasing variations in the sensor characteristics is enhanced furthermore.

A preferred example of the terminal metal shell can be constituted by a heating element grip part for gripping a heating element, at least one internal electrode connection part being formed so as to surround the heating element in the circumferential direction and coming in contact with an inner electrode layer of an oxygen sensing element, and a guide part for pressing the heating element in a direction perpendicular to the axial direction of the heating element on the opposite side to the heating element grip part with the internal electrode connection part between. The center axis of the heating element is inclined relative to the center axis of the hollow part of the oxygen sensing element by the heating element grip part and the guide part, whereby the heating part of the heating element is pressed against the hollow part inner wall, also called the element inner wall, and the heating element is fixed. According to the structure, the guide part presses the heating element against the element inner wall, thus the lateral strike structure described above can be realized easily through the terminal metal shell.

Focusing attention on stress produced on the heating element, a resultant bend moment acting on the heating element, of stress acting on the heating element in the element inner wall, stress acting on the heating element in the guide part, and stress acting on the heating element in the heating element grip part occurs in the heating element. It is advisable to lessen the elastic force of the guide part so that the heating element is not broken by the bend moment. In other words, the heating element is pressed against the element inner wall mainly by the elastic force of the guide part and the elastic force is adjusted properly, whereby the press state of aggressive contact form of the heating element can be continued stably while break, etc., of the heating element is prevented.

A coupling part for coupling at least the guide part and the internal electrode connection part or the internal electrode connection part and the heating element grip part in a narrow form can be formed as a specific example for lessening the elastic force of the guide part. As a result of the presence of the coupling part in a narrow form, the elastic force of the guide part is properly lessened and break, etc., of the heating element can be prevented effectively. When the heating element is about to become deformed due to thermal stress, it can also be expected that the coupling part becomes elastically deformed (or plastically deformed) properly for easing the deformation of the heating element.

Next, the terminal metal shell can also be a terminal metal shell which is constituted by at least one internal electrode connection part being formed so as to surround a heating element in the circumferential direction and coming in contact with an inner electrode layer of an oxygen sensing element, a first heating element grip part being adjacent to one side of the internal electrode connection part and integrated therewith and formed so as to surround the heating element in the circumferential direction for gripping the heating element, and a second heating element grip part being adjacent to the opposite side of the internal electrode connection part and integrated therewith with the center axis offset from the center axis of the first heating element grip part and formed so as to surround the heating element in the circumferential direction for gripping the heating element. In this case, the center axis of the heating element is inclined relative to the center axis of the hollow part of the oxygen sensing element by the first and second heating element grip parts with the center axes offset from each other, whereby the heating part of the heating element is pressed against the hollow part inner wall and the heating element is fixed. According to the structure, the heating element is held in the inclination state and pressed against the element inner wall by the two grip parts offset from each other, thus the lateral strike structure described above can be realized easily through the terminal metal shell. The heating element can be held in the inclination state more stably by the two grip parts and the lateral strike effect of the heating part can be accomplished more reliably.

More specifically, the first and second heating element grip parts can be connected to the periphery on the same side in the diametric direction of the heating element to the corresponding ends of the internal electrode connection part and the center axis of the first heating element grip part can be positioned on a far side from the center axis of the second heating element grip part viewed from the connection part. In the structure, when the heating part is formed at the tip of the heating element, the tip of the heating element is inclined to the connection part side and is pressed against the element inner wall on the connection part side. For example, when an output (or ground) terminal of the oxygen sensing element is projected at a position corresponding to the connection part side to the first heating element grip part at the end opposed to the connection side to the internal electrode connection part, the heating element is placed as described above, whereby, for example, interference between a power supply terminal of the heating element (generally, formed at the end of the heating element opposed to the heating part formation side) and the output terminal becomes hard to occur when the oxygen sensor is assembled, and in turn the sensor can be assembled easily. However, if a problem of the interference between the terminals, etc., does not occur, the center axis of the first heating element grip part may be positioned on a near side to the connection part from the center axis of the second heating element grip part (namely, inclination of the heating element is inverted).

More specifically, the first heating element grip part and the internal electrode connection part can be placed so that their center axes almost match, and the second heating element grip part can be placed so that its center axis is offset to the connection part side with respect to the center axis of the internal electrode connection part. That is, the first heating element grip part and the internal electrode connection part are placed coaxially, whereby, for example, the power supply terminal of the heating element and the output (or ground) terminal of the oxygen sensing element can be spaced from each other comparatively uniformly, and in turn trouble such as insulation failure between the terminals can be decreased.

Also in the structure, the terminal metal shell can be formed with a coupling par for coupling the first heating element grip part and the internal electrode connection part or the internal electrode connection part and the second heating element grip part in a narrow form. That is, if the heating element is gripped at the two grip parts, heat expansion or shrinkage of the heating element is easily restricted and thermal stress easily occurs, but the coupling part becomes elastically or plastically deformed for easing the thermal stress and in turn making damage to the heating element, etc., hard to occur.

In this case, the coupling part formed between the first heating element grip part and the internal electrode connection part (first coupling part) and the coupling part formed between the internal electrode connection part and the second heating element grip part (second coupling part) each can be bent inward in the diametric direction of the internal electrode connection part to form a stepped part. In doing so, a new advantage is produced that the offset amount between the center axes of the first and second heating element grip parts can be easily adjusted by adjusting the bend amounts of the first and second coupling parts.

At least either of the internal electrode connection part and the heating element grip part of the terminal metal shell can also be formed with a positioning projection part projecting from the inner face of the internal electrode connection part or the heating element grip part and abutting the outer peripheral surface of the heating element for positioning the heating element so that the center axis of the heating element is offset to one side relative to the center axis of the hollow part of the oxygen sensing element in the proximity of the heating part. The positioning projection part can be easily formed by press working, etc., for example, if the terminal metal shell is made of a drawn article. The offset amount of the center axis of the heating element from the center axis of the hollow part can also be adjusted easily in response to the projection height of the positioning projection part from the internal electrode connection part or the inner face of the heating element grip part.

Both or either of the heating element grip part and the internal electrode connection part may be formed with the positioning projection part in the terminal metal shell. However, if the internal electrode connection part is formed with the positioning projection part and either of the heating element grip parts coupled to the internal electrode connection part is omitted, the length of the terminal metal shell in the axial direction of the heating element can be shortened and in turn the oxygen sensor can be shortened in the axial length and can be made compact. Since the heating element is gripped by one grip part, for example, when the heating element with the terminal metal shell attached is inserted into the hollow part of the oxygen sensing element for assembling the oxygen sensor, an excessive lateral force via the terminal metal shell becomes hard to act on the heating element and damage, etc., to the heating element at the assembling time can be prevented.

The heating element grip part to be omitted in the terminal metal shell may be on either side in the length direction of the heating element. However, if the heating element grip part on the far side from the heating element is omitted, in other words, if the heating element grip part is coupled only to the side of the internal electrode connection part near to the heating part of the heating element in the terminal metal shell, gripping of the heating element on the far side easily affected by an external force through the output terminal, etc., of the oxygen sensor is released and if a lateral force is received, it is easily relaxed; the effect of preventing damage, etc., to the heating element can be enhanced furthermore. More specifically, the internal electrode connection part is formed with the positioning projection part at a position corresponding to the coupling part of the heating element grip part to the internal electrode connection part in the proximity of the end on the opposed side to the side where the heating element grip part is coupled, the distance between the support point of the positioning projection part (abutment point) and the support point of the heating element grip part can be increased in the axial direction of the heating element and in turn the heating element can be positioned and supported more stably by means of the terminal metal shell.

If a first phantom plane containing the center axis of the hollow part of the oxygen sensing element and a second phantom plane containing the center axis of the hollow part and being orthogonal to the first plane are set in the hollow part and the hollow part is divided by the first plane and the second plane into four areas, the heating element can be placed so that the whole of the portion of the center axis positioned in the hollow part fits in any of the four areas. In other words, the first and second phantom planes can always set anywhere so that the whole of the portion of the center axis of the heating element positioned in the hollow part fits in any of the four areas of the hollow part.

The advantages provided by the structure of the oxygen sensor will be discussed with reference to FIG. 30. For convenience in the description to follow, it is assumed that the heating part 42 is formed in the insertion end of the heating element 3 into the oxygen sensing element 2 and that the hollow part inner wall 2a of the oxygen sensing element 2 forms almost a cylindrical face (however, the hollow part inner wall 2a may be given a taper with the bottom shrunk in diameter for the purpose of enhancing the releasability at the molding time, etc., when it is manufactured by molding and calcining solid electrolyte powder). First, FIG. 30c shows a case in which if the first and second phantom planes P1 and P2 are set anyway, the center axis O1 of the heating element 3 cannot be fitted in any one of the four areas of the hollow part separated by the planes P1 and P2. That is, the center axis O1 is fairly inclined to the center axis O2 of the oxygen sensing element 2 and resultantly the center axis O1 must inevitably be spread across two or more areas of the follow part. On the other hand, FIG. 30b shows a case in which if the first and second phantom planes P1 and P2 are set properly, the center axis O1 of the heating element 3 can be fitted in any one of the four areas. In this case, inclination of the center axis O1 of the heating element 3 to the center axis O2 of the oxygen sensing element 2 becomes always gentle as compared with the case shown in FIG. 30c.

In comparison therebetween, in the structure shown in FIG. 30c, the distance to the hollow part inner wall 2a of the oxygen sensing element 2 becomes short at the corner of the end side of the heating element 2 and heating tends to concentrate slightly on the portion. In contrast, in the structure shown in FIG. 30a, the inclination of the center axis O1 of the heating element 3 to the center axis O2 of the oxygen sensing element 2 is more gentle than that in the structure in FIG. 30c, thus the side of the heating part 42 becomes almost parallel to the hollow part inner wall 2a of the oxygen sensing element 2 and the walls of the oxygen sensing element 2 can be heated more uniformly by the heating part 42. Resultantly, a larger effect of shortening the oxygen sensor activation time can be expected. However, also in the structure shown in FIG. 30c, the center axis O1 of the heating element 3 is offset from the center axis O2 of the oxygen sensing element 2 and a given or more effect of shortening the oxygen sensor activation time can be expected, needless to say.

In this case, as shown in FIG. 30b, if the heating element 3 is placed in the hollow part so that the center axis of the heating element 3 becomes almost parallel to the center axis of the hollow part of the oxygen sensing element, the effect of making the side of the heating part 42 parallel to the hollow part inner wall 2a of the oxygen sensing element 2 and in turn the effect of uniformly heating the walls of the oxygen sensing element 2 can be accomplished more noticeably.

Specifically, the heating element 3 can be placed in offset relation so that the center axis of the heating element becomes almost parallel to and one-sided to the center axis of the hollow part of the oxygen sensing element. In this case, a terminal metal shell having an internal electrode connection part being formed so as to surround the heating element in the circumferential direction and coming in contact with the inner electrode layer of the oxygen sensing element and a pair of heating element grip parts being coupled to both sides of the internal electrode connection part in the axial direction of the heating element for gripping the heating element can be provided. According to the structure of the oxygen sensor, a new advantage of providing a capability of holding the heating element more stably by the two grip parts is added.

On the other hand, a terminal metal shell having an internal electrode connection part being formed so as to surround the heating element in the circumferential direction and coming in contact with the inner electrode layer of the oxygen sensing element and a heating element grip part being coupled only to the end part of the internal electrode connection part near to the tip of the heating element in the axial direction thereof for gripping the heating element can also be provided. According to the structure of the oxygen sensor, the heating element is gripped by one grip part with some motion freedom in the direction crossing the axis. Therefore, if the heating element is inserted into the hollow part of the oxygen sensing element together with the terminal metal shell, as the tip of the heating element comes in contact with the inner wall of the oxygen sensing element, the heating element is positioned in parallel with the inner wall accordingly and a larger effect of shortening the oxygen sensor activation time can be expected. When the oxygen sensor is assembled, an excessive lateral force via the terminal metal shell becomes hard to act on the heating element and in turn damage to the heating element, etc., at the assembling time can be prevented. Further, the length of the terminal metal shell in the axial direction of the heating element can be shortened and in turn the length of the oxygen sensor in the axial direction of the heating element can be shortened for making the oxygen sensor compact.

In the invention, the surface of the heating part of the heating element is out of contact with the hollow part inner wall of the oxygen sensing element and is positioned extremely near regardless of the offset placement of the heating element relative to the oxygen sensing element. Even in such a structure, the effect of heat radiation, etc., from the heating part to the oxygen sensing element is enhanced as compared with the case with no offset, thus a given effect of shortening the oxygen sensor activation time is produced.

In the oxygen sensor of the invention, it is desirable that the difference between the axis section inner size of the oxygen sensing element, DA, and the axis section outer size of the heating element, DB, $\Delta D=DA-DB$, is 0.35 mm or less. If the inner peripheral surface of the oxygen sensing element or the outer peripheral surface of the heating element is cylindrical, the axis section inner size of the oxygen sensing element means the inner diameter or the axis section outer size of the heating element means the outer diameter. If the inner peripheral surface of the oxygen sensing element or the outer peripheral surface of the heating element has an axis section form off a circle, the axis section size means the inner diameter or the outer diameter in terms of the circular cross section of the same area. Further, if the axis section size is not constant in the axial direction (for example, shaped like a taper), a mean value in the axial direction of the axis section size is adopted.

If $\Delta D=DA-DB$ exceeds 0.35 mm, the oxygen sensing element activation time and in turn the sensor start-up time may be prolonged or the sensor start-up time may easily vary from one sensor to another. The possible reason is as follows: For example, to strike the heating part against the hollow part inner wall of the oxygen sensing element from side, if $\Delta D$ grows, the lateral strike force easily varies from one sensor to another. More preferably, the value of $\Delta D$ is set to 0.30 mm or less. On the other hand, if $\Delta D$ becomes less than 0.1 mm, it becomes hard to insert the heating element into the hollow part of the oxygen sensing element and the efficiency of fitting the heating element into the oxygen sensing element may be lowered. Therefore, it is advisable to set $\Delta D$ to 0.1 mm or more; more preferably, $\Delta D$ is set to 0.15 mm or more.

It is desirable that the ratio of the difference between the axis section inner size of the oxygen sensing element, DA, and the axis section outer size of the heating element, DB, $\Delta D=DA-DB$, to DB, $\Delta D/DB$, is 0.13 or less. If $\Delta D/DB$ exceeds 0.13, the sensor start-up time may be prolonged or may easily vary from one sensor to another. More preferably, $\Delta D/DB$ is set to 0.10 or less.

The structure of the oxygen sensor is effective particularly if the heating element is gripped only by one grip part. That is, $\Delta D$ or $\Delta D/DB$ is adjusted in the above-mentioned range, whereby as the tip of the heating element comes in contact with the hollow part inner wall of the oxygen sensing element, it becomes more easily parallel to the hollow part inner wall of the oxygen sensing element and the effect of shortening the oxygen sensor activation time is enhanced furthermore.

Aspect (J) of Invention

An oxygen sensor of a first structure according to aspect (J) of the invention is constituted by an oxygen sensing element shaped like a hollow shaft with the tip closed having electrode layers on inner and outer faces, a shaft-like heating element being placed in the hollow part of the oxygen sensing element for heating the oxygen sensing element, and a terminal metal shell. The terminal metal shell is constituted by an internal electrode connection part being formed so as to surround a heating element in the circumferential direction and coming in contact with an inner electrode layer of an oxygen sensing element, a heating element grip part being coupled to at least one side of the internal electrode connection part in the axial direction of the heating element for gripping the heating element. The heating element grip part of the terminal metal shell is shaped like a cylinder into which the heating element is inserted, and becomes elastically deformed radially outward as the heating element is inserted for gripping the heating element by an elastic restoration force. It is also formed in at least one end margin in the axial direction with a heating element insertion guide part for guiding insertion of the heating element.

According to the structure of the oxygen sensor, the heating element grip part is formed with the heating element insertion guide part, thus when the heating element is inserted into the heating element grip part for fitting the terminal metal shell, the end margin of the heating element becomes hard to be caught in the margin of the heating element grip part, whereby the heating element can be easily fitted into the terminal metal shell and in turn the oxygen sensor manufacturing efficiency can be enhanced.

In the oxygen sensor, often the heating element is inserted into the heating element grip part from the tip for fitting the heating element into the heating element grip part. In this case, it is desirable that the heating element insertion guide part is formed in the margin of the heating element grip part on the far side from the tip of the oxygen sensing element.

Next, the heating element insertion guide part can be formed as a notch part cut from the end margin of the cylindrical heating element grip part in the axial direction thereof and reduced in width gradually in the depth direction, whereby the heating element can be inserted smoothly into the heating element grip part.

An oxygen sensor of a second structure according to aspect (J) of the invention is constituted by an oxygen sensing element shaped like a hollow shaft with the tip closed having electrode layers on inner and outer faces, a shaft-like heating element being placed in the hollow part of the oxygen sensing element for heating the oxygen sensing element, and a terminal metal shell. The terminal metal shell is constituted by an internal electrode connection part being formed so as to surround a heating element in the circumferential direction and coming in contact with an inner electrode layer of an oxygen sensing element, a heating element grip part being coupled to at least one side of the internal electrode connection part in the axial direction of the heating element for gripping the heating element. The heating element grip part of the terminal metal shell is shaped like a cylinder into which the heating element is inserted, and becomes elastically deformed radially outward as the heating element is inserted for gripping the heating element by an elastic restoration force. It is also formed in at least one end margin in the axial direction with a notch cut in the axial direction and reduced in width gradually in the depth direction.

According to the structure of the oxygen sensor, the notch made in the heating element grip part can function as a heating element insertion guide part for guiding insertion of the heating element, whereby when the heating element is inserted into the heating element grip part for fitting the terminal metal shell, the end margin of the heating element becomes hard to be caught in the margin of the heating element grip part, so that the heating element can be easily fitted into the terminal metal shell and in turn the oxygen sensor manufacturing efficiency can be enhanced.

In the first and second structures of the oxygen sensor, the cylindrical heating element grip part can be formed with a slit from one end margin to another end margin in the axial direction and the notch can be formed by cutting away both side portions of the slit of the heating element grip part. By forming the slit, the heating element grip part can be easily elastically deformed radially outward as the heating element is inserted. The notch can be formed like a taper by cutting away both side portions of the slit of the heating element grip part from an intermediate position of the slit to one margin.

The terminal metal shell having the heating element grip part can be easily manufactured by adopting the following structure: It is formed of a metal plate member with a first plate-like portion to become the internal electrode connection part and a second plate-like portion to become the heating element grip part, the first and second plate-like portions being adjacent to each other in the length direction and coupled to each other by a coupling part at intermediate positions in the width direction. The first plate-like portion is bent like a cylinder in both side portions in the width direction to form the internal electrode connection part. Likewise, the second plate-like portion is bent like a cylinder in both side portions in the width direction to form the heating element grip part. Then, both end margins in the width direction are opposed to each other to form the slit.

What is claimed is:

1. An oxygen sensor comprising:
   an oxygen sensing element with a shaft shape;
   a cylindrical casing for housing said oxygen sensing element;
   a gas introduction structure having a filter holding part marking a cylindrical form coaxial with said casing on a rear of said casing, having an inside communicating with said casing, and one or more gas introduction holes being formed in a wall and a filter being placed so as to block the gas introduction hole or holes of said filter holding part for rejecting permeation of liquid and allowing gas to pass through, said gas introduction structure for introducing outside air into said casing through the filter and the gas introduction hole or holes; and
   a protective cover being formed in the shape of a cylinder for covering said gas introduction structure from an outside thereof for blocking or suppressing a direct jet of liquid drops to said filter or deposition of oil or dirt on said filter, wherein said protective cover is joined to an outer face of the filter holding part by a cover joint part with a gas retention space produced between said protective cover and the filter at a position corresponding to the gas introduction hole; and
   wherein an external communication part for allowing the gas retention space to communicate with the outside and introducing outside air into the gas retention space is provided,
   wherein the cover joint part is formed annularly along a circumferential direction of said protective cover;
   wherein the external communication part is a passage crossing the annular cover joint part between said protective cover and the filter holding part,
   wherein a plurality of predetermined-length grooves as the external communication part extending in the axial direction of the filter holding part are formed with a predetermined spacing along the circumferential direction on the outer peripheral surface of the filter holding part ahead the gas introduction hole;
   the cover joint part is an annular crimp part formed so as to cross the grooves and leave a gap between said protective cover and the filter holding part at the bottom of each groove by crimping said protective cover toward the filter holding part; and
   outside air is introduced into the gas retention space through the grooves from a front opening of the gap formed between said protective cover and the filter holding part.

2. The oxygen sensor as claimed in claim 1 wherein said protective cover extends toward a front end of the oxygen sensor from an end of each groove.

3. The oxygen sensor as claimed in claim 1 wherein the filter holding part has an axial front relative to a stepped part formed in an axial intermediate part of the filter holding part as a first portion and a rear as a second portion so that the second portion is made smaller in diameter than the first portion, the gas introduction hole being made in a wall of the second portion; and
   the grooves are formed on an outer peripheral surface of the first portion and said protective cover is fixedly secured to the first portion by the annular crimp part in a front end part and is fixedly secured to an outer peripheral surface of an end part of the second portion by another crimp part.

4. The oxygen sensor as claimed in claim 1 further comprising a ceramic separator being formed with a plurality of lead insertion holes axially penetrating said ceramic separator for inserting leads from said oxygen sensing element, wherein
   said ceramic separator is formed with a separator support part having a flange shape projecting from an outer peripheral surface of said ceramic separator at an intermediate position in an axial direction thereof;

said ceramic separator is placed so as to abut directly or indirectly via a member a rear end face of said casing at the separator support part in a state in which a portion positioned ahead of the separator support part is located in a rear end of said casing; and an annular crimp part as the cover joint part is formed at a position corresponding to an outer peripheral surface of the separator support part.

5. An oxygen sensor comprising:

an oxygen sensing element with a shaft shape;

a cylindrical casing for housing said oxygen sensing element;

a gas introduction structure comprising a filter holding part making a cylindrical form substantially coaxial with said casing on a rear of said casing, having an inside communicating with an inside of said casing, and one or more gas introduction holes being formed in a wall, a filter being placed so as to block the gas introduction hole or holes on an outside of the filter holding part for rejecting permeation of liquid and allowing gas to pass through, and an auxiliary filter holding part having a wall with one or more auxiliary gas introduction holes with a cylinder shape placed on an outside of the filter for sandwiching the filter between the auxiliary filter holding part and the filter holding part, for introducing outside air into said casing through the auxiliary gas introduction hole, the filter, and the gas introduction hole; wherein the filter comes in intimate contact with an inner face of the auxiliary filter holding part at least in surroundings of the auxiliary gas introduction hole and a predetermined gap is formed between the outer face of the filter holding part and the filter at least in surroundings of the gas introduction hole;

wherein the auxiliary filter holding part includes a joint portion for joining to the filter holding part, the joint portion defining a plurality of predetermined-length grooves extending in the axial direction of the filter holding part for communication with the outside and introducing outside air into the casing.

6. The oxygen sensor as claimed in claim 5 wherein the auxiliary filter holding part is formed with filter crimp parts for coupling the auxiliary filter holding part to the filter holding part via the filter on two axial sides with the auxiliary gas introduction hole between; and a portion positioned between the filter crimp parts of the auxiliary filter holding part is bent outward together with the filter to form a convex form with a top part, the auxiliary gas introduction hole is made in the top of the convex part, the top of the convex part being flattened at least in surroundings of the auxiliary gas introduction hole, and the inner face of the auxiliary filter holding part adheres closely to the filter in the flattened part.

7. The oxygen sensor as claimed in claim 6 wherein in the portion sandwiched between the crimp parts, the auxiliary filter holding part is bent outward and the filter holding part is bent inward and the gap is formed between the filter holding part and the filter based on a bend amount difference between the auxiliary filter holding part and the filter holding part.

8. The oxygen sensor as claimed in claim 6 wherein a plurality of the gas introduction holes and a plurality of the auxiliary gas introduction holes are made with a predetermined spacing along a circumferential direction in positional relationship corresponding to each other in an axial intermediate part in the filter holding part and the auxiliary filter holding part;

the filter is placed so as to surround the filter holding part in the circumferential direction;

the auxiliary filter holding part is formed with the crimp parts annularly along the circumferential direction of the auxiliary filter holding part on both sides of a row of the auxiliary gas introduction holes, wherein the convex part is formed annularly between the crimp parts; and the top of the convex part is flattened annularly and the auxiliary gas introduction holes are made in the flattened part.

9. The oxygen sensor as claimed in claim 5 wherein the filter holding part is formed with a concave part dented inward at least in surroundings of the gas introduction hole and the gap is formed between the filter holding part and the filter in the concave part.

10. An oxygen sensor comprising:

an oxygen sensing element with a shaft shape;

a cylindrical casing for housing said oxygen sensing element;

a filter assembly being placed substantially coaxially with said casing as a cylindrical body separate from said casing and coupled to said casing from a rear while allowing leads from said oxygen sensing element to extend to the rear outside of said filter assembly;

a coupling part for coupling said filter assembly and said casing; and a rotation prevention part having a polygonal axis cross section for preventing said filter assembly and said casing from relatively rotating around the axis of said filter assembly and said casing, wherein said filter assembly comprises:

a filter holding part having a wall with one or more gas introduction holes making a cylindrical form substantially coaxially coupled to said casing from a rear of said casing, having an inside communicating with an inside of said casing;

a filter being placed so as to block the gas introduction hole or holes in the filter holding part from an inner or outer face side for rejecting permeation of liquid and allowing gas to pass through; and an auxiliary filter holding part for fixing the filter to the filter holding part, outside air introducing into said casing through the filter and the gas introduction hole;

wherein the auxiliary filter holding part includes a joint portion for joining to the filter holding part, the joint portion defining a plurality of predetermined-length grooves extending in the axial direction of the filter holding part for communication with the outside and introducing outside air into the casing.

11. The oxygen sensor as claimed in claim 10 wherein said casing and said filter assembly are formed as separate bodies and said filter assembly is placed on the rear of said casing, then said coupling part is formed, thereby coupling said casing and said filter assembly.

12. The oxygen sensor as claimed in claim 10 wherein said filter assembly comprises:

a filter holding part being placed coaxially and integrally with the rear of said casing so that an inside of the filter holding part communicates with an inside of said casing and one or more gas introduction holes being formed in a wall;

a filter being placed so as to block the gas introduction hole or holes on an outside of the filter holding part for rejecting permeation of liquid and allowing gas to pass through; and an auxiliary filter holding part having a wall with one or more auxiliary gas introduction holes and having a cylinder shape being placed on an outside of the filter for sandwiching the filter between the auxiliary filter holding part and the filter holding part, outside air introducing into said casing through the auxiliary gas introduction hole, the filter, and the gas introduction hole.

13. The oxygen sensor as claimed in claim 12 wherein a plurality of the gas introduction holes and a plurality of the auxiliary gas introduction holes are made with a predetermined spacing along a circumferential direction in positional relationship corresponding to each other in an axial intermediate part in the filter holding part and the auxiliary filter holding part;

the filter is placed so as to surround the filter holding part in the circumferential direction; and the auxiliary filter holding part is formed with an annular filter crimp part along the circumferential direction of the auxiliary filter holding part by crimping the auxiliary filter holding part toward the filter holding part with the filter between.

14. The oxygen sensor as claimed in claim 13 wherein the filter has a cylinder shape and is placed along the outer periphery of said casing;

the filter crimp part is formed along the circumferential direction on a rear end of the auxiliary filter holding part; and a filter check part to visually check the filter positioned between the auxiliary filter holding part and the filter holding part is formed on the rear end of the auxiliary filter holding part.

15. The oxygen sensor as claimed in claim 10 wherein the filter holding part is placed so as to overlap said casing at a tip of the filter holding part from an outside; and an annular assembly coupling crimp part as the coupling part is formed in a circumferential direction of the filter holding part and said casing by crimping the filter holding part toward said casing in the overlap and presses an inner peripheral surface of the filter holding part against an outer peripheral surface of said casing in hermetic relation.

16. The oxygen sensor as claimed in claim 15 wherein the filter holding part has an axial front relative to a stepped part formed in an axial intermediate part of the filter holding part as a first portion and a rear as a second portion so that the second portion is made smaller in diameter than the first portion, the gas introduction hole being made in a wall of the second portion; and a rear end part of said casing is inserted into the first portion of the filter holding part to a position at which it abuts directly or indirectly via a member the stepped part and the assembly coupling crimp part is formed in the overlap occurring in the first portion.

17. The oxygen sensor as claimed in claim 16 wherein the auxiliary filter holding part has an inner diameter smaller than an outer diameter of the first portion.

18. The oxygen sensor as claimed in claim 10 further including a ceramic separator being placed so that a rear thereof enters the inside of the filter holding part in an axial direction of said oxygen sensing element and a front enters the inside of said casing and formed with a plurality of lead insertion holes axially penetrating said ceramic separator for inserting leads from said oxygen sensing element.

19. The oxygen sensor as claimed in claim 18 wherein said ceramic separator is formed with a separator support part projecting from an outer peripheral surface of said ceramic separator at an intermediate position in an axial direction thereof;

said ceramic separator is placed so as to abut directly or indirectly via a member the rear end face of said casing at the separator support part in a state in which a portion positioned ahead the separator support part is located in a rear end of said casing, and is placed in a state in which a portion positioned behind the separator support part is projected to the outside of said casing; and the filter holding part having an axial rear second portion relative to a stepped part is placed so as to allow the projection of said ceramic separator to enter the inside of the second portion and cover the projection and abut directly or indirectly via a member the separator support part at the stepped part from an opposite side to said casing.

20. The oxygen sensor as claimed in claim 19 herein said ceramic separator is formed with a ventilation communication part axially penetrating said ceramic separator from a rear end face to a front end face thereof for introducing outside air flowing in through the gas introduction hole into the inside of said casing and the rear end face is positioned behind the gas introduction hole.

21. An oxygen sensor comprising:

an oxygen sensing element having a shape of a hollow shaft with a tip closed;

a shaft-shaped heating element being placed in the hollow shaft of said oxygen sensing element for heating said oxygen sensing element;

a cylindrical casing for housing said oxygen sensing element; and a ceramic separator being placed substantially coaxially with a rear end of said oxygen sensing element and formed with a plurality of lead insertion holes axially penetrating said ceramic separator for inserting leads from said oxygen sensing element and said heating element; wherein the lead insertion holes are arranged so as to surround a center axis of said ceramic separator;

said ceramic separator is formed with a heating element end housing hole opened at one end in the front end face of said ceramic separator with a bottom positioned in an axial intermediate part of said ceramic separator and an inner diameter set larger than an outer diameter of said heating element, the heating element end housing hole being formed by cutting away a center of said ceramic separator so as to overlap the separator lead insertion holes from the inside and a rear end part of said heating element being housed in the heating element end housing hole; and said heating element is offset so that a center axis thereof is one-sided with respect to a center axis of the hollow shaft of said oxygen sensing element in the proximity of a heating part of said heating element.

22. The oxygen sensor as claimed in claim 21 wherein the lead insertion holes are made so that centers thereof are positioned on a phantom circumferential path to form a pitch circle; and the inner diameter of the heating element end housing hole, d1, is set smaller than a diameter of the pitch circle, d2.

23. The oxygen sensor as claimed in claim 21 wherein the lead insertion holes are made so that centers thereof are positioned on a phantom circumferential path to form a pitch circle; and a ratio between the pitch circle diameter d2 and an outer diameter of the heating element end housing hole, D, d2/D, is adjusted in a range of 1.7 to 2.8.

24. The oxygen sensor as claimed in claim 21 wherein a ratio between a depth h and the inner diameter d1 of the heating element end housing hole, h/d1, is set to 1.2 or less.

25. An oxygen sensor comprising:

an oxygen sensing element with a shaft shape;

a cylindrical casing for housing said oxygen sensing element;

a filter assembly being placed substantially coaxially with said casing as a cylindrical body separate from said casing and coupled to said casing from a rear while allowing leads from said oxygen sensing element to extend to the rear outside of said filter assembly;

a ceramic separator being placed in said casing and formed with a plurality of lead insertion holes axially penetrating said ceramic separator for inserting leads from said oxygen sensing element; and an elastic seal member being coaxially integrated with a rear opening or a rear of said casing and fitted elastically onto a different cylindrical body communicating with said casing and seal lead insertion holes for inserting the leads and sealing a gap between outer faces of the leads and an inner face of said casing or the different cylindrical body, the elastic seal member being crimped from outside to secure a tight sealing; wherein an axial rear end face of said ceramic separator adheres closely to an axial front end face of said elastic seal member, wherein said ceramic separator is formed with a ventilation communication part axially penetrating said ceramic separator, and an opening of the ventilation communication part on a side near to said elastic seal member in the axial direction is made at a position where the opening is not shielded by said elastic seal member; wherein the seal member front end face includes one of a central projected portion and a peripheral projected portion so as to form a gap for passing air from the filter assembly to an inside of the sensing element; wherein said ceramic separator is formed with a through hole for axial ventilation in addition to the separator lead insertion holes and is formed on the rear end face with a ventilation groove communicating with the through hole for ventilation at one end and opened to an outer peripheral surface of said ceramic separator at an opposite end, the through hole for ventilation and the ventilation groove making up the ventilation communication part.

26. The oxygen sensor as claimed in claim 25 wherein said oxygen sensing element is formed as a hollow shaft with a tip closed and a shaft-shaped heating element for heating said oxygen sensing element is placed in the hollow shaft;

said ceramic separator has four separator lead insertion holes for inserting the leads from said oxygen sensing element and the heating element so that centers of the lead insertion holes are positioned on a phantom circumferential path to form a separator pitch circle;

the through hole for ventilation is made in an area surrounded by the four separator lead insertion holes at a center of said ceramic separator; and the ventilation groove having the shape of a cross at a position not interfering with the four separator lead insertion holes on the rear end face of said ceramic separator.

27. The oxygen sensor as claimed in claim 25 wherein said ceramic separator is formed with a separator support part forming a flange projecting from an outer peripheral surface of said ceramic separator at an intermediate position in an axial direction thereof, is placed so as to abut directly or indirectly via a member the rear end face of said casing at the separator support part in a state in which a portion positioned axially ahead the separator support part is entered in the rear end inside of said casing, and is placed in a state in which an axial rear portion is projected to the outside of said casing;

the projection of said ceramic separator from said casing is covered with a cover member as the different cylindrical body from the outside; and one or a plurality of the ventilation communication parts are formed so as to axially penetrate the flange part of said ceramic separator.

28. The oxygen sensor as claimed in claim 27 wherein the ventilation communication part is a plurality of grooves or notches made at substantially equal angle intervals in an outer peripheral surface of the flange part.

29. An oxygen sensor comprising:

an oxygen sensing element with a shaft shape;

a cylindrical casing for housing said oxygen sensing element;

a gas introduction structure comprising a filter holding part making a cylindrical form substantially coaxial with said casing on a rear of said casing, having an inside communicating with an inside of said casing, and one or more gas introduction holes being formed in a wall, a filter being placed so as to block the gas introduction hole or holes on an outside of the filter holding part for rejecting permeation of liquid and allowing gas to pass through, and an auxiliary filter holding part being formed like a cylinder placed on an outside of the filter and formed in a wall with one or more auxiliary gas introduction holes for sandwiching the filter between the auxiliary filter holding part and the filter holding part, for introducing outside air into said casing through the auxiliary gas introduction hole, the filter, and the gas introduction hole; wherein the filter holding part has an axial front relative to a stepped part formed in an axial intermediate part of the filter holding part as a first portion and a rear as a second portion so that the second portion is made smaller in diameter than the first portion, the gas introduction hole being made in a wall of the second portion;

the auxiliary filter holding part is placed so as to spread across the first and second portions of the filter holding part, and the filter comes in intimate contact with an inner face of the auxiliary filter holding part at least in surroundings of the auxiliary gas introduction hole;

a main coupling part for coupling the filter holding part and the auxiliary filter holding part to each other with the filter between is formed at a position corresponding to the second portion;

an auxiliary coupling part for coupling the filter holding part and the auxiliary filter holding part to each other is formed at a position corresponding to the first portion, the auxiliary coupling part defining a plurality of predetermined-length grooves extending in the axial direction of the filter holding part for communication with the outside and introducing outside air into the casing.

31. The oxygen sensor as claimed in claim 29 herein the filter is placed so as to circumferentially surround only the second portion of the filter holding part;

the main coupling part is an annular main crimp part formed along the circumferential direction of the second portion by crimping the auxiliary filter holding part toward the second portion of the filter holding part with the filter between; and the auxiliary coupling part is an annular auxiliary crimp part formed along a circumferential direction of the first portion by directly crimping the auxiliary filter holding part toward the first portion of the filter holding part.

31. The oxygen sensor as claimed in claim 30 wherein a plurality of the gas introduction holes and a plurality of the auxiliary gas introduction holes are made with a predetermined spacing along a circumferential direction in positional relationship corresponding to each other in an axial intermediate part in the filter holding part and the auxiliary filter holding part; and the main crimp part contains two crimp parts formed on both sides with a row of the gas introduction holes or the auxiliary gas introduction holes between.

32. An oxygen sensor comprising:

an oxygen sensing element with a shaft shape;

a cylindrical casing for housing said oxygen sensing element;

a gas introduction structure having a filter holding part making a cylindrical form substantially coaxial with said casing on a rear of said casing, having an inside communicating with an inside of said casing, and one or more gas introduction holes being formed in a wall and a filter being placed so as to block the gas introduction hole or holes of the filter holding part for rejecting permeation of liquid and allowing gas to pass through and an auxiliary filter holding part for fixing the filter to the filter holding part, said gas introduction structure for introducing outside air into said casing through the filter and the gas introduction hole or holes, wherein the auxiliary filter holding part includes a joint portion for joining to the filter holding part, the joint portion defining a plurality of predetermined-length grooves extending in the axial direction of the filter holding part for communication with the outside and introducing outside air into the casing;

a ceramic separator being placed so that a rear thereof enters the inside of the filter holding part in an axial direction of said oxygen sensing element and a front enters the inside of said casing and formed with a plurality of lead insertion holes axially penetrating said ceramic separator for inserting leads from said oxygen sensing element; and an elastic seal member being fitted elastically into a rear opening of the filter holding part and having seal lead insertion holes for inserting the leads for sealing a gap between outer faces of the leads and an inner face of the filter holding part; wherein a rear end face of said ceramic separator is positioned on the rear side behind the gas introduction hole in the axial direction and a predetermined gap is formed between said elastic seal member and said ceramic separator at least at the lead insertion position, and wherein said oxygen sensing element is formed as a hollow shaft with a tip closed and a shaft-shaped heating element for heating said oxygen sensing element is placed in the hollow shaft;

said ceramic separator has three or more separator lead insertion holes for inserting the leads from said oxygen sensing element and the heating element so that centers of the lead insertion holes are positioned on a phantom circumferential path to form a separator pitch circle;

said elastic seal member has three or more seal lead insertion holes for inserting the leads from said oxygen sensing element and the heating element so that centers of the lead insertion holes are positioned on a phantom circumferential path to form a seal pitch circle; and the separator pitch circle and the seal pitch circle are set so that the diameter of one is larger than that of the other, the leads being bent at a space between the elastic seal member and the ceramic separator.

33. The oxygen sensor as claimed in claims 32 wherein said elastic seal member is formed on a front end face with a gap definition projection whose tip abuts the rear end face of said ceramic separator for defining the size of the gap.

34. The oxygen sensor as claimed in claim 33 wherein the gap definition projection is formed in an area of the front end face of said elastic seal member, positioned inside the seal lead insertion holes arranged on a seal pitch circle; and the diameter of a separator pitch circle is set larger than that of the seal pitch circle.

35. The oxygen sensor as claimed in claim 32 wherein said elastic seal member is formed in a rear end margin with a flange part projecting outward from an outer peripheral surface and abuts the rear end face of the filter holding part at the flange part, whereby a front end face of said elastic seal member is positioned in the filter holding part.

* * * * *